US006855323B2

(12) United States Patent
Scherf et al.

(10) Patent No.: US 6,855,323 B2
(45) Date of Patent: Feb. 15, 2005

(54) **IDENTIFICATION OF THE DOMAIN OF *PLASMODIUM FALCIPARUM* ERYTHROCYTE MEMBRANE PROTEIN 1 (PFEMP1) THAT MEDIATES ADHESION TO CHONDROITIN SULFATE A**

(75) Inventors: Artur Scherf, Paris (FR); Louis H. Miller, Bethesda, MD (US); Benoit Gamain, Washington, DC (US); Dror I. Baruch, Rockville, MD (US); Pierre Buffet, Paris (FR); Christine Scheidig, Savigny le Temple (FR); Jurg Gysin, St. Zacharie (FR); Bruno Pouvelle, Saint Maximin la Sainte Baume (FR); Nobutaka Fujii, Kyoto (JP); Joseph Smith, Fort Collins, CO (US)

(73) Assignee: The United States of America as represented by the Department of Health and Human Services, Washington, DC (US)

(*) Notice: Subject to any disclaimer, the term of this patent is extended or adjusted under 35 U.S.C. 154(b) by 138 days.

(21) Appl. No.: 10/087,013

(22) Filed: Feb. 21, 2002

(65) Prior Publication Data

US 2004/0062769 A1 Apr. 1, 2004

Related U.S. Application Data

(63) Continuation of application No. PCT/US00/24195, filed on Sep. 1, 2000.
(60) Provisional application No. 60/152,023, filed on Sep. 1, 1999.

(51) Int. Cl.[7] .................... A61K 39/015; A61K 39/002; A61K 39/00; A61K 38/00; C07K 14/00

(52) U.S. Cl. ................................ 424/272.1; 424/184.1; 424/185.1; 424/191.1; 514/2; 530/300; 530/350

(58) Field of Search ............................ 435/4, 7.22, 7.1, 435/69.1; 514/2, 54, 62, 1, 8, 21; 530/350, 300, 326, 328, 331; 424/184.1, 185.1, 191.1, 192.1, 193.1, 265.1, 269.1, 272.1

(56) References Cited

U.S. PATENT DOCUMENTS 5,817,644 A * 10/1998 Gustafson .................... 514/54

FOREIGN PATENT DOCUMENTS

WO WO96/40766 12/1996

OTHER PUBLICATIONS

NCBI printout of Genbank Accession No. L42636.*

Sequence Comparisons, us–10–097–013–2.rag, pp. 10–12 (Result 5), us–10–087–013–2_copy_1279_1554.rag, pp. 3 and 6 (Results 4, 9, and 10).*

NCBI printout of Genbank Accession No. AF134154.*

NCBI printout of Genbank Accession No. AAD29126.*

Buffet et al., *Plasmodium falciparum* domain mediating adhesion to chondroitin sulfate A: A receptor for human placemental infection, PNAS 96: 12743 (Oct. 1999).

Scherf, A., FCR3 CSA ligand [*Plasmodium falciparum*], GenBank accession No. AJ133811 (Apr. 23, 1999).

Costa et al., Immunization with recombinant duffy–binding–like γ3 Induces pan–reactive and adhesion–blocking antibodies against placental chondroitin sulfate A–binding *plasmodium falciparum* parasites, JID 188: 153 (2003).

Gamain et al., Identification of a 67–amino acid region of the *plasmodium falciparum* variant surface antigen that binds chondroitin sulfate A and elicits antibodies reactive with the surface of placental isolates, in press.

Baruch, D. I., et al. (1995) Cloning the *P. falciparum* Gene Encoding PfEMP1, a Malarial Variant Antigen and Adherence Receptor on the Surface of Parasitized Human Erythrocytes. Cell 82:77–87.

Baruch, D. I., et al. (1996) *Plasmodium falciparum* Erythrocyte Membrane Protein 1 is a Parasitized Erythrocyte Receptor for Adherence to CD36, Thrombospondin, and Intercellular Adhesion Molecule 1. Proc. Natl. Acad. Sci. 93:3497–3502.

Baruch, D. I., et al. (1997) Identification of a Region of PfEMP1 That Mediates Adherence of *Plasmodium falciparum* Infected Erythrocytes to CD36: Conserved Function With Variant Sequence. Blood 90(9):3766–3775.

Berendt, A. R., et al. (1989) Intercellular adhesion molecule–1 is an endothelial cell adhesion receptor for *Plasmodium falciparum.* Nature 341:57–59.

Bevilacqua, M. P. et al. (1989) Endothelial Leukocyte Adhesion Molecule 1: An Inducible Receptor for Neutrophils Related to Complement Regulatory Proteins and Lectins. Science 243:1160–1165.

Buffet, P. A., et al. (1999) *Plasmodium falciparum* domain mediating adhesion to chondroitin sulfate A: A receptor for human placental infection. Proc. Natl. Acad. Sci. 96(22):12743–12748.

Buffet, P. A. et al., (1999) *Plasmodium falciparum* domain mediating adhesion to chondroitin sulfate A: a receptor for human placental infection. Database EMBL PFA133811, Accesion No. AJ133811.

(List continued on next page.)

*Primary Examiner*—James Housel
*Assistant Examiner*—Zachariah Lucas
(74) *Attorney, Agent, or Firm*—Knobbe, Martens, Olson & Bear, LLP

(57) ABSTRACT

The present invention relates to the discovery of a var gene and corresponding protein that modulates adhesion of parasitized red blood cells to chondroitin sulfate A. Novel biological tools, prophylactics, therapeutics, diagnostics, and methods of use of the foregoing are also disclosed.

8 Claims, 3 Drawing Sheets

OTHER PUBLICATIONS

Chen, Q., et al. (1998) Identification of *Plasmodium falciparum* Erythrocyte Membrane Protein 1 (PfEMP1) as the Rosetting Ligand of the Malaria Parasite *P. falciparum.* J. Exp. Med. 187:15–23.

Fried, M., et al. (1996) Adherence of *Plasmodium falciparum* to Chondroitin Sulfate A in the Human Placenta. Science 272:1502–1504.

Fried, M., et al. (1998) Maternal antibodies block malaria. Nature 395:851–852.

Gysin, J., et al. (1997) Chondroitin sulfate of thrombomodulin is an adhesion receptor for *Plasmodium falciparum*–infected erythrocytes. Mol. Biochem. Parasitol. 88:267–271.

Hernandez–Rivas, R., et al. (1997) Expressed *var* Genes Are Found in *Plasmodium falciparum* Subtelomeric Regions. Mol. Cell. Biol. 17(2):604–611.

Miller, L. H., et al. (1998) Motherhood and malaria. Nature Medicine 4(11):1244–1245.

Osborn, L., et al. (1989) Direct Expression Cloning of Vascular Cell Adhesion Molecule 1, a Cytokine–Induced Endothelial Protein That Binds to Lymphocytes. Cell 59:1203–1211.

Pasvol, G., et al. (1978) Separation of viable schizont–infected red cells of *Plasmodium falciparum* from human blood. Ann. Trop. Med. Parasitol. 72(1):87–88.

Pouvelle, B., et al. (1998) *Plasmodium falciparum* et chondroitine–4–sulfate: le nouveau couple cle de la sequestration. Med. Trop. 58:187–198.

Reeder, J. C., et al. (1999) The adhesion of *Plasmodium falciparum*–infected erythrocytes to chondroitin sulfate A is mediated by *P. falciparum* erythrocyte membrane protein 1. Proc. Natl. Acad. Sci. 96:5198–5202.

Robert, C., et al. (1995) Chondroitin–4–sulphate (proteoglycan), a receptor for *Plasmodium falciparum*–infected erythrocyte adherence on brain microvascular endothelial cells. Res. Immunol. 146:383–393.

Rogerson, S. J., et al. (1995) Chondroitin Sulphate A Is a Cell Surface Receptor for *Plasmodium falciparum*–infected Erythrocytes. J. Exp. Med. 182:15–20.

Rowe, J. A., et al. (1997) *P. falciparum* rosetting mediated by a parasite–variant erythrocyte membrane protein and complement–receptor 1. Nature 388:292–295.

Scherf, A. (1998) Antigenic variation in malaria: *in situ* switching, relaxed and mutually exclusive transcription of var genes during intra–erythorcytic development in *Plasmodium falciparum*. Database EMBL PFA7940, Accesion No. AJ007940.

Scherf, A., et al. (1998) Antigenic variation in malaria: in situ switching, relaxed and mutually exclusive transcription of var genes during intra–erythrocytic development in *Plasmodium falciparum*. EMBO J. 17(18):5418–5426.

Shinohara, Y., et al. (1995) Use of a Biosensor Based on Surface Plasmon Resonance and Biotinyl Glycans for Analysis of Sugar Binding Specificities of Lectins. J. Biochem. 117:1076–1082.

Simmons, D., et al. (1988) ICAM, an adhesion ligand of LFA–1, is homologous to the neural cell adhesion molecule NCAM. Nature 331:624–627.

Smith, J. D., et al. (1995) Switches in Expression of *Plasmodium falciparum var* Genes Correlate with Changes in Antigenic and Cytoadherent Phenotypes of Infected Erythrocytes. Cell 82:101–110.

Smith, J. D., et al. (1998) Analysis of adhesive domains from the A4VAR *Plasmodium falciparum* erythrocyte membrane protein–1 indentifies a CD36 binding domain. Mol. Biochem. Parasitol. 97:133–148.

Steketee, R. W., et al. (1996) The Problem of Malaria and Malaria Control in Pregnancy in Sub–Saharan Africa. Am. J. Trop. Med. Hyg. 55(1):2–7.

Su, X. Z., et al. (1995) The Large Diverse Gene Family var Encodes Proteins Involved in Cytoadherence and Antigenic Variation of *Plasmodium falciparum*–Infected Erythrocytes. Cell 82:89–100.

Vicart, P., et al. (1993) Cell Adhesion Markers Are Expressed by a Stable Human Endothelial Cell Line Transformed by the SV40 Large T Antigen Under Vimentin Promoter Control. J. Cell Physiol. 157:41–51.

Wiesner, J., et al. (1998) Biology of Giant Proteins of Plasmodium: Resolution on Polyacrylamide–Agarose Composite Gels. Parasitol. Today 14(1):38–40.

* cited by examiner

SEQUENCE LISTING

<160> NUMBER OF SEQ ID NOS: 11

<210> SEQ ID NO 1
<211> LENGTH: 10628
<212> TYPE: DNA
<213> ORGANISM: Plasmodium falciparum

<400> SEQUENCE: 1
atggggttct cctgcaaata ttttattata aaaatgggga atgcagcatc atcattagag 60
ggagatgcta aaagccctat tataaaagaa agtcacaaaa gtgcaagaaa tgttttggaa 120
cgttatgcca aaaatataag acatccatca aaatatgcaa aagaacatgt ggattcgttg 180
aaaggggatt tgacgaaagc agaatttcgt ggtggtcctt ctacgccagt aaataagcat 240
aattattatt atccatatcc atgtaattta gatcataagg aacatactaa tttacggtat 300
gatgatgtga atttgagaca tccttgccat ggtagagaac aaaaccgatt tgatgaagat 360
gaagaatctg aatgtggaaa taaaatacgt aattataaaa gaaaaaatga tgctatagcc 420
tgtgcgccac ctagaagacg acatatgtgt gataaaaact tggaagctct aaatgatata 480

-continued

```
aatacccaaa atattcatga tttattggga aatgtactag ttacagcaaa atacgaaggt    540
gaatcaattg ttaataatca tccacataaa ggaacttcag acgcttgtac tgctcttgca    600
cgaagttttg cagatatagg tgatattgta agaggaatag atatgtttaa accaaatgtc    660
catgacaaag tagaaacggg tctccgagag gttttcaaga aaatacatga tggaatggaa    720
gatgaagtaa aaaatgatta caatcctgat ggatctggaa attattataa attaagagaa    780
gcatggtgga atgtgaatag aaataaagta tgggaagcta taacatgtga tgcatcatat    840
aaatctggat attttatgca atcagaaagt aatacaccat tattttcaaa tcctaaatgc    900
ggccataaac aaggaaaggt tcctaccaat ttagattatg tccctcaata tttacgttgg    960
ttcgacgaat ggggagaaga gttttgccga aaaagaaata ttaaattgaa aaaggtcaag   1020
gactcctgtc gtaatgacaa agaacgctta tattgtagtc ataatggaca tgattgtacg   1080
acaactattt ggaaaaaagg tattttgcat ttggataata agtgtactga ctgttcgact   1140
aaatgcaaag tttttgaagt ttggttaggg aatcaacaag aagcatttaa aaaacaaaaa   1200
gaaaaatatg aaaaagaaat acaatcatat ttatcgaacg ataacaaatt tgtcaataat   1260
attaatagtg aatattataa acaattttat gaaaaactta aggaaacgca atatgcaact   1320
aatgacactt ttttaaattt actaaatgaa ggaaagtatt gtaaaggagg attaccagga   1380
gaaaaggata ttacttttac taacagtgct gatgacaaag ggatatttta tcgttcagaa   1440
tattgccaag tgtgtcccga ctgcggggtc aaatgtgatg gtataaaata cacacacaaa   1500
tcagataatg atcgtgaacg tgtaaataat gaagactata aacctccatg ggtgtgaag    1560
cctactaata tcactgtcct ttatagtggt aatgaacaag gtgatattac acaaaaatta   1620
gaaaattttt gtaacagctc aactaattac aaagataaaa ataatcaaaa atgggaatgc   1680
tattataagg atgaaaatat aaatagatgt aaactggaac aaaatactga aatcaataat   1740
gataatccta agataatatc atttcataat ttttttgaat tatgggttac atatttatta   1800
agggatacta ttaagtggaa tgacaaactt aaaacttgta taaataatac aaccacgcat   1860
tgtattgatg aatgtaacag aaattgctta tgttttgaca gatgggttaa acaaaaagaa   1920
gaagaatgga atagtataaa gaaactgttc acaaaaaaaa agaatataca gcaatcgtat   1980
tatagtaata ttaataatct ttttgaaggt tattttttta aagttatgga taaacttgac   2040
aaagatgaag caaaatggaa agaacttatg gaaaatataa aaagaaaaaa aaatgagttt   2100
tccaatttgg aaaataatag ggactattta gagaatgcaa tagaactctt gttagatcac   2160
ttaaaagaaa ctgccacgat atgtaaagac aataatacaa acgaagcatg tgaaacatcc   2220
cataatgcaa caacaaaccc gtgtgttaaa cctcgtggag gcacgcaacc cactaaaaat   2280
ataaaagaaa tagcacaata ctttaaaagg agtgcatacg aggaagcacg aaatcgtggt   2340
cttcataaat tgaaaggaaa ggcacacgaa ggtatatata aacgtggggg taggagaaag   2400
gacttcaagg acaatttatg tagaataatg ataaaacatt ctaatcgtaa tcttggtttt   2460
tcaaatggac catgtgatgg caaaggcaca ggtgatggta tacaaacaag atttgtcgta   2520
ggaactgaat gggaagtgga tccggaacac atgcgtaaag atcacgaaga tgttattatg   2580
cctcctagaa gacgacatat atgtacatcc aatttggaac atttacaaac ggatgatcac   2640
ccacttaatg gtaatattgt tgatgattta gttaataatt cctttttggg ggatgttctt   2700
ctatcagcaa aatatgaagc aaacaagata atacgaatgt ataaagaaaa gaataaccta   2760
aagggcccca aagaagtaac tgacccaaaa caccagacaa ctatctgtcg agctatacgt   2820
```

-continued

```
tacagttttg cagatatagg tgatataatt cgaggaagag atctctggga aagaaacggt   2880

gacatggtaa agctgcaagg acatttggaa actgtttttg gtaatataca taagtcactc   2940

aaaggcaaag gaaatgataa atataatgat gatgcccca aatatttaaa attgagggaa   3000

aattggtggg aagctaatag agccaaagta tgggaagcca tgaaatgtga tataaaatat   3060

ttgaaggata aatcgggaca ccaatcaaca caaagtagtt attgcggata tagtgatcat   3120

acaccattgg atgattatat cccacaaaaa ttaagatgga tgaccgaatg ggcagaatgg   3180

tactgcaagg tgcagaaaaa ggagtatgat aagttgaagg agaagtgtaa ggagtgtaag   3240

gataaggata atggtcaagg ctgtacgaaa gagagtggta caggttgtac gaagtgcaca   3300

gaagcttgta atgaatataa tgatataata ggattatgga aagaacaatg gaatataata   3360

tcagataaat acaaagaatt acatgaacaa gcacaaatgt ctgttagtaa tagtggtatt   3420

gaagcttcca gtactgccaa aaatcatata gacaggaatg ttattgaatt tttgtcggaa   3480

ttataccaac aaaatggtgg caaaagtaat aaaagtggta ctagtgatga aagtgctgtc   3540

attggtacta acaccacgta tgaaaatgtt ggagcatatc tccatgatac aggaaatttt   3600

gatgattgtc agtcacaaaa tgagttttgt gatgaaaaaa gtgatggtaa ggataacgaa   3660

aaatatgcct ttagagataa accacaggac catgatggtg cgtgtggttg taaaagtgga   3720

tcgaaaccga caagggtaca gataaaaacg aaaaaaaaag cggaagaaaa ggatacggaa   3780

tgtaaaacag tgaatgatat acttaaagaa aacgatggaa agaaacaagt agaagattgt   3840

catccaaaaa agaatagtaa tggatatccc gattggcaat gcggaaatat aaatttagtg   3900

gaagaccctc gtgtgtgtat gccccctaga agacaaaagt tatgcgtaca tttcttggca   3960

aatgataatg aaataaaaaa attacaatca caagttaatt taaaagaagc tttcatcaaa   4020

tctgcagcag cagaaacatt cttctcatgg tattattata aaagtaagga tggtgaagga   4080

aatgaactcg ataaagaatt aaaagaaggc aaaattcctc ccgcattttt gagatccatg   4140

ttctacacat ttggagatta tagagatttt ttatttggaa cagatatatc aaaaggtcat   4200

ggtgagggaa gtaaactaaa agagcaaata gattctcttt tcaaaaatgg tgaccaaaaa   4260

tctcctaatg gaaaaacacg ccaagaatgg tggacagaac atagtcatga gatatgggaa   4320

gctatgctat gtgcactagt aaaaattggg gcaaaaaaag atgattttac cgaaaactac   4380

ggttacaaca acgtcaaatt tagtgacaaa agcaccactt tggaggaatt tgccaaacga   4440

ccccagtttt tacgatggct aaccgaatgg tacgacgact attgctatac acgacaaaaa   4500

tatttgaagg atgtgcagga aaaatgtaag tcaaatgacc aattgaagtg tgatacagaa   4560

tgtaataaga aatgcgagga ctacgttaaa tatatgaaaa aaaaaaaaga gtggattcca   4620

caagataaat attacaagga tgaacgcgac aaaaaaagat tcgatagaca acacattggt   4680

gtaatggtta cagactatac tggaacgaat gcaacagatt acttgaacag gaaatttact   4740

gctagttgtg gtgataagcc tggaagtgcc tctgtggtac aaagaaatat acaattgtta   4800

gaaaaacagg cttactatga tgccgacaaa cattgtgggt gcacaaaatt tattgaaaat   4860

gacgacaaat atactaacat ttcgagtaaa gataagtgca aaggattagt aaaggaggca   4920

aacacaggtg ctattaagtg gcaaaacaaa ggtcctaata actacaataa cttgaaagaa   4980

ttgactgaag atgtgctttt tccttctcgt cgactacgta tatgttttca tgcattggat   5040

ggcaattata cagatccaga agttaaagat gaaaatgggt tgcgaaaaag attgatggaa   5100

gtggcggcaa cggaagggta caatttgggt caatactaca aagaaaaaaa agaaaaagag   5160

aaaataaaaa cgtcggatgc gcacaaatat tcttatgagg tcccgccttg tagtgctatg   5220
```

-continued aaatatagtt tttatgattt aagagatata attctaggta ttgataattt ggaagatgaa 5280
aaacaaaaga ccgaggaaaa tttgaagaaa atatttaaca aaaatggaac atcagttggc 5340
aaaggaagtg atagtactac aggaaatccc ggtagtactg cgcgaaaatt tttctggaac 5400
gaaaataagg aatgtgtgtg gaacgcaatg atatgcgggt acaaacgtgg tagggatgat 5460
ggaaatagtg gaaatagtgc aagaagtgat gaagatctaa aaaaatgtgg ttctgtacct 5520
tcagatgatg attatcctat ggggaaaaat cgcgatgaag gtactgcgta tcagtttctt 5580
cgatggtttg ccgaatgggg tgaagatttt tgcaaacata aagaaaagga attggagaaa 5640
ttggtagggg cgtgtaatga ttatacttgt ggtgataatg aagataaaag aaagaaatgt 5700
acagatgcgt gtacacaata taaaaaattt attagtgagt ggaaaccaca gtatgaaaaa 5760
caaatcaaaa aatatggtga gaataaagac aaaatatatt ccgagcatcc tgtggcaaaa 5820
gatgcagagg acgctcgcga atatttagac aaacaattaa aaaaaatttg tgaaaataaa 5880
agtggagatt gtgaatataa gtgtatgaaa gatgtgtcca cacagcgatt aactgatggt 5940
aatagtcaaa atatgcccgc atcattagac gatgaaccaa aagaagttga aggaaagtgt 6000
aattgtcaag tgccacgagg tccaccacgt gtacgaaggg aaacaccgtc accacgggta 6060
tcactgatat caaaagcgac ggcatcgaaa aaagaagcga aaacagcgcc gcctacaaaa 6120
cagccgaaaa aagtggaaaa tctaacaaca gaaatgcgag cacaaacacg aacccgacga 6180
gcagcacaac aaacacgaaa acgaacatca acagcaacaa caacagaatc tgacgtgggc 6240
acaatggtaa aggccattct ttcgaataaa ccagatagca ggggtggaat agagggttgt 6300
aatccaaaaa cgtatggaca atatcctaaa tggggttgta ttgtaggtaa gtctaaagaa 6360
aatgaaaatg gcatatgtat gcctcctagg agaaaaaaat tatgtataaa taatatacaa 6420
tatttaaatt atgaaactga aaataagcgt gacaatgata taaaagaggc ttttattaaa 6480
tgtgcagcaa tagaaactca atttttgtgg ttaaaatata taattgaaaa tcctgcagca 6540
gaaaatgaat tgcaaaatgg aacaattcca gatgaattta aaagaataat gtattataca 6600
tatggtgatt ataaagatat gtttttttgga actgatattt ctaatgataa aaaaattata 6660
actgtaacaa atagtgtaac aaccattctc aatgaaaata ataagaaaaa acaggataaa 6720
aaaaaagatg aagaattacg taaaatattt tgggagaaaa ataaaaaatt tatttgggaa 6780
ggaatgatat atggattaac ttatcatctc acagacgaaa acgaaaaaga aaaaattaga 6840
gataattacc agtacaatga catgaccaaa ctgacgcctt cccttgaaga gtttgtaaaa 6900
aggccccaat tttgagatg gttcacagaa tgggcagaag aattttgtaa taagaggaag 6960
gaacagttgt taaaattgga ggcgggctgt aaggaatatg agtgtaatgg tagtaatgac 7020
ggtaagacac aagaatgtgc agaggcgtgt gtaacatatc aaaattttat taagaagtgg 7080
aaaactgaat atgaaagaca aagagaaaag ttcaaaaagg ataaagatgg caaaaagtat 7140
aaggattatc cttctactga aagagacata gagaaggcaa catgtgctca tgaatattta 7200
aacatgaaat taaaagaatt atgtggcaat aaggattgtt cttgtatgca aaaaccttct 7260
tcacaactac caaaaacaac acaacaatca caatcatccg atgctaatga tatgccagaa 7320
tcgctggatt atgttcctga agaatttaac aagtgtgagt gtcctgaact ttcaaaaaag 7380
ggatctatga ttcatacaaa aaaaattact gaacctaaaa tacctatgaa ttgtgtagag 7440
aaagcagcat attatttatc taaagaagca gaaaataata tggatattac cttgaaggaa 7500
aaatttatac ctattgagtc tacaaaggaa aaggaaagta aaaatagttg gactaataat 7560

-continued

```
aatccttgcg atcctaagaa accttatgca cctgataaat atataggaag aagaaaccct   7620
tgtgaaaata gagaagaaaa tcgttttaag gtagattatg aatggaaatg ttacaaaaat   7680
tcaaagttct atcaggagaa aaaaagagta tgtgtacctc caagaagaga acatatgtgc   7740
ttaaggaatt tagatgaaat taaaattgaa agacttaagg atagtaatta tctcctaaaa   7800
atggttcgtc gaactgcacg aaatgaagga atagacataa taaaaaactt caactcagag   7860
aacgggtgcg caatgaatcc aatatgtgat actatgaaat atagtttcgc tgatctgggt   7920
gacatagtta gaggaacaga tatgttacga attggtggtt acttacctcc cgtagaaata   7980
aaattatata aggtttttga atacatatat ggaaaatgga gaaataaaaa taaaggtaga   8040
aataaataca acgatgtaca aacgtttcgt tctgcttggt gggatgctaa tagaaaagat   8100
atttggaaag caatgacgtg caaagcacca gaagatgcaa aactttttag aaaaggaaga   8160
atggatggat ttgaacgcat aacattaata caagataagt gtggacataa ggacgatcca   8220
cctgttgatg attatatacc tcaacggttt cgatggatga ctgaatggtc tgaatattat   8280
tgtaaagcac tgatggaaga attggaaaaa tttaaaaaat catgtgatca ctgtaaaaca   8340
tctgacagat gcaagaatga ttatgatgaa aataagtgtg aacagtgtaa aacgagatgt   8400
caagaatata aaaattttgt tcttaaatgg aaatctctat tcgatataca atcaaataaa   8460
tacaaagaat tgtatgaaca accaatatat acaaaaatct ctacttatga tcatgttcaa   8520
aattttgtac aaaagttgaa aactttttaaa agtgaatgtt ctgttgagag cttttctgaa   8580
tatcttcatg aaacaagtaa gtgtttgaat tataaattta atgaaaatga tggttcttcc   8640
aatatacgaa catatgcttt cgaagaaaca ccaaaaagtt ataaagaagc ttgcagttgt   8700
acactacctt ctaagaatcc attggataat tgtcctaccg atcaaaacaa agatggatgt   8760
aaggaattac aaacttttac cttctgctcg aagaatgatt atgataataa tcttgataat   8820
tggaacgcat accttgttct taatagttca gatgataaca aaggtgtatt gattcctcca   8880
agaagaagac atttatgtac aagacctatc actgcatata attatagaaa aggtgataaa   8940
gaaattttaa aaaaaaaact tcttacttct gctttcagtc aaggacaatt gttaggtcaa   9000
aaatataaat cggaagaaga gttgtgcttt gaggcaatga aatatagtta tgcagattat   9060
tccgatataa ttaaaggaac tgatatgatg gacacttcat tatctgaaaa aattaaaaaa   9120
atatttgaaa catcaaatga agcaaccgaa aatcgtaaaa catggtggga aaataataga   9180
cgtcagatat ggcacgctat gttatgtgga tataaaattg ctacttcaaa agtaacatta   9240
gatgaaggat ggtgtcaatt accaaaggat gaagaaacta atcagtttct tcgttggtta   9300
attgaatggg caaagcaagc atgtaaggaa aagaaacatg taagtgattc attaaaaaca   9360
aaatgtcctc gttcaaacga agataatttt gaagcgtcag aattattaag acaacctgga   9420
tgtcagaatg atattagaaa atatattagc ttgaatatat tgataaaaaa tacaatggaa   9480
aatctaaata taaaatataa gcaattaaaa gatcaatctt caggtaatat agacaataaa   9540
ccatctgaag aaaatgttca gtcatatata aaatcaaaag attctcaatg cgctttggag   9600
ttaaatgata taaatgaaat agttacagga acaaaaaata atgaaaataa tgaattcaaa   9660
gaagtactaa aaaaattata tcctggttta tattttgttg aagatgaaac acacaaaaat   9720
catgtactag atggaaatat aaaagaagaa gagcaaacag ttcgtcctaa agcactctat   9780
ttctttacac cccatgtaga ttctttctat caagcacctt tattctcaac acatcgagta   9840
gcacaatatg atcctaaaaa tgatatattg aaaagtagta tctctgttgt tattgtatcg   9900
gcgttaggtt tgatagcgct tcatttcatg aagaaaaaat tcaaatcgtc tgtggacttg   9960
```

-continued

```
ttgcgtatac tgaatatccc gcaaggagag tatggaatgc ctacgttgga atccaaaaat  10020

aggtacatac catatagaag tggtccatat aaaggcaaaa catatatata tatggaagga  10080

gatactagtg gagatgaaga taaatatatg tgggacttat cttcctctga tattacttca  10140

tccgaaagtg agtatgaaga attggatatt aatgatatat atgtaccagg tagtcctaaa  10200

tataaaacat tgatagaagt agtactagaa ccatcaaaaa gggatatacc aagtgatgat  10260

acaccaagta atgatacacc acgtacgaat agatttattg atgatgaatg gaatgaactg  10320

aaacatgatt ttgtatctca atatttacca aatacagaac caaataataa ttacaaaagt  10380

gcagatattc caatgaatac agaacctaat actttatatt ctgataatcc tgaagaaaaa  10440

ccttttatta tatctattca tgatagggat ttatatactg ggaaagaaat tagttataat  10500

attaatatga gtactaatac taataatgat attccaatga atgctagaaa tgattcttat  10560

agaggtatag atttaattaa tgattcacta gtggtgctaa acctattgat atatatgatg  10620

aagtattg                                                            10628
```

```
<210> SEQ ID NO 2
<211> LENGTH: 3542
<212> TYPE: PRT
<213> ORGANISM: Plasmodium falciparum

<400> SEQUENCE: 2

Met Gly Phe Ser Cys Lys Tyr Phe Ile Ile Lys Met Gly Asn Ala Ala
 1               5                  10                  15

Ser Ser Leu Glu Gly Asp Ala Lys Ser Pro Ile Ile Lys Glu Ser His
            20                  25                  30

Lys Ser Ala Arg Asn Val Leu Glu Arg Tyr Ala Lys Asn Ile Arg His
        35                  40                  45

Pro Ser Lys Tyr Ala Lys Glu His Val Asp Ser Leu Lys Gly Asp Leu
    50                  55                  60

Thr Lys Ala Glu Phe Arg Gly Gly Pro Ser Thr Pro Val Asn Lys His
65                  70                  75                  80

Asn Tyr Tyr Tyr Pro Tyr Pro Cys Asn Leu Asp His Lys Glu His Thr
                85                  90                  95

Asn Leu Arg Tyr Asp Asp Val Asn Leu Arg His Pro Cys His Gly Arg
            100                 105                 110

Glu Gln Asn Arg Phe Asp Glu Asp Glu Glu Ser Glu Cys Gly Asn Lys
        115                 120                 125

Ile Arg Asn Tyr Lys Arg Lys Asn Asp Ala Ile Ala Cys Ala Pro Pro
    130                 135                 140

Arg Arg Arg His Met Cys Asp Lys Asn Leu Glu Ala Leu Asn Asp Ile
145                 150                 155                 160

Asn Thr Gln Asn Ile His Asp Leu Leu Gly Asn Val Leu Val Thr Ala
                165                 170                 175

Lys Tyr Glu Gly Glu Ser Ile Val Asn Asn His Pro His Lys Gly Thr
            180                 185                 190

Ser Asp Ala Cys Thr Ala Leu Ala Arg Ser Phe Ala Asp Ile Gly Asp
        195                 200                 205

Ile Val Arg Gly Ile Asp Met Phe Lys Pro Asn Val His Asp Lys Val
    210                 215                 220

Glu Thr Gly Leu Arg Glu Val Phe Lys Lys Ile His Asp Gly Met Glu
225                 230                 235                 240

Asp Glu Val Lys Asn Asp Tyr Asn Pro Asp Gly Ser Gly Asn Tyr Tyr
```

-continued

```
                245                 250                 255

Lys Leu Arg Glu Ala Trp Trp Asn Val Asn Arg Asn Lys Val Trp Glu
            260                 265                 270

Ala Ile Thr Cys Asp Ala Ser Tyr Lys Ser Gly Tyr Phe Met Gln Ser
        275                 280                 285

Glu Ser Asn Thr Pro Leu Phe Ser Asn Pro Lys Cys Gly His Lys Gln
    290                 295                 300

Gly Lys Val Pro Thr Asn Leu Asp Tyr Val Pro Gln Tyr Leu Arg Trp
305                 310                 315                 320

Phe Asp Glu Trp Gly Glu Glu Phe Cys Arg Lys Arg Asn Ile Lys Leu
                325                 330                 335

Lys Lys Val Lys Asp Ser Cys Arg Asn Asp Lys Glu Arg Leu Tyr Cys
            340                 345                 350

Ser His Asn Gly His Asp Cys Thr Thr Thr Ile Trp Lys Lys Gly Ile
        355                 360                 365

Leu His Leu Asp Asn Lys Cys Thr Asp Cys Ser Thr Lys Cys Lys Val
    370                 375                 380

Phe Glu Val Trp Leu Gly Asn Gln Gln Glu Ala Phe Lys Lys Gln Lys
385                 390                 395                 400

Glu Lys Tyr Glu Lys Glu Ile Gln Ser Tyr Leu Ser Asn Asp Asn Lys
                405                 410                 415

Phe Val Asn Asn Ile Asn Ser Glu Tyr Tyr Lys Gln Phe Tyr Glu Lys
            420                 425                 430

Leu Lys Glu Thr Gln Tyr Ala Thr Asn Asp Thr Phe Leu Asn Leu Leu
        435                 440                 445

Asn Glu Gly Lys Tyr Cys Lys Gly Gly Leu Pro Gly Glu Lys Asp Ile
    450                 455                 460

Thr Phe Thr Asn Ser Ala Asp Asp Lys Gly Ile Phe Tyr Arg Ser Glu
465                 470                 475                 480

Tyr Cys Gln Val Cys Pro Asp Cys Gly Val Lys Cys Asp Gly Ile Lys
                485                 490                 495

Tyr Thr His Lys Ser Asp Asn Asp Arg Glu Arg Val Asn Asn Glu Asp
            500                 505                 510

Tyr Lys Pro Pro Trp Gly Val Lys Pro Thr Asn Ile Thr Val Leu Tyr
        515                 520                 525

Ser Gly Asn Glu Gln Gly Asp Ile Thr Gln Lys Leu Glu Asn Phe Cys
    530                 535                 540

Asn Ser Ser Thr Asn Tyr Lys Asp Lys Asn Asn Gln Lys Trp Glu Cys
545                 550                 555                 560

Tyr Tyr Lys Asp Glu Asn Ile Asn Arg Cys Lys Leu Glu Gln Asn Thr
                565                 570                 575

Glu Ile Asn Asn Asp Asn Pro Lys Ile Ile Ser Phe His Asn Phe Phe
            580                 585                 590

Glu Leu Trp Val Thr Tyr Leu Leu Arg Asp Thr Ile Lys Trp Asn Asp
        595                 600                 605

Lys Leu Lys Thr Cys Ile Asn Asn Thr Thr Thr His Cys Ile Asp Glu
    610                 615                 620

Cys Asn Arg Asn Cys Leu Cys Phe Asp Arg Trp Val Lys Gln Lys Glu
625                 630                 635                 640

Glu Glu Trp Asn Ser Ile Lys Lys Leu Phe Thr Lys Lys Lys Asn Ile
                645                 650                 655

Gln Gln Ser Tyr Tyr Ser Asn Ile Asn Asn Leu Phe Glu Gly Tyr Phe
            660                 665                 670
```

-continued

Phe Lys Val Met Asp Lys Leu Asp Lys Asp Glu Ala Lys Trp Lys Glu
675 680 685

Leu Met Glu Asn Ile Lys Arg Lys Lys Asn Glu Phe Ser Asn Leu Glu
690 695 700

Asn Asn Arg Asp Tyr Leu Glu Asn Ala Ile Glu Leu Leu Leu Asp His
705 710 715 720

Leu Lys Glu Thr Ala Thr Ile Cys Lys Asp Asn Asn Thr Asn Glu Ala
725 730 735

Cys Glu Thr Ser His Asn Ala Thr Thr Asn Pro Cys Val Lys Pro Arg
740 745 750

Gly Gly Thr Gln Pro Thr Lys Asn Ile Lys Glu Ile Ala Gln Tyr Phe
755 760 765

Lys Arg Ser Ala Tyr Glu Glu Ala Arg Asn Arg Gly Leu His Lys Leu
770 775 780

Lys Gly Lys Ala His Glu Gly Ile Tyr Lys Arg Gly Gly Arg Arg Lys
785 790 795 800

Asp Phe Lys Asp Asn Leu Cys Arg Ile Met Ile Lys His Ser Asn Arg
805 810 815

Asn Leu Gly Phe Ser Asn Gly Pro Cys Asp Gly Lys Gly Thr Gly Asp
820 825 830

Gly Ile Gln Thr Arg Phe Val Val Gly Thr Glu Trp Glu Val Asp Pro
835 840 845

Glu His Met Arg Lys Asp His Glu Asp Val Ile Met Pro Pro Arg Arg
850 855 860

Arg His Ile Cys Thr Ser Asn Leu Glu His Leu Gln Thr Asp Asp His
865 870 875 880

Pro Leu Asn Gly Asn Ile Val Asp Asp Leu Val Asn Asn Ser Phe Leu
885 890 895

Gly Asp Val Leu Leu Ser Ala Lys Tyr Glu Ala Asn Lys Ile Ile Arg
900 905 910

Met Tyr Lys Glu Lys Asn Asn Leu Lys Gly Pro Lys Glu Val Thr Asp
915 920 925

Pro Lys His Gln Thr Thr Ile Cys Arg Ala Ile Arg Tyr Ser Phe Ala
930 935 940

Asp Ile Gly Asp Ile Ile Arg Gly Arg Asp Leu Trp Glu Arg Asn Gly
945 950 955 960

Asp Met Val Lys Leu Gln Gly His Leu Glu Thr Val Phe Gly Asn Ile
965 970 975

His Lys Ser Leu Lys Gly Lys Gly Asn Asp Lys Tyr Asn Asp Asp Ala
980 985 990

Pro Lys Tyr Leu Lys Leu Arg Glu Asn Trp Trp Glu Ala Asn Arg Ala
995 1000 1005

Lys Val Trp Glu Ala Met Lys Cys Asp Ile Lys Tyr Leu Lys Asp Lys
1010 1015 1020

Ser Gly His Gln Ser Thr Gln Ser Ser Tyr Cys Gly Tyr Ser Asp His
1025 1030 1035 1040

Thr Pro Leu Asp Asp Tyr Ile Pro Gln Lys Leu Arg Trp Met Thr Glu
1045 1050 1055

Trp Ala Glu Trp Tyr Cys Lys Val Gln Lys Lys Glu Tyr Asp Lys Leu
1060 1065 1070

Lys Glu Lys Cys Lys Glu Cys Lys Asp Lys Asp Asn Gly Gln Gly Cys
1075 1080 1085

-continued

```
Thr Lys Glu Ser Gly Thr Gly Cys Thr Lys Cys Thr Glu Ala Cys Asn
    1090                1095                1100

Glu Tyr Asn Asp Ile Ile Gly Leu Trp Lys Glu Gln Trp Asn Ile Ile
1105                1110                1115                1120

Ser Asp Lys Tyr Lys Glu Leu His Glu Gln Ala Gln Met Ser Val Ser
                1125                1130                1135

Asn Ser Gly Ile Glu Ala Ser Ser Thr Ala Lys Asn His Ile Asp Arg
            1140                1145                1150

Asn Val Ile Glu Phe Leu Ser Glu Leu Tyr Gln Gln Asn Gly Gly Lys
        1155                1160                1165

Ser Asn Lys Ser Gly Thr Ser Asp Glu Ser Ala Val Ile Gly Thr Asn
    1170                1175                1180

Thr Thr Tyr Glu Asn Val Gly Ala Tyr Leu His Asp Thr Gly Asn Phe
1185                1190                1195                1200

Asp Asp Cys Gln Ser Gln Asn Glu Phe Cys Asp Glu Lys Ser Asp Gly
                1205                1210                1215

Lys Asp Asn Glu Lys Tyr Ala Phe Arg Asp Lys Pro Gln Asp His Asp
            1220                1225                1230

Gly Ala Cys Gly Cys Lys Ser Gly Ser Lys Pro Thr Arg Val Gln Ile
        1235                1240                1245

Lys Thr Lys Lys Lys Ala Glu Glu Lys Asp Thr Glu Cys Lys Thr Val
    1250                1255                1260

Asn Asp Ile Leu Lys Glu Asn Asp Gly Lys Lys Gln Val Glu Asp Cys
1265                1270                1275                1280

His Pro Lys Lys Asn Ser Asn Gly Tyr Pro Asp Trp Gln Cys Gly Asn
                1285                1290                1295

Ile Asn Leu Val Glu Asp Pro Arg Val Cys Met Pro Pro Arg Arg Gln
            1300                1305                1310

Lys Leu Cys Val His Phe Leu Ala Asn Asp Asn Glu Ile Lys Lys Leu
        1315                1320                1325

Gln Ser Gln Val Asn Leu Lys Glu Ala Phe Ile Lys Ser Ala Ala Ala
    1330                1335                1340

Glu Thr Phe Phe Ser Trp Tyr Tyr Tyr Lys Ser Lys Asp Gly Glu Gly
1345                1350                1355                1360

Asn Glu Leu Asp Lys Glu Leu Lys Glu Gly Lys Ile Pro Pro Ala Phe
                1365                1370                1375

Leu Arg Ser Met Phe Tyr Thr Phe Gly Asp Tyr Arg Asp Phe Leu Phe
            1380                1385                1390

Gly Thr Asp Ile Ser Lys Gly His Gly Glu Gly Ser Lys Leu Lys Glu
        1395                1400                1405

Gln Ile Asp Ser Leu Phe Lys Asn Gly Asp Gln Lys Ser Pro Asn Gly
    1410                1415                1420

Lys Thr Arg Gln Glu Trp Trp Thr Glu His Ser His Glu Ile Trp Glu
1425                1430                1435                1440

Ala Met Leu Cys Ala Leu Val Lys Ile Gly Ala Lys Lys Asp Asp Phe
                1445                1450                1455

Thr Glu Asn Tyr Gly Tyr Asn Asn Val Lys Phe Ser Asp Lys Ser Thr
            1460                1465                1470

Thr Leu Glu Glu Phe Ala Lys Arg Pro Gln Phe Leu Arg Trp Leu Thr
        1475                1480                1485

Glu Trp Tyr Asp Asp Tyr Cys Tyr Thr Arg Gln Lys Tyr Leu Lys Asp
    1490                1495                1500

Val Gln Glu Lys Cys Lys Ser Asn Asp Gln Leu Lys Cys Asp Thr Glu
```

-continued

```
1505                1510                1515                1520

Cys Asn Lys Lys Cys Glu Asp Tyr Val Lys Tyr Met Lys Lys Lys Lys
                1525                1530                1535

Glu Trp Ile Pro Gln Asp Lys Tyr Tyr Lys Asp Glu Arg Asp Lys Lys
            1540                1545                1550

Arg Phe Asp Arg Gln His Ile Gly Val Met Val Thr Asp Tyr Thr Gly
        1555                1560                1565

Thr Asn Ala Thr Asp Tyr Leu Asn Arg Lys Phe Thr Ala Ser Cys Gly
    1570                1575                1580

Asp Lys Pro Gly Ser Ala Ser Val Val Gln Arg Asn Ile Gln Leu Leu
1585                1590                1595                1600

Glu Lys Gln Ala Tyr Tyr Asp Ala Asp Lys His Cys Gly Cys Thr Lys
                1605                1610                1615

Phe Ile Glu Asn Asp Asp Lys Tyr Thr Asn Ile Ser Ser Lys Asp Lys
            1620                1625                1630

Cys Lys Gly Leu Val Lys Glu Ala Asn Thr Gly Ala Ile Lys Trp Gln
        1635                1640                1645

Asn Lys Gly Pro Asn Asn Tyr Asn Asn Leu Lys Glu Leu Thr Glu Asp
    1650                1655                1660

Val Leu Phe Pro Ser Arg Arg Leu Arg Ile Cys Phe His Ala Leu Asp
1665                1670                1675                1680

Gly Asn Tyr Thr Asp Pro Glu Val Lys Asp Glu Asn Gly Leu Arg Lys
                1685                1690                1695

Arg Leu Met Glu Val Ala Ala Thr Glu Gly Tyr Asn Leu Gly Gln Tyr
            1700                1705                1710

Tyr Lys Glu Lys Lys Glu Lys Glu Lys Ile Lys Thr Ser Asp Ala His
        1715                1720                1725

Lys Tyr Ser Tyr Glu Val Pro Pro Cys Ser Ala Met Lys Tyr Ser Phe
    1730                1735                1740

Tyr Asp Leu Arg Asp Ile Ile Leu Gly Ile Asp Asn Leu Glu Asp Glu
1745                1750                1755                1760

Lys Gln Lys Thr Glu Glu Asn Leu Lys Lys Ile Phe Asn Lys Asn Gly
                1765                1770                1775

Thr Ser Val Gly Lys Gly Ser Asp Ser Thr Thr Gly Asn Pro Gly Ser
            1780                1785                1790

Thr Ala Arg Lys Phe Phe Trp Asn Glu Asn Lys Glu Cys Val Trp Asn
        1795                1800                1805

Ala Met Ile Cys Gly Tyr Lys Arg Gly Arg Asp Asp Gly Asn Ser Gly
    1810                1815                1820

Asn Ser Ala Arg Ser Asp Glu Asp Leu Lys Lys Cys Gly Ser Val Pro
1825                1830                1835                1840

Ser Asp Asp Asp Tyr Pro Met Gly Lys Asn Arg Asp Glu Gly Thr Ala
                1845                1850                1855

Tyr Gln Phe Leu Arg Trp Phe Ala Glu Trp Gly Glu Asp Phe Cys Lys
            1860                1865                1870

His Lys Glu Lys Glu Leu Glu Lys Leu Val Gly Ala Cys Asn Asp Tyr
        1875                1880                1885

Thr Cys Gly Asp Asn Glu Asp Lys Arg Lys Lys Cys Thr Asp Ala Cys
    1890                1895                1900

Thr Gln Tyr Lys Lys Phe Ile Ser Glu Trp Lys Pro Gln Tyr Glu Lys
1905                1910                1915                1920

Gln Ile Lys Lys Tyr Gly Glu Asn Lys Asp Lys Ile Tyr Ser Glu His
                1925                1930                1935
```

-continued

```
Pro Val Ala Lys Asp Ala Glu Asp Ala Arg Glu Tyr Leu Asp Lys Gln
            1940                1945                1950

Leu Lys Lys Ile Cys Glu Asn Lys Ser Gly Asp Cys Glu Tyr Lys Cys
        1955                1960                1965

Met Lys Asp Val Ser Thr Gln Arg Leu Thr Asp Gly Asn Ser Gln Asn
    1970                1975                1980

Met Pro Ala Ser Leu Asp Asp Glu Pro Lys Glu Val Glu Gly Lys Cys
1985                1990                1995                2000

Asn Cys Gln Val Pro Arg Gly Pro Pro Arg Val Arg Arg Glu Thr Pro
                2005                2010                2015

Ser Pro Arg Val Ser Leu Ile Ser Lys Ala Thr Ala Ser Lys Lys Glu
            2020                2025                2030

Ala Lys Thr Ala Pro Pro Thr Lys Gln Pro Lys Lys Val Glu Asn Leu
        2035                2040                2045

Thr Thr Glu Met Arg Ala Gln Thr Arg Thr Arg Arg Ala Ala Gln Gln
    2050                2055                2060

Thr Arg Lys Arg Thr Ser Thr Ala Thr Thr Thr Glu Ser Asp Val Gly
2065                2070                2075                2080

Thr Met Val Lys Ala Ile Leu Ser Asn Lys Pro Asp Ser Arg Gly Gly
                2085                2090                2095

Ile Glu Gly Cys Asn Pro Lys Thr Tyr Gly Gln Tyr Pro Lys Trp Gly
            2100                2105                2110

Cys Ile Val Gly Lys Ser Lys Glu Asn Glu Asn Gly Ile Cys Met Pro
        2115                2120                2125

Pro Arg Arg Lys Lys Leu Cys Ile Asn Asn Ile Gln Tyr Leu Asn Tyr
    2130                2135                2140

Glu Thr Glu Asn Lys Arg Asp Asn Asp Ile Lys Glu Ala Phe Ile Lys
2145                2150                2155                2160

Cys Ala Ala Ile Glu Thr Gln Phe Leu Trp Leu Lys Tyr Ile Ile Glu
                2165                2170                2175

Asn Pro Ala Ala Glu Asn Glu Leu Gln Asn Gly Thr Ile Pro Asp Glu
            2180                2185                2190

Phe Lys Arg Ile Met Tyr Tyr Thr Tyr Gly Asp Tyr Lys Asp Met Phe
        2195                2200                2205

Phe Gly Thr Asp Ile Ser Asn Asp Lys Lys Ile Ile Thr Val Thr Asn
    2210                2215                2220

Ser Val Thr Thr Ile Leu Asn Glu Asn Asn Lys Lys Lys Gln Asp Lys
2225                2230                2235                2240

Lys Lys Asp Glu Glu Leu Arg Lys Ile Phe Trp Glu Lys Asn Lys Lys
                2245                2250                2255

Phe Ile Trp Glu Gly Met Ile Tyr Gly Leu Thr Tyr His Leu Thr Asp
            2260                2265                2270

Glu Asn Glu Lys Glu Lys Ile Arg Asp Asn Tyr Gln Tyr Asn Asp Met
        2275                2280                2285

Thr Lys Leu Thr Pro Ser Leu Glu Glu Phe Val Lys Arg Pro Gln Phe
    2290                2295                2300

Leu Arg Trp Phe Thr Glu Trp Ala Glu Glu Phe Cys Asn Lys Arg Lys
2305                2310                2315                2320

Glu Gln Leu Leu Lys Leu Glu Ala Gly Cys Lys Glu Tyr Glu Cys Asn
                2325                2330                2335

Gly Ser Asn Asp Gly Lys Thr Gln Glu Cys Ala Glu Ala Cys Val Thr
            2340                2345                2350
```

-continued

```
Tyr Gln Asn Phe Ile Lys Lys Trp Lys Thr Glu Tyr Glu Arg Gln Arg
        2355                2360                2365

Glu Lys Phe Lys Lys Asp Lys Asp Gly Lys Lys Tyr Lys Asp Tyr Pro
    2370                2375                2380

Ser Thr Glu Arg Asp Ile Glu Lys Ala Thr Cys Ala His Glu Tyr Leu
2385                2390                2395                2400

Asn Met Lys Leu Lys Glu Leu Cys Gly Asn Lys Asp Cys Ser Cys Met
                2405                2410                2415

Gln Lys Pro Ser Ser Gln Leu Pro Lys Thr Thr Gln Gln Ser Gln Ser
            2420                2425                2430

Ser Asp Ala Asn Asp Met Pro Glu Ser Leu Asp Tyr Val Pro Glu Glu
        2435                2440                2445

Phe Asn Lys Cys Glu Cys Pro Glu Leu Ser Lys Lys Gly Ser Met Ile
    2450                2455                2460

His Thr Lys Lys Ile Thr Glu Pro Lys Ile Pro Met Asn Cys Val Glu
2465                2470                2475                2480

Lys Ala Ala Tyr Tyr Leu Ser Lys Glu Ala Glu Asn Asn Met Asp Ile
                2485                2490                2495

Thr Leu Lys Glu Lys Phe Ile Pro Ile Glu Ser Thr Lys Glu Lys Glu
            2500                2505                2510

Ser Lys Asn Ser Trp Thr Asn Asn Asn Pro Cys Asp Pro Lys Lys Pro
        2515                2520                2525

Tyr Ala Pro Asp Lys Tyr Ile Gly Arg Arg Asn Pro Cys Glu Asn Arg
    2530                2535                2540

Glu Glu Asn Arg Phe Lys Val Asp Tyr Glu Trp Lys Cys Tyr Lys Asn
2545                2550                2555                2560

Ser Lys Phe Tyr Gln Glu Lys Lys Arg Val Cys Val Pro Pro Arg Arg
                2565                2570                2575

Glu His Met Cys Leu Arg Asn Leu Asp Glu Ile Lys Ile Glu Arg Leu
            2580                2585                2590

Lys Asp Ser Asn Tyr Leu Leu Lys Met Val Arg Arg Thr Ala Arg Asn
        2595                2600                2605

Glu Gly Ile Asp Ile Ile Lys Asn Phe Asn Ser Glu Asn Gly Cys Ala
    2610                2615                2620

Met Asn Pro Ile Cys Asp Thr Met Lys Tyr Ser Phe Ala Asp Leu Gly
2625                2630                2635                2640

Asp Ile Val Arg Gly Thr Asp Met Leu Arg Ile Gly Gly Tyr Leu Pro
                2645                2650                2655

Pro Val Glu Ile Lys Leu Tyr Lys Val Phe Glu Tyr Ile Tyr Gly Lys
            2660                2665                2670

Trp Arg Asn Lys Asn Lys Gly Arg Asn Lys Tyr Asn Asp Val Gln Thr
        2675                2680                2685

Phe Arg Ser Ala Trp Trp Asp Ala Asn Arg Lys Asp Ile Trp Lys Ala
    2690                2695                2700

Met Thr Cys Lys Ala Pro Glu Asp Ala Lys Leu Phe Arg Lys Gly Arg
2705                2710                2715                2720

Met Asp Gly Phe Glu Arg Ile Thr Leu Ile Gln Asp Lys Cys Gly His
                2725                2730                2735

Lys Asp Asp Pro Pro Val Asp Asp Tyr Ile Pro Gln Arg Phe Arg Trp
            2740                2745                2750

Met Thr Glu Trp Ser Glu Tyr Tyr Cys Lys Ala Leu Met Glu Glu Leu
        2755                2760                2765

Glu Lys Phe Lys Lys Ser Cys Asp His Cys Lys Thr Ser Asp Arg Cys
```

-continued

```
    2770                2775                2780

Lys Asn Asp Tyr Asp Glu Asn Lys Cys Glu Gln Cys Lys Thr Arg Cys
2785                2790                2795                2800

Gln Glu Tyr Lys Asn Phe Val Leu Lys Trp Lys Ser Leu Phe Asp Ile
                2805                2810                2815

Gln Ser Asn Lys Tyr Lys Glu Leu Tyr Glu Gln Pro Ile Tyr Thr Lys
            2820                2825                2830

Ile Ser Thr Tyr Asp His Val Gln Asn Phe Val Gln Lys Leu Lys Thr
        2835                2840                2845

Phe Lys Ser Glu Cys Ser Val Glu Ser Phe Ser Glu Tyr Leu His Glu
    2850                2855                2860

Thr Ser Lys Cys Leu Asn Tyr Lys Phe Asn Glu Asn Asp Gly Ser Ser
2865                2870                2875                2880

Asn Ile Arg Thr Tyr Ala Phe Glu Glu Thr Pro Lys Ser Tyr Lys Glu
                2885                2890                2895

Ala Cys Ser Cys Thr Leu Pro Ser Lys Asn Pro Leu Asp Asn Cys Pro
            2900                2905                2910

Thr Asp Gln Asn Lys Asp Gly Cys Lys Glu Leu Gln Thr Phe Thr Phe
        2915                2920                2925

Cys Ser Lys Asn Asp Tyr Asp Asn Asn Leu Asp Asn Trp Asn Ala Tyr
    2930                2935                2940

Leu Val Leu Asn Ser Ser Asp Asp Asn Lys Gly Val Leu Ile Pro Pro
2945                2950                2955                2960

Arg Arg Arg His Leu Cys Thr Arg Pro Ile Thr Ala Tyr Asn Tyr Arg
                2965                2970                2975

Lys Gly Asp Lys Glu Ile Leu Lys Lys Lys Leu Leu Thr Ser Ala Phe
            2980                2985                2990

Ser Gln Gly Gln Leu Leu Gly Gln Lys Tyr Lys Ser Glu Glu Glu Leu
        2995                3000                3005

Cys Phe Glu Ala Met Lys Tyr Ser Tyr Ala Asp Tyr Ser Asp Ile Ile
    3010                3015                3020

Lys Gly Thr Asp Met Met Asp Thr Ser Leu Ser Glu Lys Ile Lys Lys
3025                3030                3035                3040

Ile Phe Glu Thr Ser Asn Glu Ala Thr Glu Asn Arg Lys Thr Trp Trp
                3045                3050                3055

Glu Asn Asn Arg Arg Gln Ile Trp His Ala Met Leu Cys Gly Tyr Lys
            3060                3065                3070

Ile Ala Thr Ser Lys Val Thr Leu Asp Glu Gly Trp Cys Gln Leu Pro
        3075                3080                3085

Lys Asp Glu Glu Thr Asn Gln Phe Leu Arg Trp Leu Ile Glu Trp Ala
    3090                3095                3100

Lys Gln Ala Cys Lys Glu Lys Lys His Val Ser Asp Ser Leu Lys Thr
3105                3110                3115                3120

Lys Cys Pro Arg Ser Asn Glu Asp Asn Phe Glu Ala Ser Glu Leu Leu
                3125                3130                3135

Arg Gln Pro Gly Cys Gln Asn Asp Ile Arg Lys Tyr Ile Ser Leu Asn
            3140                3145                3150

Ile Leu Ile Lys Asn Thr Met Glu Asn Leu Asn Ile Lys Tyr Lys Gln
        3155                3160                3165

Leu Lys Asp Gln Ser Ser Gly Asn Ile Asp Asn Lys Pro Ser Glu Glu
    3170                3175                3180

Asn Val Gln Ser Tyr Ile Lys Ser Lys Asp Ser Gln Cys Ala Leu Glu
3185                3190                3195                3200
```

-continued

Leu Asn Asp Ile Asn Glu Ile Val Thr Gly Thr Lys Asn Asn Glu Asn
3205 3210 3215

Asn Glu Phe Lys Glu Val Leu Lys Lys Leu Tyr Pro Gly Leu Tyr Phe
3220 3225 3230

Val Glu Asp Glu Thr His Lys Asn His Val Leu Asp Gly Asn Ile Lys
3235 3240 3245

Glu Glu Glu Gln Thr Val Arg Pro Lys Ala Leu Tyr Phe Phe Thr Pro
3250 3255 3260

His Val Asp Ser Phe Tyr Gln Ala Pro Leu Phe Ser Thr His Arg Val
3265 3270 3275 3280

Ala Gln Tyr Asp Pro Lys Asn Asp Ile Leu Lys Ser Ser Ile Ser Val
3285 3290 3295

Val Ile Val Ser Ala Leu Gly Leu Ile Ala Leu His Phe Met Lys Lys
3300 3305 3310

Lys Phe Lys Ser Ser Val Asp Leu Leu Arg Ile Leu Asn Ile Pro Gln
3315 3320 3325

Gly Glu Tyr Gly Met Pro Thr Leu Glu Ser Lys Asn Arg Tyr Ile Pro
3330 3335 3340

Tyr Arg Ser Gly Pro Tyr Lys Gly Lys Thr Tyr Ile Tyr Met Glu Gly
3345 3350 3355 3360

Asp Thr Ser Gly Asp Glu Asp Lys Tyr Met Trp Asp Leu Ser Ser Ser
3365 3370 3375

Asp Ile Thr Ser Ser Glu Ser Glu Tyr Glu Glu Leu Asp Ile Asn Asp
3380 3385 3390

Ile Tyr Val Pro Gly Ser Pro Lys Tyr Lys Thr Leu Ile Glu Val Val
3395 3400 3405

Leu Glu Pro Ser Lys Arg Asp Ile Pro Ser Asp Asp Thr Pro Ser Asn
3410 3415 3420

Asp Thr Pro Arg Thr Asn Arg Phe Ile Asp Asp Glu Trp Asn Glu Leu
3425 3430 3435 3440

Lys His Asp Phe Val Ser Gln Tyr Leu Pro Asn Thr Glu Pro Asn Asn
3445 3450 3455

Asn Tyr Lys Ser Ala Asp Ile Pro Met Asn Thr Glu Pro Asn Thr Leu
3460 3465 3470

Tyr Ser Asp Asn Pro Glu Glu Lys Pro Phe Ile Ile Ser Ile His Asp
3475 3480 3485

Arg Asp Leu Tyr Thr Gly Lys Glu Ile Ser Tyr Asn Ile Asn Met Ser
3490 3495 3500

Thr Asn Thr Asn Asn Asp Ile Pro Met Asn Ala Arg Asn Asp Ser Tyr
3505 3510 3515 3520

Arg Gly Ile Asp Leu Ile Asn Asp Ser Leu Val Val Leu Asn Leu Leu
3525 3530 3535

Ile Tyr Met Met Lys Tyr
3540

<210> SEQ ID NO 3
<211> LENGTH: 32
<212> TYPE: PRT
<213> ORGANISM: Plasmodium fallciparum

<400> SEQUENCE: 3

Glu Ala Glu Lys Glu Leu Lys Glu Gly Lys Ile Pro Glu Gly Phe Lys
1 5 10 15

Arg Gln Met Phe Tyr Thr Phe Gly Asp Tyr Arg Asp Ile Leu Phe Gly

-continued 20 25 30

<210> SEQ ID NO 4
<211> LENGTH: 10
<212> TYPE: PRT
<213> ORGANISM: Plasmodium falciparum

<400> SEQUENCE: 4

Lys Glu Leu Lys Glu Gly Lys Ile Pro Glu
1 5 10

<210> SEQ ID NO 5
<211> LENGTH: 4
<212> TYPE: PRT
<213> ORGANISM: Plasmodium falciparum

<400> SEQUENCE: 5

Lys Glu Gly Lys
1

<210> SEQ ID NO 6
<211> LENGTH: 6
<212> TYPE: PRT
<213> ORGANISM: Plasmodium falciparum
<220> FEATURE:
<221> NAME/KEY: VARIANT
<222> LOCATION: (1)...(6)
<223> OTHER INFORMATION: misc_difference
<223> OTHER INFORMATION: Xaa = Any Amino Acid

<400> SEQUENCE: 6

Lys Xaa Asn Gly Xaa Asn
1 5

<210> SEQ ID NO 7
<211> LENGTH: 294
<212> TYPE: PRT
<213> ORGANISM: Plasmodium falciparum

<400> SEQUENCE: 7

Val Leu Gln Gln Lys Ser Asn Gly Ser Ile Asp Asn Cys Asn Ala Lys
1 5 10 15

Asn Arg Lys Lys Asn Glu Trp Gln Cys Asp Lys Asn Thr Phe Val Asp
20 25 30

Gly Asn Glu Gly Val Cys Met Pro Pro Arg Arg Lys Ser Ile Cys Ile
35 40 45

His Asn Leu Thr Leu Glu Glu Gln Thr Lys Asn Lys Tyr Gln Leu Arg
50 55 60

Glu Ala Phe Ile Lys Cys Ala Ala Lys Glu Thr Asn Leu Leu Trp Asp
65 70 75 80

Lys Tyr Lys Asn Asp Lys Asn Glu Ala Glu Glu Leu Leu Lys Lys Gly
85 90 95

Lys Ile Pro Glu Asp Phe Met Arg Ile Met Phe Tyr Thr Phe Gly Asp
100 105 110

Phe Arg Asp Phe Cys Leu Glu Asn Asp Met Gly Lys Asp Val Asp Lys
115 120 125

Val Lys Lys Asn Ile Asn Lys Val Phe Asn Asn Ser Ser Lys Arg Gly
130 135 140

Phe Lys Lys Ile Asp Pro Glu Asn Trp Trp Asn Glu Asn Gly Pro Gln
145 150 155 160

Ile Trp Asn Gly Met Leu Cys Ala Leu Ile His Ala Asp Thr Lys Asp

-continued

```
                165                 170                 175

Ser Ile Lys Asn Lys Asp Asn Tyr Lys Tyr Glu Lys Val Thr Ile Leu
            180                 185                 190

Ala Lys Arg Asp Gly Ser Asn Gly Met Thr Leu Ser Glu Phe Ala Lys
        195                 200                 205

Lys Pro Lys Phe Leu Arg Trp Phe Val Glu Trp Tyr Asp Asp Tyr Cys
    210                 215                 220

Lys Glu Arg Gln Lys Tyr Leu Thr Glu Val Ala Ser Thr Cys Lys Ser
225                 230                 235                 240

Ile Asp Gly Gly Gln Leu Lys Cys Asp Arg Gly Cys Asn Asn Lys Cys
                245                 250                 255

Asp Glu Tyr Lys Lys Tyr Met Arg Lys Lys Lys Glu Glu Trp Asn Leu
            260                 265                 270

Gln Asp Lys Tyr Tyr Lys Asp Lys Arg Glu Asn Lys Gly Ile Asp Lys
        275                 280                 285

Gly Pro Ile Gly Ile Ile
    290


<210> SEQ ID NO 8
<211> LENGTH: 407
<212> TYPE: PRT
<213> ORGANISM: Plasmodium falciparum

<400> SEQUENCE: 8

Asn Gly Gln Asp Gly Thr Lys Lys Ile Glu Glu Cys Asn Thr Lys Tyr
 1               5                  10                  15

Tyr Pro Thr Lys Asn Asp Tyr Pro Gly Trp Asn Cys Thr Asp Lys Val
            20                  25                  30

Ile Asn Arg Glu Glu Gly Ser Cys Met Pro Pro Arg Arg Gln Lys Leu
        35                  40                  45

Cys Ile His Asn Leu Glu His Leu Ser Glu Lys Ala Thr Glu Thr Glu
    50                  55                  60

Leu Arg Lys Ala Phe Ile Glu Cys Ala Ala Ile Glu Thr Phe Trp Leu
65                  70                  75                  80

Trp Asp Lys Tyr Lys Glu Asp Lys Lys Asp Glu Lys Lys Thr Glu Gly
                85                  90                  95

Gly Gly Ile Ser Asp Asp Pro Asp Asp Pro Gln Lys Lys Leu Glu Gly
            100                 105                 110

Gly Thr Ile Pro Glu Asp Phe Lys Arg Gln Met Phe Tyr Thr Tyr Gly
        115                 120                 125

Asp Tyr Arg Asp Phe Leu Phe Gly Thr Asp Ile Ser Lys Gly His Gly
    130                 135                 140

Lys Glu Ser Ala Leu Gly Lys Lys Ile Asp Ser Leu Phe Lys Asn Gly
145                 150                 155                 160

Asp Gln Lys Ser Pro Ser Gly Lys Thr Pro Thr Glu Trp Trp Asn Asp
                165                 170                 175

Tyr Gly Pro Asp Ile Trp Lys Gly Met Val Cys Gly Leu Ser His His
            180                 185                 190

Ile Lys Asn Gly Asn Lys Glu Gln Leu Arg Lys Asn Leu Thr Asp Asn
        195                 200                 205

Asn Lys Tyr Thr Lys Ile Ser Ser Lys Leu Glu Asp Phe Ala Ser Arg
    210                 215                 220

Pro Gln Phe Leu Arg Trp Phe Ile Glu Trp Gly Asp Gln Phe Cys Arg
225                 230                 235                 240
```

-continued

```
Glu Arg Val Val Lys Ile Asn Gln Leu Lys Thr Gly Cys Asn Glu Tyr
                245                 250                 255

Glu Cys Gly Ser Gln Glu Asn Gly Lys Lys Glu Ala Cys Lys Asn Ala
            260                 265                 270

Cys Glu Ala Tyr Lys Ser Trp Leu Lys Asp Trp Lys Asp Gln Tyr Glu
        275                 280                 285

Gln Gln Thr Ala Lys Phe Asp Lys Asp Lys Lys Asp Lys Lys Phe Asp
    290                 295                 300

Gly Thr Ser Ala Glu Val Asp Val Ala Ala Val Ser Ser Val His Glu
305                 310                 315                 320

Tyr Leu Gln Glu Glu Leu Lys Asn Leu Cys Thr Lys Gly Asp Cys Ala
                325                 330                 335

Cys Met Glu Lys Pro Ser Ala Gln Asp Glu Glu Thr Glu Leu Leu Gly
            340                 345                 350

Gly Asn Tyr Phe Pro Glu Ala Met Asp Tyr Pro Pro Lys Glu Ile Gly
        355                 360                 365

Glu Arg Cys Lys Cys Ala Ile Pro Ser Glu Pro Met Ser Cys Val Glu
    370                 375                 380

Gln Ile Ala Lys His Leu Arg Glu Lys Ala Glu Lys Asn Val Lys Ile
385                 390                 395                 400

Tyr Glu Ser Ser Leu Lys Gly
                405


<210> SEQ ID NO 9
<211> LENGTH: 351
<212> TYPE: PRT
<213> ORGANISM: Plasmodium falciparum

<400> SEQUENCE: 9

Pro Cys Lys Met Val Gln Lys Leu Ile Ser Glu Gln Ile Glu Lys Asn
 1               5                  10                  15

Asn Ile His Asn Cys Lys Lys Thr Glu Asp Ala Lys Trp Lys Cys Glu
            20                  25                  30

Asn Thr Lys Leu Gly Glu Asp Glu Gly Val Cys Met Pro Pro Arg Arg
        35                  40                  45

Gln Asn Leu Cys Val His Tyr Leu Thr Lys Leu Asn Asp Asp Ser Lys
    50                  55                  60

Glu Glu Asp Leu Arg Glu Ala Phe Ile Lys Ser Ala Ala Ala Glu Thr
65                  70                  75                  80

Phe Leu Leu Arg Gln Tyr Tyr Asn Ser Lys Asn Val Glu Asp Asp Lys
                85                  90                  95

Ile Leu His Arg Asp Met Ile Pro Pro Glu Phe Phe Arg Ser Met Phe
            100                 105                 110

Tyr Thr Phe Gly Asp Tyr Arg Asp Ile Cys Leu Asp Thr Asp Ile Ser
        115                 120                 125

Glu Lys Ile Ala Asp His Asp Val Thr Thr Ala Lys Lys Lys Ile Thr
    130                 135                 140

Ala Val Phe Gln Lys Ile Gly Ser Lys Thr Thr Asn Gly Lys Lys Val
145                 150                 155                 160

Leu Glu Arg Glu Gly Trp Trp Lys Glu Tyr Gly Leu Ser Ile Trp Lys
                165                 170                 175

Gly Met Leu Cys Ala Leu Ser Tyr Asn Thr Glu Thr Lys Lys Met Asp
            180                 185                 190

Glu Gly Val Arg Thr Tyr Leu Met Lys Tyr Ile Tyr Lys Asn Asn Asp
        195                 200                 205
```

-continued

```
Ile Lys Glu Tyr Leu Glu Glu Phe Ala Ser Arg Pro Pro Phe Leu Arg
    210                 215                 220

Trp Val Thr Glu Trp Gly Glu Asp Phe Val Lys Asn Arg Lys Lys Glu
225                 230                 235                 240

Leu Val Ser Leu Lys Lys Lys Cys Asp Ser Cys Thr Leu Arg Asn Asn
                245                 250                 255

Gly Thr Ser Asn Lys Thr Cys Asp Asp Asn Glu Asn Cys Gly Ala Cys
            260                 265                 270

Lys Thr Gln Cys Glu Lys Tyr Lys Lys Trp Met Glu Arg Trp Lys Lys
        275                 280                 285

His Tyr Ser Ser Gln Lys Lys Lys Phe Gln Leu Tyr Lys Asn Ser Ala
    290                 295                 300

Thr Tyr Asn Asn Gly Leu Ala Val Lys Glu Ala Asn Ser Glu Thr Tyr
305                 310                 315                 320

Lys Asn Asp Pro Glu Val Thr Glu Ala Asn Ser Ala Lys His Ala Arg
                325                 330                 335

Asp Tyr Leu Lys Thr Gln Leu Glu Asn Met Ile Cys Thr Asn Gly
            340                 345                 350


<210> SEQ ID NO 10
<211> LENGTH: 311
<212> TYPE: PRT
<213> ORGANISM: Plasmodium falciparum

<400> SEQUENCE: 10

Glu Thr Asp Asp Ile Asp Gly Cys Asn Gln Lys Tyr Lys Ala Gly Lys
 1               5                  10                  15

Asp Lys Tyr Pro Gly Trp Asp Cys Asn Ser Gln Ile His Thr Thr His
            20                  25                  30

Asn Gly Ala Cys Met Pro Pro Arg Arg Gln Lys Leu Cys Val Ser Gly
        35                  40                  45

Leu Thr Lys Thr Asp Arg Ile Lys Ala Ile Glu Tyr Ile Arg Thr Glu
    50                  55                  60

Phe Ile Lys Ser Ala Ala Ile Glu Thr His Phe Ala Trp Asp Arg Tyr
65                  70                  75                  80

Lys Glu Asp Asn Gly Glu Ala Glu Ala Glu Leu Lys Asn Gly Asn Ile
                85                  90                  95

Pro Glu Gly Phe Lys Arg Gln Met Tyr Tyr Thr Phe Gly Asp Tyr Arg
            100                 105                 110

Asp Ile Phe Phe Gly Arg Asp Ile Ser Thr His Ala Tyr Ile Ser Gly
        115                 120                 125

Val Ser Pro Lys Val Ile Thr Ile Leu Glu Lys Glu Asn Asp Ala Lys
    130                 135                 140

Tyr Ala Ala Lys Gln Asn Ser Asn Asn Glu Leu Leu Asp Asp Trp Trp
145                 150                 155                 160

Asp Gln His Gly Lys Asp Ile Trp Glu Gly Met Leu Cys Ala Leu Thr
                165                 170                 175

His Lys Ile Ser Asp Glu Glu Lys Lys Lys Glu Ile Lys Asn Lys Tyr
            180                 185                 190

Ser Tyr Lys Lys Leu Asn Glu Ser Pro Lys Gly Ser Asn Lys Val Glu
        195                 200                 205

Asp Phe Ala Lys Lys Pro Gln Phe Leu Arg Trp Phe Ile Glu Trp Gly
    210                 215                 220

Asp Glu Phe Cys Ala Gln Arg Glu Glu Lys Glu Ala Lys Val Lys Val
```

-continued

```
225                 230                 235                 240

Ser Cys Ser Asp Ala Lys Asp Tyr Asp Gly Cys Lys Asn Thr Lys Ser
                245                 250                 255

Asn Ala Ser Cys Val Ser Ala Cys Lys Val Tyr Glu Asp Tyr Ile Thr
            260                 265                 270

Lys Lys Lys Val Glu Tyr Thr Lys Gln Lys Gly Lys Phe Asp Ala Glu
        275                 280                 285

Lys Ile Thr Asp Lys Glu Gly Tyr Glu Gly Phe Ser Thr Lys Asp Ala
    290                 295                 300

Ser Glu Tyr Leu Lys Lys Lys
305                 310


<210> SEQ ID NO 11
<211> LENGTH: 308
<212> TYPE: PRT
<213> ORGANISM: Plasmodium falciparum

<400> SEQUENCE: 11

Gly Asn Asp Gly Ser Asn Glu Ile Ser Gly Cys Asn Pro Lys Glu Ser
 1               5                  10                  15

Tyr Pro Asp Trp Asp Cys Lys Lys Asn Ile Asp Asn Ser His Ser Gly
            20                  25                  30

Ala Cys Met Pro Pro Arg Arg Gln Lys Leu Cys Val Arg Asp Leu Thr
        35                  40                  45

Gln Gly Gly Glu Ile Arg Lys Pro Glu Asp Ile Leu Thr Lys Phe Ile
    50                  55                  60

Asn Cys Ala Ala Lys Glu Thr His Phe Ala Trp His Lys Tyr Lys Lys
65                  70                  75                  80

Asp Asn Val Asn Ala Glu Asn Glu Leu Lys Ser Gly Lys Ile Pro Glu
                85                  90                  95

Gly Phe Arg Lys Gln Met Tyr Tyr Thr Phe Gly Asp Phe Arg Asp Ile
            100                 105                 110

Phe Phe Gly Thr Asp Ile Ser Ser Cys Arg Tyr Ile Lys Asp Thr Ser
        115                 120                 125

Gln Thr Ile Lys Ser Lys Leu Gly Asp Gln Ala Thr Thr Glu Lys Gly
    130                 135                 140

Asp Thr His Ile Asp Asp Asn Lys Lys Leu Gln Glu Trp Trp Thr Ile
145                 150                 155                 160

His Gly Pro Lys Ile Trp Glu Gly Met Leu Cys Ala Leu Thr Asn Gly
                165                 170                 175

Leu Ser Glu Ser Glu Lys Lys Asn Ile Leu Gln Asp Tyr Ser Tyr Asn
            180                 185                 190

Lys Leu Asn Asn Ala Glu Lys Asp Asp Cys Cys Leu Glu Lys Phe Ala
        195                 200                 205

Ser Lys Pro Gln Phe Leu Arg Trp Tyr Val Glu Trp Ser Asp Glu Phe
    210                 215                 220

Cys Arg Glu Arg Lys Lys Leu Glu Asp Lys Val Glu Asp Val Cys Ile
225                 230                 235                 240

Lys Ala Lys Asp Tyr Glu Gly Cys Lys Asn Asn Lys Ser Asn Asn Ser
                245                 250                 255

Cys Val Lys Val Cys Lys Glu Tyr Glu Asn Tyr Ile Thr Gly Lys Lys
            260                 265                 270

Thr Gln Tyr Glu Ser Gln Glu Gly Lys Phe Asn Thr Glu Lys Arg Gln
        275                 280                 285
```

-continued

```
Lys Lys Pro Glu Tyr Asn Ser Tyr Ser Lys Lys Asp Ala Ser Glu Tyr
    290                 295                 300

Leu Lys Asp Lys
305
```

IDENTIFICATION OF THE DOMAIN OF *PLASMODIUM FALCIPARUM* ERYTHROCYTE MEMBRANE PROTEIN 1 (PFEMP1) THAT MEDIATES ADHESION TO CHONDROITIN SULFATE A

CROSS-REFERENCE TO RELATED APPLICATIONS

This application is a continuation of international application number PCT/US00/24195, and claims the benefit of priority of international application number PCT/US00/24195 having international filing date of Sep. 1, 2000, designating the United States of America and published in English, which claims the benefit of priority of U.S. provisional patent application No. 60/152,023, filed Sep. 1, 1999; both of which are hereby expressly incorporated by reference in their entireties.

FIELD OF THE INVENTION

The present invention relates to the discovery of a var gene and corresponding protein that modulates adhesion of parasitized red blood cells to chondroitin sulfate A. Novel biological tools, prophylactics, therapeutics, diagnostics, and methods of use of the foregoing are also disclosed.

BACKGROUND OF THE INVENTION

*Plasmodium falciparum* malaria is more severe in pregnant women, especially during the first pregnancy (primigravida), and causes disease in the mother and fetal death even in those women who were previously immune. (Steketee, et al., *Am J Trop Med Hyg* 55, 2–7 (1996)). In the primigravida, massive numbers of parasitized red blood cells (PRBCs) sequester in the maternal circulation of the placenta, binding to chondroitin sulfate A (CSA). (Fried & Duffy, *Science* 272, 1502–1504 (1996)). Antibodies that develop after multiple pregnancies are associated with reduced PRBCs in the placenta and block CSA-binding of PRBCs. (Fried, et al., *Nature* 395, 851–2 (1998)).

Members of the recently described var gene family and their expressed proteins, *Plasmodium falciparum* Erythrocyte Membrane Protein-I (PfEMP1), mediate PRBCs binding to several adhesion receptors such as CD36, intercellular adhesion molecule-1 (ICAM-1), and chondroitin sulfate A (CSA). (Baruch, et al., *Cell* 82, 77–87 (1995), (Smith, et al., *Cell* 82, 101–10 (1995), (Su, et al., *Cell* 82, 89–100 (1995), and (Scherf, et al., *Embo J* 17, 5418–5426 (1998)). Recent work on var gene switching has established that transcription of a particular var gene (termed "FCR3.varCSA") in parasites selected for binding to CSA but not in parasites selected for adhesion to CD36 or ICAM-1. (Scherf, et al., *Embo J* 17, 5418–5426 (1998)). Thus, var genes adhere dichotomously either to CD36 and other receptors on endothelium or to CSA in placenta and not to CD36.

Potential receptor domains in var genes include Duffy binding like (DBL) domains, named for their homology to the Duffy binding domain of *P. vivax* (Su, et al., *Cell* 82, 89–100 (1995)), and cysteine-rich interdomain regions (CIDR). The CIDR1 domain, located after the first DBL, was shown to mediate PRBCs adhesion to CD36. (Baruch, et al., *Cell* 82, 77–87 (1995) and (Baruch, et al., *Blood* 90, 3766–75 (1997)). DBL1 has been identified as a receptor for binding PRBCs to uninfected RBCs in var genes from PRBCs that rosette normal RBCs. (Rowe, et al., *Nature* 388, 292–5 (1997) and (Chen, et al., *J Exp Med* 187, 15–23 (1998)). Although antibodies directed to two different domains of a var gene expressed in CSA-binding parasites reduced binding to CSA (Reeder, et al., *Proc Natl Acad Sci USA* 96, 5198–202 (1999)), the gene, protein and domains thereof that bind CSA have not been identified.

BRIEF SUMMARY OF THE INVENTION

The invention described herein concerns the discovery of molecules that are intimately involved in PRBC binding, sequestration, and the onset of maternal malaria. One such molecule is the product: of the FCR3.varCSA gene, a 3,542-amino acid polypeptide called the FCR3.varCSA protein, which binds to CSA. Other molecules that mediate PRBC binding, sequestration, and the onset of maternal malaria include fragments of the FCR3.varCSA protein (e.g., polypeptides that comprise the CIDR1 and/or the DBL3 domains or portions thereof) and other varCSA proteins and fragments thereof including, but not limited to polypeptides having the A4 tres DBL3-γ and ItG2-CS2 DBL2-γ (SEQ. ID. Nos: 9 and 11, respectively) sequence. Furthermore, nucleic acids encoding these molecules can be used to modulate PRBC binding, sequestration, and the onset of maternal malaria.

The FCR3.varCSA gene was cloned and sequenced in its entirety and the FCR3.varCSA protein is predicted to have eight receptor-like domains. To further characterize the FCR3.varCSA-CSA complex, several adhesion assays (referred to as "varCSA characterization assays" or "FCR3.varCSA characterization assays) were performed. In some experiments, proteins encompassing various domains of FCR3.varCSA or other varCSA polypeptides were expressed on the surface of CHO cells and adhesion to various ligands was analyzed. From these characterization assays it was discovered that two Duffy-binding-like (DBL) domains (DBL3 and DBL7) of FCR3.varCSA were involved in adhesion to CSA. Further, it was found that DBL7, but not DBL3, bound chondroitin sulfate C (CSC), a negatively charged sugar that does not support PRBC adhesion. Competitive binding experiments employing exogenously added CSA prevented the interaction with DBL3, however, either competitor (i.e., exogenously added CSA or CSC) prevented adhesion to DBL7. Thus, evidence is provided herein that the DBL3 and/or CIDR1 domain of FCR3.varCSA are intimately involved in PRBC binding, sequestration, and the onset of maternal malaria.

Many different forms of var genes exist due to gene switching and it was believed that some of these gene products and fragments thereof also specifically bind CSA. To verify this hypothesis, several adhesion assays were conducted using CHO cells that cell-surface-express polypeptides having various types of varCSA domains. These experiments revealed that some domains of other varCSA molecules effectively bound CSA (e.g., A4 tres DBL3-γ (SEQ. ID. No.: 9) and ItG2-CS2 DBL2-γ (SEQ. ID. No.: 11)) while others (e.g., R29 DBL2-γ (SEQ. ID. NO.: 7), A4 DBL4-γ (SEQ. ID. No.: 8), and FCR3 var3 DBL-γ (SEQ. ID. No.: 10) did not.

Several embodiments concern the interaction of FCR3.varCSA with CSA, the formation of a FCR3.varCSA-CSA complex, PRBC binding, sequestration, and the onset of maternal malaria. For example, embodiments include the FCR3.varCSA-CSA complex, FCR3.varCSA protein, fragments of FCR3.varCSA protein (e.g., DBL3 and CIDR1), nucleic acids encoding these polypeptides, cells that have these nucleic acids, cells that express these polypeptides, antibodies that recognize these polypeptides, and software and hardware that have nucleotide or polypeptide information or protein modeling information corresponding to these sequences, as well as, data from FCR3.varCSA characterization assays and diagnostic profiles.

Other embodiments concern the interaction of other varCSA molecules including, but not limited to, varCSA molecules having the A4 tres DBL3-γ (SEQ. ID. No.: 9) and ItG2-CS2 DBL2-γ (SEQ. ID. No.: 11) sequences, with CSA and the formation of a varCSA-CSA complex. For example, embodiments include a varCSA-CSA complex, fragments of a varCSA protein (e.g., A4 tres DBL3-γ (SEQ. ID. No.: 9) and ItG2-CS2 DBL2-γ (SEQ. ID. No.: 11), nucleic acids encoding these polypeptides, cells that have these nucleic acids, cells that express these polypeptides, antibodies that recognize these polypeptides, and software and hardware that have nucleotide or polypeptide information or protein modeling information corresponding to these sequences, as well as, data from varCSA characterization assays and diagnostic profiles.

Additionally, nucleic acids that complement nucleic acids encoding FCR3.varCSA or fragments of FCR3.varCSA or other varCSA molecules that bind CSA (e.g., A4 tres DBL3-γ (SEQ. ID. No.: 9) and ItG2-CS2 DBL2-γ (SEQ. ID. No.: 11) and cells that have these sequences are embodiments. Another aspect of the invention includes the use of therapeutic or prophylactic agents (e.g., FCR3.varCSA or fragments of FCR3.varCSA, A4 tres DBL3-γ (SEQ. ID. No.: 9) and ItG2-CS2 DBL2-γ (SEQ. ID. No.: 11) or nucleic acids encoding these compositions) to modulate adhesion to CSA and/or to generate an immune response in a patient. Further, methods of discovering such agents including approaches in rational drug design and combinatorial chemistry are also embodiments.

Other embodiments include biotechnological tools, diagnostic assays, diagnostic kits, and methods of use of the foregoing. For example, multimeric and multimerized FCR3.varCSA, fragments of FCR3.varCSA, A4 tres DBL3-γ, and ItG2-CS2 DBL2-γ and nucleic acids encoding these sequences or complementary sequences are used as biotechnological tools or diagnostic reagents. Diagnostic assays preferably measure the concentration or expression level of FCR3.varCSA or nucleic acid encoding FCR3.varCSA in tested subjects and compare these values to those obtained from healthy individuals or individuals that are infected with *Plasmodium falciparum* (FCR3.varCSA disease-state profiles). Additionally, some diagnostic assay embodiments measure the concentration or expression level of proteins or polypeptides comprising the A4 tres DBL3-γ and ItG2-CS2 DBL2-γ fragments or nucleic acids encoding these molecules in tested subjects and compare these values to those obtained from healthy individuals or individuals that are infected with *Plasmodium falciparum*. These varCSA diseases-state profiles (,an be recorded on software and hardware and can be used to analyze disease-state profiles of tested subjects so as to identify the presence or prevalence of maternal malaria or progress of a treatment for maternal malaria. Desirably, measurements of the concentration or expression level of the varCSA proteins or polypeptides or nucleic acids encoding these molecules are made from blood. These disease-state profiles are invaluable tools for the prognosis, diagnosis, and treatment of FCR3.varCSA-related diseases, including, but not limited to, maternal malaria.

Pharmaceuticals having FCR3.varCSA or fragments of FCR3.varCSA (e.g., DBL3 and/or CIDR1) or nucleic acids encoding these polypeptides or antibodies that recognize these molecules or agents that otherwise interact with FCR3.varCSA are also embodiments. The pharmaceutical embodiments may also comprise polypeptides having the A4 tres DBL3-γ and ItG2-CS2 DBL2-γ sequence or nucleic acids encoding these molecules. The pharmaceuticals described herein can also include carriers and other agents that promote delivery of the active ingredients.

Further, methods of treatment and prevention of malaria, specifically maternal malaria, are provided. Some methods of treatment and prevention of maternal malaria, involve identifying a subject in need of an agent that inhibits the association of a varCSA molecule (e.g., FCR3.varCSA) with CSA and administering to said subject a therapeutically effective dose of an agent that either inhibits adhesion of the varCSA molecule to CSA and/or promotes an immune response in a patient. Other methods involve identifying a patient in need of an agent that inhibits PRBC binding, sequestration, or the onset of maternal malaria and administering to said patient a composition comprising the CIDR1 domain or fragment thereof or an antibody that recognizes a CIDR1 domain. Preferably, this composition is derived from FCR3.varCSA in that it comprises a CIDR1 domain or antibody thereto or fragment thereof that is derived from FCR3.varCSA.

DETAILED DESCRIPTION OF INVENTION

Figure 1A:
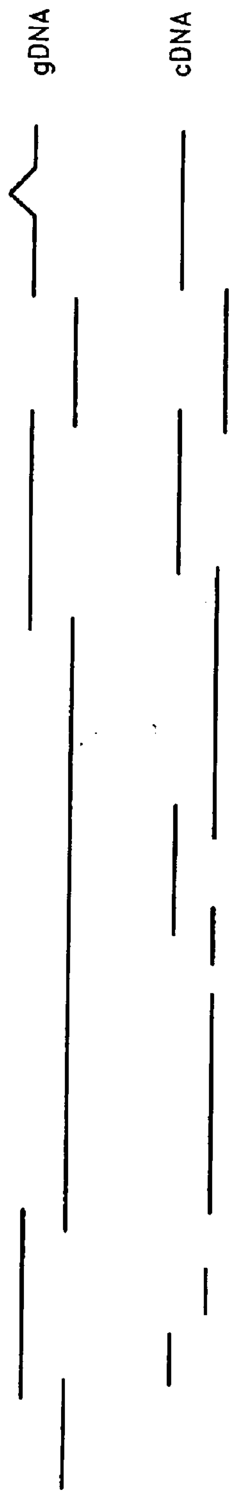
FIG. 1 (A) Overlapping clones of the FCR3.varCSA gene were isolated from genomic FCR3-CSA parasites and sequenced (gDNA). Regions amplified by RT-PCR (cDNA) from FCR3-CSA trophozoite mRNA confirm that the genomic FCR3.varCSA gene sequence is contiguous with the exception of the intron region. (B) Schematic domain organization of the FCR3.varCSA gene. An unusually small intron of 230 bp separates exon 1 and exon 2 of the FCR3.varCSA gene. The amino acid boundaries of the different DBL (Duffy Binding Like) and CIDR1 (Cysteine-rich Interdomain Region) domains are indicated. (C) Domain regions that were expressed on the surface of CHO-745 cells showing their amino acid boundaries.

Several molecules that mediate PRBC binding, sequestration, and the onset of maternal malaria have been discovered. One such molecule is the product of the FCR3.varCSA gene, a 3,542-amino acid polypeptide called the FCR3.varCSA protein. Other molecules include fragments of the FCR3.varCSA protein (e.g., DBL3 and/or CIDR1) and other varCSA proteins and fragments thereof including, but not limited to, polypeptides having the A4 tres DBL3-γ and ItG2-CS2 DBL2-γ (SEQ. ID. Nos: 9 and 11, respectively) sequence. The adhesion of *Plasmodium falciparum* infected red blood cells, also referred to as "parasitized red blood cells (PRBCs), to chondroitin sulfate A (CSA) is intimately involved in sequestration of *P. falciparum*, and the manifestation of maternal malaria. Thus, many of the embodiments described herein can be used as biological tools, therapeutics, prophylactics, and diagnostics for the study, treatment and prevention of maternal malaria.

Embodiments of the invention include software and hardware comprising nucleic acid sequences encoding FCR3.varCSA or fragments thereof (e.g., nucleic acids encoding molecules that comprise DBL3 and/or CIDR1) or complements of these sequences and protein sequences corresponding to FCR3.varCSA and fragments of FCR3.varCSA (e.g., DBL3 and/or CIDR1). Preferred software and hardware have nucleic acid sequences that encode fragments of FCR3.varCSA that bind to chondroitin sulfate A (e.g., DBL3 and/or CIDR1) or amino acid sequences that correspond to regions of a var protein that bind CSA. Additionally, the software and hardware of the invention include embodiments that provide disease-state profiles that have information such as concentrations and expression levels of FCR3.varCSA (e.g., mRNA) or FCR3.varCSA detected in biological samples from healthy subjects, as well as, subjects suffering from malaria. The software and hardware embodiments of the invention are also used to further characterize FCR3.varCSA (e.g., to develop protein models of FCR3.varCSA, to identify homologous proteins, and to identify agents that interact with FCR3.varCSA) and to provide diagnostic and prognostic information that allows for the determination of the disease state of a tested individual.

Nucleic acids encoding full-length FCR3.varCSA or nucleic acids encoding fragments of FCR3.varCSA (e.g., DBL3 and/or CIDR1) are embodiments of the invention. Preferred nucleic acid embodiments include nucleic acids encoding fragments of FCR3.varCSA that bind to CSA (e.g., DBL3) or otherwise mediate PRBC binding, sequestration, and the onset of maternal malaria (e.g., CIDR1). Additionally, the nucleic acid embodiments of the invention include nucleic acids or derivatives thereof that are complementary to fall-length FCR3.varCSA or fragments of FCR3.varCSA (e.g., antisense oligonucleotides and ribozymes). Preferred complementary nucleic acids of the invention include nucleic acids or derivatives thereof that are complementary to fragments of FCR3.varCSA that have a nucleotide sequence that encodes a polypeptide that binds to CSA (e.g., DBL3) or otherwise mediates PRBC binding, sequestration, and the onset of maternal malaria (e.g., CIDR1). The nucleic acid embodiments can be manufactured as monomeric, multimeric, and multimerized agents. The nucleic acid embodiments also include vectors, plasmids, and recombinant constructs having nucleic acids encoding full-length FCR3.varCSA or fragments of FCR3.varCSA. Additional embodiments are vectors, plasmids, and recombinant constructs having nucleic acids complementary to the full-length FCR3.varCSA or fragments of FCR3.varCSA. Cells having the nucleic acid embodiments described herein, including cells in animals having a nucleic acid embodiment created by genetic engineering (e.g., cells in a transgenic animal or an oocyte), are within the scope of aspects of the invention.

The nucleic acid embodiments also include nucleic acids encoding fragments of other varCSA proteins that bind CSA. For example, some embodiments concern nucleic acids that encode polypeptides comprising the A4 tres DBL3-γ and ItG2-CS2 DBL2-γ (SEQ. ID. Nos: 9 and 11, respectively) sequence or complements thereto. These nucleic acid embodiments can be manufactured as monomeric, multimeric, and multimerized agents and can be cloned into vectors, plasmids, and recombinant constructs. Furthermore, cells having nucleic acids that encode polypeptides comprising the A4 tres DBL3-γ and ItG2-CS2 DBL2-γ (SEQ. ID. Nos: 9 and 11, respectively) sequence or complements thereto, including cells in animals having a nucleic acid embodiment created by genetic engineering (e.g., cells in a transgenic animal or an oocyte), are embodiments.

Protein-based embodiments include full-length FCR3.varCSA or fragments of FCR3.varCSA. Preferred protein-based embodiments include fragments of FCR3.varCSA that have an amino acid sequence that encode a polypeptide that binds to CSA (e.g., DBL3) or otherwise mediates PRBC binding, sequestration, and the onset of maternal malaria (e.g., CIDR1). Additionally, the protein-based embodiments include protein derivatives or modifications of FCR3.varCSA or fragments of FCR3.varCSA including, but not limited to peptidomimetics. The protein-based embodiments can be manufactured as monomeric, multimeric, and multimerized agents. Cells having the protein-based embodiments, including cells in animals having a protein-based manufacture of the present invention ((e.g., cells in a transgenic animal or an oocyte), are within the scope of aspects of the invention.

In some embodiments, the polypeptides described herein are used to generate antibodies. Preferred embodiments include polyclonal and monoclonal antibodies that recognize epitopes corresponding to regions of FCR3.varCSA (e.g., DBL3 and CIDR1). These antibodies have application in biological assays, therapeutics, and can be used to diagnose human disease by identifying the presence of FCR3.varCSA in a biological sample.

The protein-based embodiments also include other varCSA proteins and fragments thereof that bind CSA. For example, some embodiments concern polypeptides comprising the A4 tres DBL3-γ and ItG2-CS2 DBL2-γ (SEQ. ID. Nos: 9 and 11, respectively) sequence. As above, these embodiments can be manufactured as monomeric, multimeric, and multimerized agents. Embodiments also include cells having polypeptides comprising the A4 tres DBL3-γ and ItG2-CS2 DBL2-γ (SEQ. ID. Nos: 9 and 11, respectively) sequence, including cells in animals (e.g., cells in a transgenic animal or an oocyte). In some embodiments, these polypeptides are used to generate monoclonal and/or polyclonal antibodies, which have diagnostic and therapeutic application.

Several types of assays that provide information about a particular varCSA molecule (e.g., FCR3.varCSA) or the formation of a particular varCSA-CSA complex (e.g., FCR3.varCSA-CSA complex are embodiments. These assays are collectively referred to as "FCR3.varCSA characterization assays" or "varCSA characterization assays". One type of varCSA characterization assay concerns measuring the ability of FCR3.varCSA or fragments thereof to bind to CSA or fragments of CSA. For example, methods of performing characterization assays are provided, in which CSA or FCR3.varCSA is disposed on a support and is subsequently contacted with a ligand (e.g., FCR3.varCSA, or CSA, depending on the support-bound molecule) and FCR3.varCSA-mediated adhesion is determined. A similar binding assay can be employed in the presence of an inhibiting or enhancing molecule (a "modulator") such as a peptide or peptidomimetic (collectively referred to as a "peptide agent") or a chemical. The supports in these assays can be conventional resins, plastics, lipids, and cells. Thus, in some FCR3.varCSA characterization assays cells having FCR3.varCSA or a fragment thereof at the cell membrane (e.g., accomplished by transfection or liposome transfer) are used to identify agents that interfere with FCR3.varCSA mediated adhesion.

In some aspects, the modulation of FCR3.varCSA-mediated adhesion is accomplished by using a modulator that is a nucleic acid embodiment. For example, a construct encoding FCR3.varCSA is transfected into cells so as to raise the concentration of FCR3.varCSA and thereby promote FCR3.varCSA-mediated adhesion to CSA or, alternatively, a construct encoding a nucleic acid that is complementary to a nucleic acid encoding FCR3.varCSA (e.g., an antisense inhibitor or a ribozyme) is used to reduce the concentration of FCR3.varCSA and thereby inhibit FCR3.varCSA-mediated adhesion to CSA. Further, in some embodiments, nucleic acids encoding wild-type or mutant FCR3.varCSA or fragments of FCR3.varCSA or complements thereof are transfected and expressed in cells so as to modulate FCR3.varCSA-mediated adhesion or to induce an immune response or both.

According to other aspects, the modulation of FCR3.varCSA-mediated adhesion is achieved by using a modulator that is a protein-based embodiment. For example, FCR3.varCSA is delivered to cells by liposome-mediated transfer so as to raise the intracellular concentration of FCR3.varCSA and thereby promote FCR3.varCSA-mediated adhesion to CSA or, alternatively, wild-type or mutant FCR3.varCSA or fragments of FCR3.varCSA (e.g., DBL3 and/or CIDR1) are delivered to cells by liposome-mediated transfer so as to inhibit FCR3.varCSA-mediated adhesion to CSA or to induce an immune response or both. Peptidomimetics that resemble FCR3.varCSA or fragments thereof (e.g., DBL3 and/or CIDR1) are also modulators of the invention and can be used to effect FCR3.varCSA mediated adhesion or to induce an immune response or both. Many chemicals clan also be modulators and can be identified by their ability to effect FCR3.varCSA mediated adhesion using the FCR3.varCSA characterization assays and teachings herein.

Approaches in rational drug design can be employed, for example, to identify novel agents that interact with FCR3.varCSA so as to modulate FCR3.varCSA-mediated adhesion or that can be used to induce an immune response in a patient. In these embodiments, protein models of FCR3.varCSA, fragments of FCR3.varCSA, and agents that interact with FCR3.varCSA or fragments of FCR3.varCSA are constructed and approaches in combinatorial chemistry are used to develop agents that modulate FCR3.varCSA-mediated adhesion to CSA or induce an immune response. Accordingly, novel agents that interact with FCR3.varCSA are developed, screened in a FCR3.varCSA characterization assay (e.g., a FCR3.varCSA adhesion assay), and the identity of each agent and its performance in a FCR3.varCSA characterization assay, its effect on the modulation FCR3.varCSA-mediated adhesion to CSA or its ability to induce an immune response is recorded on software or hardware. The recorded data can be used to create a library of FCR3.varCSA modulating agents. These libraries can be employed to identify more agents that modulate FCR3.varCSA-mediated adhesion to CSA and are valuable clinical tool, for manufacturing and selecting an appropriate pharmaceutical to treat a particular type of *Plasmodium*.

The nucleic acid and protein-based embodiments described herein can also be used as biotechnological tools and probes in diagnostic assays. In some aspects, for example, the nucleic acid embodiments are employed as nucleic acid probes in hybridization assays, cloning, or as primers for Polymerase Chain Reaction (PCR). Similarly, the protein-based embodiments can be used, for example, to characterize FCR3.varCSA or other varCSA molecules that bind CSA, identify related proteins, and study varCSA-mediated adhesion to CSA.

In some diagnostic embodiments, nucleic acids complementary to full-length FCR3.varCSA or fragments of FCR3.varCSA are used to identify FCR3.varCSA nucleic acids (e.g., mRNA) present in a biological sample. In other diagnostic embodiments, nucleic acids complementary to nucleic acids that encode polypeptides comprising the A4 tres DBL3-γ and ItG2-CS2 DBL2-γ (SEQ. ID. Nos: 9 and 11, respectively) sequence are used to identify FCR3.varCSA nucleic acids (e.g., mRNA) present in a biological sample. In preferred diagnostic embodiments, however, nucleic acids complementary to fragments of FCR3.varCSA that comprise sequence not found in the nucleic acid encoding other var proteins are used to identify FCR3.varCSA nucleic acids (e.g., mRNA) present in a biological sample.

Depending on the type of *Plasmodium* present in the biological sample, the concentration or expression level of nucleic acid encoding FCR3.varCSA or other varcCSA that binds CSA can differ. That is, an individual having one form of malaria can be infected with a type of parasite that produces a lower amount of a particular type of varCSA (e.g., FCR3.varCSA), or none at all. Additionally, healthy individuals will not express varCSA. Thus, malaria and, more specifically, a type of *Plasmodium* infection that leads to maternal malaria can be diagnosed by determining the concentration or expression level of a nucleic acid encoding a varCSA molecule that binds CSA (e.g., a mRNA encoding FCR3.varCSA).

For example, a FCR3.varCSA-disease state profile comprising a concentration range of a nucleic acid encoding FCR3.varCSA in a biological sample can be created for healthy and diseased individuals and these FCR3.varCSA disease state profiles can be compared to the concentrations or expression levels of a nucleic acid encoding FCR3.varCSA detected in a tested individual so as to predict or follow the disease state of that individual. Thus, in some embodiments, the term "FCR3.varCSA-disease state profile" refers to the concentration or expression level or concentration range or expression level range of a nucleic acid encoding FCR3.varCSA that is detected in a biological sample. Desirably, addressable arrays comprising nucleic acid probes complementary to the full-length FCR3.varCSA or fragments of FCR3.varCSA are used to create such FCR3.varCSA-disease state profiles. Such arrays or individual probes are also components of diagnostic kits.

In similar fashion to that discussed above, a FCR3.varCSA-disease state profile comprising concentration ranges or levels of FCR3.varCSA in healthy and diseased individuals can be created and can be used to predict or follow the disease state of an individual. In some embodiments, the term "FCR3.varCSA-disease state profile" refers to the concentration or expression level or concentration range or expression level range of a protein corresponding to FCR3.varCSA that is detected in a biological sample. Thus, by comparing a FCR3.varCSA-disease state profile from healthy individuals and subjects infected with *P. falciparum* from different regions of the world, with the FCR3.varCSA disease state profile from a tested subject, a clinician can rapidly diagnose whether the tested subject is infected with malaria and whether the type of *Plasmodium* will place the individual at risk for contracting forms of malaria that can lead to maternal malaria. Desirably, addressable arrays comprising antibodies that recognize epitopes of FCR3.varCSA are used to create such FCR3.varCSA-disease state profiles. Such arrays or antibodies are also components of diagnostic kits.

In some therapeutic and prophylactic embodiments, FCR3.varCSA, polypeptide fragments of FCR3.varCSA (e.g., DBL3 and/or CIDR1), nucleic acids encoding these molecules, and agents that interact with a FCR3.varCSA-CSA complex are incorporated into pharmaceuticals. In other therapeutic and prophylactic embodiments, polypeptides comprising the A4 tres DBL3-γ and ItG2-CS2 DBL2-γ (SEQ. ID. Nos: 9 and 11, respectively) sequence, nucleic acids encoding these molecules, and agents that interact with a varCSA-CSA complex are incorporated into pharmaceuticals. In still more embodiments, antibodies directed to the molecules above (preferably CIDR1) are provided to a subject to provide protection against PRBC binding, sequestration, and the onset of maternal malaria These pharmaceuticals can be delivered by any conventional route including, but not limited to, transdermal, parenteral, gastrointestinal, transbronchial, and transalveolar. In addition to the active ingredients mentioned above, the pharmaceutical embodiments can comprise carriers, proteins, supports, adjuvants, or components that facilitate or enhance drug delivery. These pharmaceuticals can be employed in therapeutic protocols for the treatment and prevention of maternal malaria.

Because some aspects of the invention can be used to both inhibit adhesion of FCR3.varCSA to CSA and to generate an immune response directed at FCR3.varCSA, embodiments that administer FCR3.varCSA or fragments thereof are therapeutically and prophylatically useful. By one approach, a subject at risk for contracting maternal malaria or a subject infected with *P. falciparum* is identified by conventional techniques or the diagnostic assays described herein and then is administered an effective amount of an agent that inhibits FCR3.varCSA-mediated adhesion to CSA and/or promotes an immune response in a patient. Other methods described herein concern the inhibition of the adhesion of other varCSA proteins to CSA including proteins comprising the A4 tres DBL3-γ and ItG2-CS2 DBL2-γ (SEQ. ID. Nos: 9 and 11, respectively) sequence. Similar to the approach above, this method is practiced by identifying a subject in need of an agent that disrupts the formation of a varCSA-CSA complex and administering said subject an effective amount of an agent that inhibits the formation of the varCSA-CSA complex. In still more methods of treatment and prevention of maternal malaria, a subject in need of an agent that mediates PRBC binding, sequestration, and the onset of maternal malaria is identified and then is provided a therapeutically sufficient amount of a an agent that comprises a CIDR1 domain, fragment thereof, or antibody thereto. The discovery of the FCR3.varCSA gene and FCR3.varCSA protein and its characterization as a molecule that mediates adhesion of PRBCs to CSA is disclosed below.

Identification and Isolation of the Gene Encoding FCR3.varCSA and FCR3.varCSA Protein.

Figure 1B:
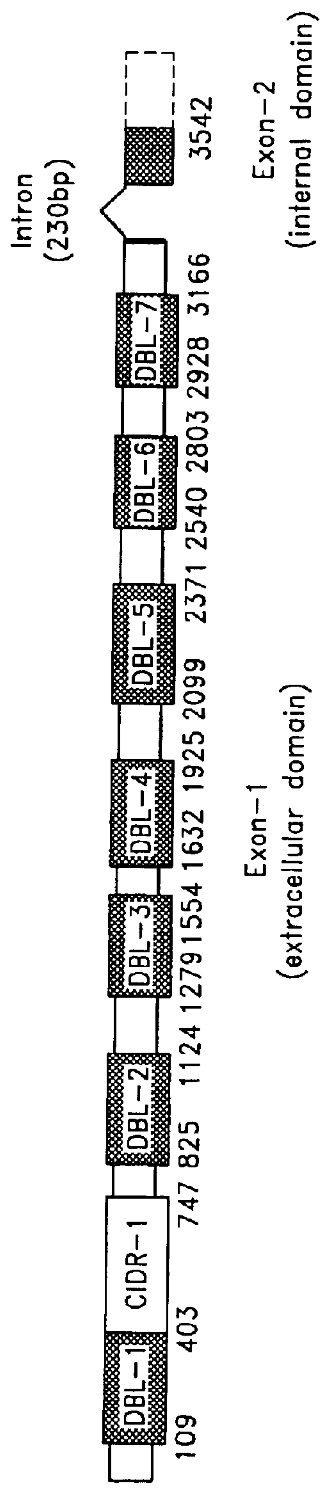
Figure 1C:
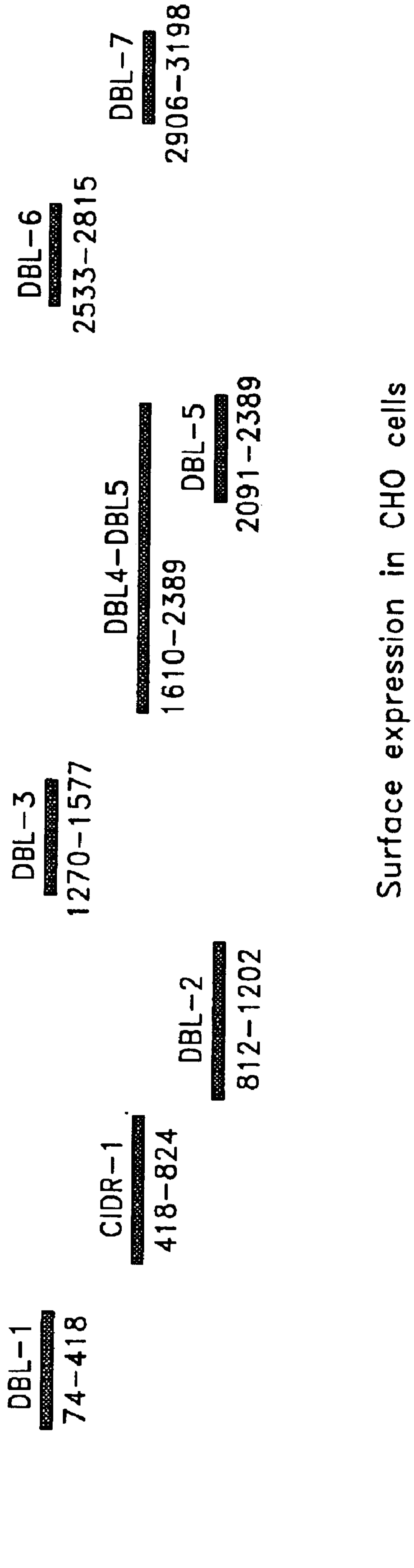

The var gene of FCR3-CSA-PRBCs was cloned and sequenced to identify the domain of the parasite ligand that mediates adhesion to CSA. A specific sequence tag of the FCR3.varCSA gene corresponding to the DBL-1 (Scherf, et al., *Embo J* 17, 5418–5426 (1998)) was used to extend the gene sequence in the 5' and 3' directions. The Vectorette technique (Genosys Biotechnologies Inc.) was employed to perform the extension. (Scherf, et al., *Embo J* 17, 5418–5426 (1998)). A nucleic acid of 10,628 bp, which contains the entire extracellular region encoded by exon I (9,931 bp), the intracellular domain of FCR3.varCSA encoded by exon II (698 bp), and an unusually short intron of 230 bp was obtained (See FIG. 1). The cloned DNA sequence predicts an open reading frame of 3,542 amino acids, and an overall structure that resembles published var sequences in that 7 DBL domains and a CIDR1 domain were found. (FIG. 1B).

The linear order of the DNA sequence obtained from genomic FCR3.varCSA was confirmed using overlapping PCR fragments from cDNA of FCR3.varCSA trophozoites (FIG. 1A) and a YAC clone (gift of Dr. M. Lanzer, University of Heidelberg) spanning most of thee exon I of the FCR3.varCSA gene. Probes to FCR3.varCSA sequence corresponding to DBL-1, DBL3/4, and DBL6/7 were found to hybridize to an identical large transcript of about 13 kb in total RNA of FCR3-CSA trophozoites. In this experiment, an Hsp70 specific probe hybridizing to the *P. falciparum* heat shock gene transcript of approximately 3 kb was used as a control. RT-PCR of mRNA and PCR of the genomic DNA also proved that the sequence was contiguous (FIG. 1A).

The RT-PCR and Northern analysis were performed as described (Scherf, et al., *Embo J* 17, 5418–5426 (1998)), from total parasite RNA prepared using the TRIZOL (Life Technologies, Gaithersburg, Md.)) extraction method (Smith, et al., *Mol Biochem Parasitol* 97, 133–48 (1998)). More evidence that the FCR3.varCSA protein is involved in CSA adhesion is provided below.

FCR3.varCSA Codes for a Large Trypsin Sensitive Erythrocyte Surface Molecule that Binds to CSA Surface iodination of FCR3-CSA trophozoite-infected RBCs identified a single molecule of about 400 kDa having the characteristics of a var gene product that binds CSA. (Baruch, et al., *Proc Natl Acad Sci USA* 93, 3497–502 (1996)). To perform this experiment, SDS extracts of surface iodinated FCR3-CSA and FCR3-CD36 trophozoites were seprated on a gel. The labeled high molecular mass proteins of approx. 400 kDa and 250 kDa were observed to be sensitive to trypsinization. Thus, evidence supporting the conclusion that the cloned gene was a member of the var family included the fact that FCR3.varCSA of intact PRBCs were sensitive to trypsin digestion and efficient extraction of FCR3.varCSA could only be achieved in a denaturing detergent (2% SDS). Notably, the iodinated portion of FCR3.varCSA was sensitive to low concentrations of trypsin but the region of the molecule that binds to CSA was not sensitive under these conditions. The surface iodination and trypsin degradation experiments were performed on *P. falciparum* FCR3 parasites that were cultured and selected on the adhesion receptors CD36 and CSA, as described in Scherf, et al., *Embo J* 17, 5418–5426 (1998). Accordingly, mature intact PRBCs were selected by the receptor panning procedure, grown for 1–2 cycles and enriched to >75% by the plasmagel technique prior to iodination. (Pasvol, et al., *Annals of Tropical Medicine & Parasitology* 72, 87–8 (1978)).

Surface iodination was accomplished by sequential extraction with 1% Triton X-100 followed by 2% SDS and trypsinization (TPCK-treated trypsin, Sigma) of PRBC, as described in Baruch, et al., *Proc Natl Acad Sci USA* 93, 3497–502 (1996). Samples derived from iodination were separated on a 0.5% agarose/4% acrylamide composite gel, dried and exposed to Kodak X-Omat XAR-5 film (Wiesner, et al., *Parasitol Today* 14, 38–40 (1998)). Prestained protein markers were used to verify the molecular size (Life Technologies, Gaithersburg, Md. and New England Biolabs Inc. Beverly, Mass.). Additionally, antibodies directed to the internal domain of MC.varl, a region conserved in var proteins, reacted with the FCR3.varCSA protein, thus, providing more evidence that the cloned molecule was a member of the var family.

Further proof that the cloned gene was a member of the var family was obtained from extensive adhesion assays (e.g., FCR3.varCSA characterization assays). In one set of experiments, iodinated FCR3.varCSA was captured by affinity purification. Accordingly, an affinity resin was made by incubating 30 μg of recombinant human thrombomodulin with 1×10⁸ tosyl activated M450 Dynabeads (4.5 μm diameter, Dynal A. S., Norway) in 1 ml of 0.1 M phosphate buffer pH 7.4 according to the protocol provided by the manufacturer. Next the affinity resin was incubated overnight at 4° C. with 15 μl of iodinated FCR3.varCSA extract (prepared by SDS extraction of FCR3-CSA PRBCs) diluted in 500 μl of BM pH 6.8 containing 1% BSA. Beads were subsequently washed using a magnet (Dynal MPC) and processed. (Baruch, et al., *Proc Natl Acad Sci USA* 93, 3497–502 (1996)).

It was found that the cloned FCR3.varCSA molecule was variant in that it was absent in CD36-selected PRBCs (FCR3-CD36), which instead expressed an iodinated molecule of 250 kDa. Additionally, surface iodinated FCR3.varCSA, extracted from FCR3-CSA PRBCs, bound to human thrombomodulin-coated dynabeads, whereas, FCR3-CD36 PfEMP1 did not bind thrombomodulin. Thus, CSA-containing thrombomodulin affinity purified a red cell surface molecule having properties expected of a member of the var family. The purified molecule was found to be sensitive to trypsin treatment. To further understand the properties of FCR3.varCSA, more FCR3.varCSA characterization assays were performed, as provided below.

Adhesive Phenotype of Parasites Selected for CSA Binding

The binding characteristics of CSA-selected PRBCs resemble the adhesive phenotype observed in PRBCs isolated from placentas of malaria infected women, that is, binding to CSA but not to CD36. (Fried & Duffy, *Science* 272, 1502–1504 (1996)). (See TABLE 1). Furthermore, sera from multigravid women from Cameroon and Senegal block efficiently adhesion of FCR3-CSA-PRBCs to CSA. These adhesion properties differ from those of a CD36-selected PRBCs that bind several receptors but not to CSA. In agreement with these clinical observations, the inventors have discovered that the CIDR1 domain of FCR3.varCSA does not bind to CD36, however, the CIDR1 domain of MC.var1, ITA4.var, and FVO.var efficiently bind to CD36.

The results presented in Table 1 are the product of several adhesion assays that were conducted as follows. A stable transfectant of CHO-745 cells (CSA negative) (Rogerson, et al., *J Exp Med* 182, 15–20 (1995)) permanently expressing cDNA's of CD36 (Berendt, et al., *Nature* 341, 57–9 (1989)), ICAM-1 (Simmons, et al., *Nature* 331, 624–7 (1988)), VCAM-1 (Osborn, et al., *Cell* 59, 1203–11 (1989)) and E-selectin (Bevilacqua, et al., *Science* 243, 1160–5 (1989)) was constructed using Fugene 6 transfection reagent (Roche Diagnostics GmbH, Germany). Additionaly, a stably transformed HUVEC cell line was kindly provided by D. Paulin and P. Vicart (Vicart, et al., *J Cell Physiol* 157, 41–51 (1993)). Surface expression of PECAM-1, ICAM-1, E-selectin and VCAM-1 was analyzed using specific monoclonal antibodies (R&D Systems, Europe Ltd). The mAB anti CD36 was a gift of L. Edelman, Institut Pasteur.

TABLE 1

Binding characteristics of FCR3-CSA and FCR3-CD36 parasites to various host receptors

| Adhesion Receptor | FCR3-CSA | FCR3-CD36 |
|---|---|---|
| [a]human thrombomodulin$^{CSA}$ | 8910 ± 352 | 34 ± 24 |
| CSA | 3545 ± 278 | 68 ± 26 |
| BIOT-CSA | 2866 ± 156 | 22 ± 15 |

TABLE 1-continued

Binding characteristics of FCR3-CSA and FCR3-CD36 parasites to various host receptors

| Adhesion Receptor | FCR3-CSA | FCR3-CD36 |
|---|---|---|
| BIOT-CSC | 32 ± 12 | nd |
| [b]placenta | 850 ± 230 | 58 ± 46 |
| [c]CHO$^{CSA}$ | 3450 ± 234 | 23 ± 34 |
| CHO$^{CD36}$ | 45 ± 32 | 2035 ± 143 |
| CHO$^{ICAM-1}$ | 24 ± 21 | 679 ± 64 |
| CHO$^{VCAM-1}$ | 46 ± 56 | 456 ± 69 |
| CHO$^{E-selectin}$ | 82 ± 34 | 235 ± 36 |
| [d]human thrombospondin (TSP-1) | 45 ± 34 | 78 ± 53 |
| [e]HUVEC$^{PECAM-1, ICAM-1, VCAM-1}$ | 124 ± 67 | 1879 ± 98 |

[a]Recombinant human thrombomodulin carrying chondroitin sulfate A (hTM) produced in CHO cells. Binding of PRBCs to receptors bound to plastic is expressed as number of PRBCs per mm² ± SD of two independent experiments.
[b]Adhesion of PRBCs to serial 7 μm cryosections of snap frozen placenta tissue was performed, as described elsewhere Gysin et al., Mol. Bioch. Parasitol. 88: 267 (1997). Only PRBCs adhesion on syncytiotrophoblasts and syncytial bridges were counted and expressed as the mean number of PRBCs ± SE per 20 high power microscopic fields (1000x Leitz Diaplan microscope).
[c]CHO-745 cells (CSA negative) stably transfected with the human adhesion receptors CD36, ICAM-1, VCAM-1 and E-selectin are described below. Cytoadherence on confluent cells is expressed as number of PRBCs per mm² ± SD of two independent experiments.
[d]Cytoadhesion of PRBCs was performed on purified human thrombospondin (TSP) (Sigma St. Louis) at 50 μg/ml in 20 mM Tris-HCl, pH 7.2, 150 mM NaCl, 2 mM CaCl spotted onto Petri dishes. Number of PRBCs per 2 mm² ± SD of two independent experiments.
[e]Nonactivated human umbilical vein endothelial cells (HUVEC) express PCAM-1, ICAM-1 and VCAM-1 as detected on HUVEC by immunofluorescence using mAB9G11, 11C81 and 4B2 (R&D Systems, Europe Ltd.).

PRBC adhesion assays were performed on transfected CHO cells and fresh cryo-sections of human placenta as described in Gysin, J., et al., *Mol Biochem Parasitol* 88, 267–71 (1997). Accordingly, adhesion of plasmagel enriched PRBCs to various receptors coated on plastic was achieved by immobilizing 10 μl of receptor in PBS directly on Petri dishes (Falcon 1001) overnight at 4° C. The receptor concentration used included recombinant human thrombomodulin$^{CSA}$ (h™) (5 μg/ml), CSA (10 μg/ml, Sigma), CSC (10 μg/ml, Sigma), Biot-CSA and Biot-CSC (100 μg/ml). The coated dots were blocked with 1% BSA and incubated with 10 μl of trophozoites (0.5% hematocrit) in binding medium (BM) (RPMI-1640 with 25 mM HEPES, pH 6.8) for 20 min at 37° C. Unaffixed cells were removed by washes in BM and the cells that remained joined to the plastic were fixed with 2% glutaraldehyde and stained in Giemsa for microscopic examination. Once it was understood that FCR3.varCSA mediated adhesion to CSA, domains of FCR3.varCSA were cloned into cells that do not express CSA so as to elucidate the regions of the molecule that mediate binding to CSA, as described in the next section.

The DBL-3 Domain of FCR3.varCSA Binds Specifically to CSA.

To identify domains of FCR3.varCSA that were involved in binding to CSA, PCR products spanning each single domain were cloned into the expression vector pSRγ5 and were transfected into CHO-745 cells (a cell line that does not natively express CSA). (Smith, et al., *Mol Biochem Parasitol* 97, 133–48 (1998)). Stable transfectants that expressed these FCR3.varCSA regions on the surface of CHO-745 cells were then selected on a Fluorescent-activated cell sorter (FACS), expanded and were used for adhesion studies that employed techniques similar to those described in Smith, et al., *Mol Biochem Parasitol* 97: 133–48 (1998).

In preparation for these adhesion studies, biotinylated-CSA and biotinylated-CSC were developed as reagents to measure CSA binding to the FCR3.varCSA domains. The activity of the biotinylated compounds was identical to that of the non-biotinylated material (TABLE 1) in that PRBCs bound only to biotin-CSA. Conjugation of biotin to chondroitin sulfate A (Bovine Trachea, Sigma St. Louis) and chondroitin sulfate C (shark cartilage, Sigma St. Louis) was accomplished by an improvement of the method described by Shinohara, et al., *J Biochem* (*Tokyo*) 117: 1076–82 (1995). Briefly, Biotinyl(aminocaproyl)3-hydraside was synthesized by Fmoc-based solid phase peptide synthesis. 0.71 mmole of P-alokoxybenzylalcohol-Wang resin (0.71 mmole/g 100–200 mesh, Watanabe Chemical Co., Japan) was treated with p-nitrophenylchloroformate (3.55 mmole, 5 eq) and pyridine (7.1 mmole, 10 eq) in $CHCl_3$ over night at room temperature. The resin was washed with $CHCl_3$ (6 times) and washed with dimethylformamide (DMF) (6 times). The resin in DMF was treated with $NH_2NH_2$.hydrate (7.1 mmole, 10 eq) by shaking for 3 hours at room temperature and washed with DMF 6 times. The resulting hydrasinated resin in DMF was acylated with Fmoc-aminocaproic acid (3 eq) 1-hydroxybenzotriazole (3 eq), and diisopropylcarbodiimide (3 eq) for coupling. 20% piperdine-DMF was used for deprotection and the reaction repeated twice more with anicaproic acid, followed by (+)-Biotin (Wako Pure Chemical Industry, Japan). The protected peptide resin was treated with TFA-m-cresol-ethanedithiol (9:0.5:0.5 coctail) for deprotection and cleavage, purified by HPLC in 0.1% MeCNaq and characterized by mass-spectrometry. Conjugation between the biotinyl-(aminocaproyl)3-hydraside and chondroitin sulfates was carried out by reductive hydrazination of chondroitin sulfate via terminal aldehyde with $NaBH_3(CN)$ in 1N AcOH at room temperature. This procedure gave a stable covalent conjugation. The conjugates were purified by gel filtration on Sephadex G-15 in 0.1N AcOH, analyzed by HPLC and the incorporation ratio was determined by combustive amino acid analysis as follows. Biotinyl-$(aminocaproyl)_3$—NHNH-chondroitin sulfate was hydrolyzed with 6N HCL containing 0.2% phenol at 110° C. for 24 hours and an aliquot of the resulting hydrolysates was subjected to amino acid analyzer (Hitachi 835 A) equipped with Chromato-Integrator (Hitachi D-2500). An unknown peak corresponding to the same retention time of aminocaproic acid was observed with CSA. Thus, the molar ratio of conjugation was calculated from the difference between the biotin-CSA to CSA alone. The incorporation was only 15% to 25%.

Biot-CSA, Biot-CSC, or soluble CD36 were immobilized via mouse monoclonal antibodies (5 μg/ml) directed either against biotin (Sigma, St. Louis) or against an epitope tag incorporated into a recombinant CD36 molecule (mAb 179). (Smith, et al., *Mol Biochem Parasitol* 97, 133–48 (1998)). The adhesion assays employing biotinylated CSA and CSC were performed with approximately, $2\times10^6$ sheep anti-mouse IgG M-450 Dynabeads were incubated overnight at 5° C. with 2 μg of mouse anti-biotin monoclonal antibody (Jackson Immunoresearch Labs, West Grove, Pa.) in PBS with continuous agitation. The beads were washed 3 times with BM pH7.2+1% BSA (BMB) and resuspended with 45 μl of BMB to $4\times10^7$ beads/ml. Approximately, 100,000 transfected CHO-745 cells were grown for 48 h. on 4 glass cover slips in six wells plates. Cover slips were transferred into a 12 wells plate containing 1 ml of BMB and 50 μg of Biot-CSA or Biot-CSC (Sigma) and incubated 1 hour.

For inhibition assays, the cells were incubated for 1 hour with 200 μg/ml of CSA or CSC (Sigma) before addition of the Biotin conjugated carbohydrates. The cover slips were washed 3 times in a basin containing BMB, transferred to a humidified chamber and incubated, 1 hour room temperature, with the coated Dynal beads (45 μl of $4\times10^7$ beads/ml). The coverslips were then flipped cell-side down onto a stand and incubated for 3 minutes to allow unbound beads to settle by gravity. Coverslips were then washed 3 times with BMB, fixed with 2% paraformaldehyde (Polysciences) in PBS and the degree of bead associated with cells was examined. In some experiments, chondroitinase ABC (Fluka, Ronkonkoma N.Y.) at 1 U/ml was added to the cells, 1 h room temperature, prior to the addition of beads.

Figure 2B:
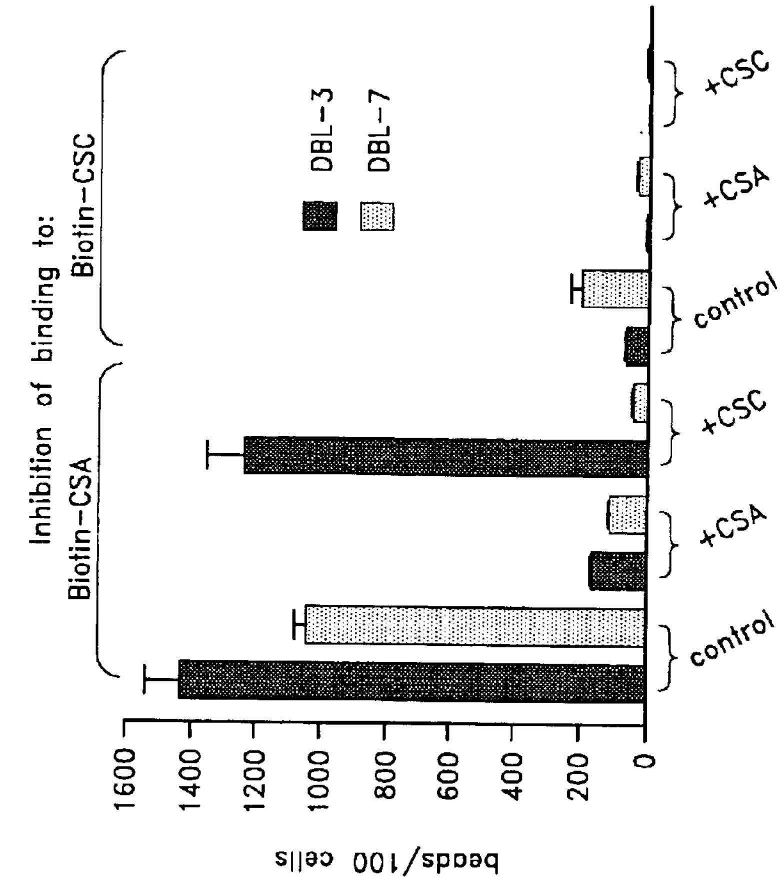
FIG. 2 (A) Binding of anti-biotin coated Dynabeads to CHO-745 cells expressing different domains of FCR3.varCSA incubated with CSA-biotin. The percentage of transfected cells that bound 4 or more beads are shown. (B) Inhibition of binding of CSA-biotin and CSC-biotin to DBL-3 and DBL-7 transfectants. Transfected cells were incubated with biotin-CSA or biotin-CSC without (control), or after preincubation with 200 μg/ml CSA (+CSA) or CSC (+CSC). Binding is given as number of positive cells (A) or number of beads (B) per 100 cells. Error bars represent the standard deviation from three different experiments.
Figure 2A:
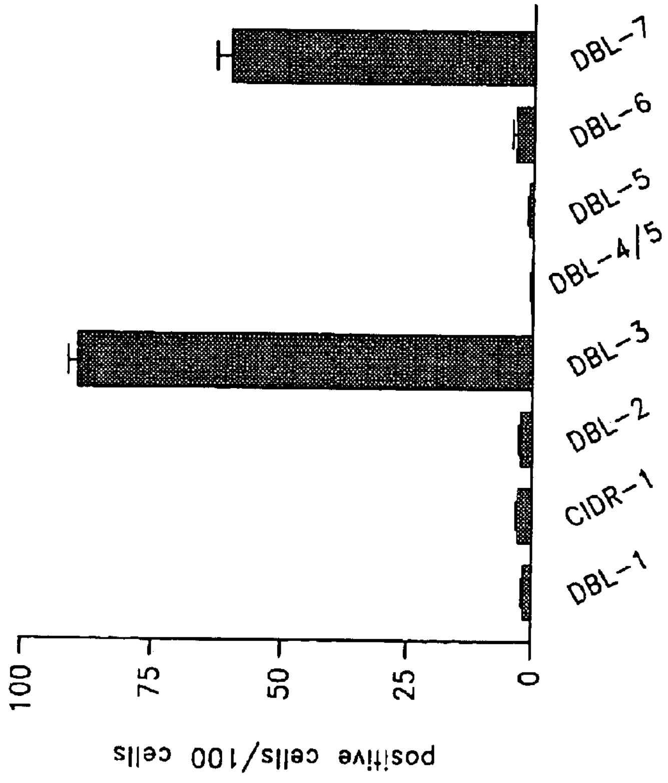

Of the eight receptor-like domains expressed on the surface of CHO-745 cells (a mutant cell line that does not express CSA, see FIG. 1C), DBL3 and DBL7 transfectants were found to bind biotin-CSA (FIG. 2A). No binding was observed when cells were incubated with biotin alone or when cells were treated with chondroitinase ABC after incubation with Biotin-CSA. Further, competition with CSA blocked the binding of biotin-CSA to both DBLs but competition with CSC, a molecule that does not block CSA-mediated PRBCs adhesion (Rogerson, et al., *J Exp Med* 182, 15–20 (1995) and (Robert, et al., *Res in Immunol* 146, 383–93 (1995)), had no effect on binding to DBL3 but did block adhesion of DBL7 (FIG. 2B). Still further, DBL7 expressed on CHO cells bound biotin-CSC, and this binding was inhibited by addition of CSA or CSC (FIG. 2B). Thus, the binding properties of DBL3, and not of DBL7, are compatible with the properties exhibited by CSA-adherent PRBCs (TABLE 1).

A previous study demonstrated that antibodies directed to two domains of a var *gene* (varCS2) from CSA-PRBCs reduced binding to CSA (Reeder, et al., *Proc Natl Acad Sci USA* 96, 5198–202 (1999)). However, the identity of a parasite CSA-binding ligand molecule was not known until this disclosure. It has been determined by direct binding studies that the FCR3.varCSA gene domain DBL-3 binds CSA. The DBL3 sequences described in Reeder, et al., *Proc Natl Acad Sci USA* 96, 5198–202 (1999) and the DBL3 sequences described herein share no specific homology other than the homology found among all DBL3 domains, and notably these regions of homology can be found in PRBCs that do not bind CSA. (Smith, et al., *Mol Biochem Parasitol* 97, 133–48 (1998)). The same is true for the CIDR1 domain. The CIDR1 domain of the FCR3-CSA var did not bind CD36, which is in full agreement with the failure of the PRBCs to bind CD36. This is in distinction from other CIDR1 domains from CD36-binding PRBCs that bind CD36. (Baruch, et al., *Blood* 90, 3766–75 (1997) and (Smith, et al., *Mol Biochem Parasitol* 97, 133–48 (1998)). Thus, the adhesion properties of a particular var protein or var domain cannot be predicted from its primary sequence.

Identification of the domain that binds CSA provides the molecular complement to the Fried and Duffy model of maternal malaria (Fried & Duffy, Science 272, 1502–1504 (1996) and (Fried, et al., *Nature* 395, 851–2 (1998)). Accordingly, at the age of first pregnancy, most residents of endemic areas are clinically immune and develop a repertoire of anti-PfEMP1 antibodies against endothelial adherent PRBCs (CD36 binding PRBCs), but not to the CSA-binding placental adherent PRBCs. Primigravid women who do not yet display antibodies against the CSA binding ligand offer a new niche for sequestration and proliferation of those parasites. The findings disclosed herein establish that antigenic variation of PfEMP1, besides its role in immune evasion, contributes to drastic changes in parasite tropism. A switch to a PfEMP1 that mediates CSA adhesion is a significant molecular event involved in the disease process observed during the first pregnancy. The data published by Fried and Duffy (Fried & Duffy, *Science* 272, 1502–1504 (1996) and (Fried, et al., *Nature* 395, 851–2 (1998)) demonstrate that antibodies from multigravid women block binding of PRBCs from placenta to CSA. This blockade of adhesion is not specific for a particular clone, as sera from multigravid females block not only PRBCs from Africa but also PRBCs from other parts of the world. Although CSA-binding PfEMP1s vary in primary sequence, a conserved three-dimensional structure or conserved antigenic determinants among various CSA-adherent strains can exist.

To test this hypothesis, several adhesion assays were conducted using polypeptide fragments of other varCSA proteins. (See TABLE 2). As above, nucleic acids encoding each polypeptide were cloned into an expression vector and were transfected into CHO-745 cells. Stable transfectants that expressed the varCSA polypeptides on the surface of CHO-745 cells were then selected on a Fluorescent-activated cell sorter (FACS), expanded and were used for adhesion studies that employed techniques similar to those described in Smith, et al., *Mol Biochem Parasitol* 97: 133–48 (1998). The adhesion assays employed biotinylated CSA and CSC and were performed as described above. The results of these assays are provided in TABLE 2.

TABLE 2

| varCSA polypeptide | Binding to CSA |
|---|---|
| R29 DBL2-γ (SEQ. ID. No.: 7) | – |
| A4 DBL4-γ (SEQ. ID. No.: 8) | – |
| A4 tres DBL3-γ (SEQ. ID. No.: 9) | +++++ |
| FCR3 var3 DBL-γ (SEQ. ID. No.: 10) | – |
| ItG2-CS2 DBL2-γ (SEQ. ID. No.: 11) | +++++ |

These assays verified that some varCSA proteins and fragments thereof are able to bind while others do not. Further, these results provided evidence that varCSA to proteins or fragments thereof that are able to bind CSA have similarity in structure despite differences in primary sequence. The section below provides several software and hardware embodiments of the invention, as well as, computational methods that can be used to further characterize a varCSA nucleic acid sequence and a varCSA polypeptide sequence, as well as, identify agents that inhibit varCSA-mediated adhesion to CSA.

Software and Hardware Embodiments

The FCR3.varCSA nucleic acid sequence and the FCR3.varCSA protein sequence were entered onto a computer readable medium for recording and manipulation. It will be appreciated by those skilled in the art that a computer readable medium having the FCR3.varCSA nucleic acid sequence or the FCR3.varCSA protein sequence or both is useful for the determination of homologous sequences, structural and functional domains, and the construction of protein models for rational drug design. The functionality of a computer readable medium having the FCR3.varCSA nucleic acid sequence or the FCR3.varCSA protein sequence or both includes the ability to compare the sequence to others stored on databases, to ascertain structural and functional information, to develop protein models, and to conduct rational drug design.

The FCR3.varCSA nucleic acid sequence or the FCR3.varCSA protein sequence or both can be stored, recorded, and manipulated on any medium that can be read and accessed by a computer. As used herein, the words "recorded" and "stored" refer to a process for storing information on computer readable medium. A skilled artisan can readily adopt any of the presently known methods for recording information on computer readable medium to generate manufactures comprising the nucleotide or polypeptide sequence information of this embodiment.

A variety of data storage structures are available to a skilled artisan for creating a computer readable medium having recorded thereon a nucleotide or polypeptide sequence. The choice of the data storage structure will generally be based on the component chosen to access the stored information. Computer readable media include magnetically readable media, optically readable media, or electronically readable media. For example, the computer readable media can be a hard disc, a floppy disc, a magnetic tape, zip disk, CD-ROM, DVD-ROM, RAM, or ROM as well as other types of other media known to those skilled in the art. The computer readable media on which the sequence information is stored can be in a personal computer, a network, a server or other computer systems known to those skilled in the art.

Embodiments include systems, particularly computer-based systems that contain the sequence information described herein. The term "a computer-based system" refers to the hardware, software, and any database used to analyze the FCR3.varCSA nucleic acid sequence or the FCR3.varCSA protein sequence or both, or fragments of these biomolecules. The computer-based system preferably includes the storage media described above, and a processor for accessing and manipulating the sequence data. The hardware of the computer-based systems of this embodiment comprise a central processing unit (CPU) and a data database. A skilled artisan can readily appreciate that any one of the currently available computer-based systems are suitable.

In one particular embodiment, the computer system includes a processor connected to a bus that is connected to a main memory (preferably implemented as RAM) and a variety of secondary storage devices, such as a hard drive and removable medium storage device. The removable medium storage device may represent, for example, a floppy disk drive, a DVD drive, an optical disk drive, a compact disk drive, a magnetic tape drive, etc. A removable storage medium, such as a floppy disk, a compact disk, a magnetic tape, etc. containing control logic and/or data recorded therein (e.g., the FCR3.varCSA nucleic acid sequence or the FCR3.var *CSA* protein sequence or both or fragments thereof) can be inserted into the removable storage device. The computer system includes appropriate software for reading the control logic and/or the data from the removable medium storage device once inserted in the removable medium storage device.

The FCR3.varCSA nucleic acid sequence or the FCR3.varCSA protein sequence or both can be stored in a well known manner in the main memory, any of the secondary storage devices, and/or a removable storage medium. Software for accessing and processing the FCR3.varCS4 nucleic acid sequence or the FCR3.varCSA protein sequence or both (such as search tools, compare tools, and modeling tools etc.) reside in main memory during execution.

As used herein, "a database" refers to memory that can store nucleotide or polypeptide sequence information, protein model information, information on other peptides, chemicals, peptidomimetics, and other agents that interact with proteins, and values or results from varCSA characterization assays. Additionally, a "database" refers to a memory access component that can access manufactures having recorded thereon nucleotide or polypeptide sequence information, protein model information, information on other peptides, chemicals, peptidomimetics, and other agents that interact with proteins, and values or results from varCSA characterization assays. In other embodiments, a database stores a varCSA disease-state profile comprising concentrations or expression levels or concentration ranges or expression level ranges of FCR3.varCSA or FCR3.varCSA or both, for example, detected in biological samples from different subjects (e.g., subjects with and without a disease related to FCR3.varCSA). In more embodiments, a database stores a FCR3.varCSA disease-state profile comprising concentration ranges or levels of FCR3.varCSA detected in biological samples obtained from various tissue or fluid sources from diseased and healthy subjects. Many databases are known to those of skill in the art and several will be discussed below.

The sequence data on FCR3.varCSA or FCR3.varCSA or both can be stored and manipulated in a variety of data processor programs in a variety of formats. For example, the sequence data can be stored as text in a word processing file, such as MicrosoftWORD or WORDPERFECT, an ASCII file, a html file, or a pdf file in a variety of database programs familiar to those of skill in the art, such as DB2, SYBASE, or ORACLE.

A "search program" refers to one or more programs that are implemented on the computer-based system to compare a nucleotide or polypeptide sequence with other nucleotide or polypeptide sequences and agents including but not limited to peptides, peptidomimetics, and chemicals stored within a database. A search program also refers to one or more programs that compare one or more protein models to several protein models that exist in a database and one or more protein models to several peptides, peptidomimetics, and chemicals that exist in a database. A search program is used, for example, to compare regions of the FCR3.varCSA nucleic acid sequence or the FCR3.varCSA protein sequence or both that match sequences in nucleic acid and protein data bases so as to identify homologies and structural or functional motifs. Further, a search program is used to compare an unknown nucleic acid or protein sequence with the FCR3.varCSA nucleic acid sequence or the FCR3.varCSA protein sequence so as to identify homologies and related structural or functional domains. Additionally, a search program is used to compare a FCR3.varCSA-disease state profile from a tested subject to FCR3.varCSA-disease state profiles from diseased and healthy subjects present in a datatbase. Still further, a search program is used to compare values or results from FCR3.varCSA characterization assays.

A "retrieval program" refers to one or more programs that are implemented on the computer based system to identify a homologous nucleic acid sequence, a homologous protein sequence, or a homologous protein model. A retrieval program is also used to identify peptides, peptidomimetics, and chemicals that interact with a nucleic acid sequence, a protein sequence, or a protein model stored in a database. Further a retrieval program is used to identify a disease state of an individual by obtaining a FCR3.varCSA disease-state profile from the database that matches the FCR3.varCSA-disease state profile from the tested subject. Additionally, a retrieval program is used to obtain "a FCR3.varCSA-agent profile" that can be composed of a nucleic acid or polypeptide sequence or model thereof or one or more symbols that represent these sequences and/or models, an identifier that represents one or more FCR3.varCSA modulating agents, and a value or result from a FCR3.varCSA characterization assay. The discussion below describes embodiments of the invention having nucleic acids that encode FCR3.varCSA.

Use of Nucleic Acids Encoding FCR3.varCSA or Fragments of FCR3.varCSA

The cDNA sequence encoding FCR3.varCSA is provided in the sequence listing (SEQ. ID NO.: 1). Full-length FCR3.varCSA and fragments of FCR3.varCSA (e.g., nucleic acids encoding DBL3 and/or CIDR1) are embodiments of the invention. Further embodiments include nucleic acids that complement full-length FCR3.varCSA and nucleic acids that complement fragments of FCR3.varCSA (e.g., nucleic acids encoding DBL3 and/or CIDR1) and other nucleic acids that encode a polypeptide that binds to CSA Desired embodiments include nucleic acids having at least 9 consecutive bases of FCR3.varCSA or a sequence complementary thereto. Preferred embodiments a include a nucleic acid that encodes a polypeptide that binds to CSA or a nucleic acid that complements a nucleic acid that encodes a polypeptide that binds to CSA.

The nucleic acid embodiments of the invention can have from 9 to 10,628 consecutive nucleotides in length that encode a fragment of FCR3.varCSA or full-length FCR3.varCSA or a complementary nucleic acid, whose complement encodes a fragment of FCR3.varCSA or full-length FCR3.varCSA. However, one of skill in the art will appreciate that FCR3.varCSA nucleic acids can be joined to an exogenous nucleic acid so as to create a nucleic acid embodiment having virtually any length. Thus, a nucleic acid having a portion (9 to 10,627 consecutive nucleotides) or full-length FCR3.varCSA are embodiments of the invention. That is, a nucleic acid having less than or equal to 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 250, 300, 350, 400, 500, 600, 700, 800, 900, 1000, 1500, 2000, 3000, 4000, 5000, 6000, 7000, 8000, 9000, 10,000, 10,500, and 10,628 nucleotides are embodied. Preferably, the nucleic acid embodiments, however, comprise at least 12, 13, 14, 15, 16, 17, 18, or 19 consecutive nucleotides from FCR3.varCSA or a nucleic acid that complements FCR3.varCSA, as conditions dictate. Nucleic acid embodiments that comprise a fragment of FCR3.varCSA (e.g., nucleic acids encoding DBL3 and/or CIDR1) or a complement thereof can be determined by referring to the sequences provided in SEQ. ID. Nos.: 1 and 2 and FIG. 1.

More preferably, the nucleic acid embodiments comprise at least 20–30 consecutive nucleotides from FCR3.varCSA or a nucleic acid that complements FCR3.varCSA. In some cases, the nucleic acid embodiments comprise more than 30 nucleotides from the nucleic acids encoding FCR3.varCSA or a nucleic acid that complements FCR3.varCSA and in other cases, the nucleic acid embodiments comprise at least 40, at least 50, at least 75, at least 100, at least 150, or at least 200 consecutive nucleotides from the nucleic acids encoding FCR3.varCSA or a nucleic acid that complements FCR3.varCSA. These nucleic acid oligomers have biotechnological and diagnostic use, e.g., in nucleotide acid hybridization assays, Southern and Northern Blot analysis, etc. and the prognosis of FCR3.varCSA-related diseases.

Some embodiments comprise recombinant nucleic acids having all or part of the FCR3.varCSA gene or recombinant nucleic acids that complement all or part of FCR3.varCSA.

Desirable embodiments comprise full-length FCR3.varCSA and fragments of FCR3.varCSA that encode a polypeptide that binds to CSA and nucleic acids that complement full-length FCR3.varCSA and fragments of FCR3.varCSA that encode a polypeptide that binds to CSA. A recombinant construct can be capable of replicating autonomously in a host cell. Alternatively, the recombinant construct can become integrated into the chromosomal DNA of the host cell. Such a recombinant polynucleotide comprises a polynucleotide of genomic or cDNA, of semi-synthetic or synthetic origin by virtue of human manipulation. Therefore, recombinant nucleic acids comprising sequences otherwise not naturally occurring are provided by embodiments of this invention. Although nucleic acids encoding FCR3.varCSA or nucleic acids having sequences that complement FCR3.varCSA as they appear in nature can be employed, they will often be altered, e.g., by deletion, substitution, or insertion and will be accompanied by sequence not present in humans.

The nucleic acid embodiments can be altered by mutation such as substitutions, additions, or deletions that provide for sequences encoding functionally equivalent molecules. Due to the degeneracy of nucleotide coding sequences, other DNA sequences that encode substantially the same FCR3.varCSA amino acid sequence as depicted in SEQ. ID NO.: 2 can be used in some embodiments of the present invention. These include, but are not limited to, nucleic acid sequences comprising all or portions of FCR3.varCSA or nucleic acids that complement all or part of FCR3.varCSA that have been altered by the substitution of different codons that encode a functionally equivalent amino acid residue within the sequence, thus producing a silent change.

In addition, recombinant FCR3.varCSA-encoding nucleic acid sequences and their complementary sequences can be engineered so as to modify processing or expression of FCR3.varCSA. For example, and not by way of limitation, the FCR3.varCSA gene can be combined with a promoter sequence and/or ribosome binding site, or a signal sequence can be inserted upstream of FCR3.varCSA-encoding sequences to permit secretion of FCR3.varCSA and thereby facilitate harvesting or bioavailability. Additionally, a given FCR3.varCSA nucleic acid can be mutated in vitro or in vivo, to create and/or destroy translation, initiation, and/or termination sequences, or to create variations in coding regions and/or form new restriction sites or destroy preexisting ones, or to facilitate further in vitro modification. Any technique for mutagenesis known in the art can be used, including but not limited to, in vitro site-directed mutagenesis. (Hutchinson et al., J. Biol. Chem. 253:6551 (1978)). Further, nucleic acids encoding other proteins or domains of other proteins can be joined to nucleic acids encoding FCR3.varCSA so as to create a fusion protein. The resulting fusion proteins are used as biotechnological tools or pharmaceuticals or both, as will be discussed below.

The nucleic acid embodiments can also be used as biotechnological tools for isolation procedures and diagnostic assays. By using the FCR3.varCSA nucleic acid sequence disclosed in the sequence listing (SEQ ID NO.: 1), probes that complement FCR3.varCSA can be designed and manufactured by oligonucleotide synthesis. These probes can be used to screen cDNA or genomic libraries so as to isolate natural sources of the nucleic acid embodiments of the present invention. Additionally, these probes can be used to isolate other nucleotide sequences capable of hybridizing to them. Further, sequences from nucleic acids complementing FCR3.varCSA, or portions thereof can be used to make oligonucleotide primers by conventional oligonucleotide synthesis for use in isolation and diagnostic procedures. These oligonucleotide primers can be used, for example, to isolate the nucleic acid embodiments of this invention by amplifying the sequences resident in genomic DNA or other natural sources by using the Polymerase Chain Reaction (PCR) or other nucleic acid amplification techniques. Further, the nucleic acid embodiments of the invention can be used to modulate FCR3.varCSA-mediated adhesion to CSA (e.g., by upregulating or downregulating the expression of FCR3.varCSA) and, therefore, have several uses in addition to biotechnological research including therapeutic and prophylactic applications, as will be discussed below. Alternatively, the nucleic acids encoding FCR3.varCSA or fragments thereof are manipulated using conventional techniques in molecular biology to create recombinant constructs that express FCR3.varCSA or fragments of FCR3.varCSA.

Embodiments also include nucleic acids encoding polypeptides that comprise A4 tres DBL3-γ (SEQ. ID. No.: 9) and ItG2-CS2 DBL2-γ (SEQ. ID No.: 11) sequence or complements thereto or fragments thereof. These nucleic acid embodiments can be for example, less than or equal to 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 250, 300, 350, 400, 500, 600, 700, 800, 900, 1000, and 1050 nucleotides in length so long as the nucleic acid can bind CSA. As with the other nucleic acid embodiments described herein, the nucleic acids encoding polypeptides that comprise A4 tres DBL3-γ (SEQ. ID. No.: 9) and ItG2-CS2 DBL2-γ (SEQ. ID. No.: 11) sequence or complements thereto or fragments thereof can be incorporated into vectors, plasmids, expression constructs and organisms, including humans. The discussion that follows describes some of the expression constructs and protein embodiments of the invention.

FCR3.varCSA Polypeptides and Fragments of FCR3.varCSA

The FCR3.varCSA polypeptides or derivatives thereof, include but are not limited to, those containing as a primary amino acid sequence all of the amino acid sequence substantially as depicted in the sequence listing (SEQ. ID NO.: 2) and fragments of SEQ. ID. NO.: 2 at least three amino acids in length. Preferred polypeptide embodiments include domains of FCR3.varCSA (e.g., DBL3 and/or CIDR1), including altered sequences in which functionally equivalent amino acid residues are substituted for residues within the sequence resulting in a silent change. The sequence of these domains or fragments thereof can be determined by referring to SEQ. ID. No. 2 and FIG. 1.

Additionally, one or more amino acid residues within the FCR3.varCSA polypeptide of SEQ ID. NO.: 2 and fragments of SEQ. ID. NO.: 2 that comprise an amino acid sequence found in a peptide that binds CSA can be substituted by another amino acid of a similar polarity that acts as a functional equivalent, resulting in a silent alteration. Substitutes for an amino acid within the sequence can be selected from other members of the class to which the amino acid belongs. For example, the non-polar (hydrophobic) amino acids include alanine, leucine, isoleucine, valine, proline, phenylalanine, tryptophan, and methionine. The polar neutral amino acids include glycine, serine, threonine, cysteine, tyrosine, asparagine and glutamine. The positively charged (basic) amino acids include arginine, lysine, and histidine. The negatively charged (acidic) amino acids include aspartic acid and glutamic acid. The aromatic amino acids include phenylalanine, tryptophan, and tyrosine.

The FCR3.varCSA fragments can be less than or equal to 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 250, 300, 350, 400, 500, 600, 700, 800, 900, 1000, 1500, 2000, 2,500, 3000, 3,500, or 3,542 amino acids in length. One embodiment, for example, comprises a polypeptide fragment having the sequence EAEKELKEG-KIPEGFKRQMFYTGDYRDILFG (SEQ. ID. NO.: 3). Desirable polypeptide embodiments comprise the sequence KELKEGKIPE (SEQ. D. NO.: 4). Preferred polypeptide embodiments comprise the sequence KEGK (SEQ. ID. NO.: 5) and, more preferably, polypeptide embodiments comprise the sequence $KX_1GX_2$ (SEQ. ID. NO.: 6), wherein $X_1$ and $X_2$ are any amino acid. In other aspects of the invention, the FCR3.varCSA polypeptide of SEQ ID. NO.: 2 and fragments of SEQ. ID. NO.: 2 that comprise an amino acid sequence that binds to CSA, or derivatives thereof are differentially modified during or after translation, e.g., by phosphorylation, glycosylation, cross-linking, acylation, proteolytic cleavage, linkage to an antibody molecule, membrane molecule, or other ligand. (Ferguson et al., Ann. Rev. Biochem. 57:285–320 (1988)).

Other embodiments include polypeptides that have homology to FCR3.varCSA and bind to CSA. By "homology to FCR3.varCSA" is meant either protein sequence homology or three-dimensional homology. As will be discussed below, several techniques exist to determine protein sequence homology and/or three-dimensional homology. These methods are routinely employed to discover related sequences and novel ligands, as well as, determine the extent of homology that one sequence, domain, or model has to a target sequence, domain, or model. Because the region of FCR3.varCSA (e.g., a region within a DBL3 domain) that mediates CSA adhesion can be, quite small (e.g., 3, 4, 5, 6, 7, 8, 9, 10, 12, 15, 18, 20, 22, 25, 30 amino acids in length) embodiments of the invention can exhibit a vast degree of homology to full-length FCR3.varCSA. For example, a fusion protein having a small region of FCR3.varCSA can exhibit a low degree of overall homology to FCR3.varCSA yet retain the ability to bind CSA. Thus, embodiments of the invention can have from 1% homology to 100% homology to full-length FCR3.varCSA. That is, embodiments can have 1.0%, 2.0%, 3.0%, 4.0%, 5.0%, 6.0%, 7.0%, 8.0%, 9.0%, 10.0%, 11.0%, 12.0%, 13.0%, 14.0%, 15.0%, 16.0%, 17.0%, 18.0%, 19.0%, 20.0%, 21.0%, 22.0%, 23.0%, 24.0%, 25.0%, 26.0%, 27.0%, 28.0%, 29.0%, 30.0%, 31.0%, 32.0%, 33.0%, 34.0%, 35.0%, 36.0%, 37.0%, 38.0%, 39.00%, 40.0%, 41.0%, 42.0%, 43.0%, 44.0%, 45.0%, 46.0%, 47.0%, 48.0%, 49.0%, 50.0%, 51.0%, 52.0%, 53.0%, 54.0%, 55.0%, 56.0%, 57.0%, 58.0%, 59.0%, 60.0%, 61.0%, 62.0%, 63.0%, 64.0%, 65.0%, 66.0%, 67.0%, 68.0%, 69.0%, 70.0%, 71.0%, 72.0%, 73.0%, 74.0%, 75.0%, 76.0%, 77.0%, 78.0%, 79.0%, 80.0%, 81.0%, 82.0%, 83.0%, 84.0%, 85.0%, 86.0%, 87.0%, 88.0%, 89.0%, 90.0%, 91.0%, 92.0%, 93.0%, 94.0%, 95.0%, 96.0%, 97.0%, 98.0%, 99.0%, and 100.0% homology to FCR3.varCSA. Therefore, embodiments of the invention include polypeptides varying in size from 3 amino acids up to and including the full-length FCR3.varCSA protein that have 1%–100% homology to FCR3.varCSA and exhibit the ability to bind to CSA.

Preferred embodiments also include polypeptides that comprise A4 tres DBL3-γ (SEQ. ID. No.: 9) and ItG2-CS2 DBL2-γ (SEQ. ID. No.: 11) sequence. These embodiments can be for example, less than or equal to 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 250, 300, 348 amino acids in length so long as the peptide can bind CSA. As above, one or more amino acid residues within the polypeptide sequence of SEQ ID. NO.: 9 and/or 11 and fragments of these molecules that comprise an amino acid sequence found in a peptide that binds CSA can be substituted by another amino acid of a similar polarity that acts as a functional equivalent, resulting in a silent alteration.

In several embodiments, the FCR3.varCSA polypeptide (SEQ ID. NO.: 2) and polypeptides comprising the A4 tres DBL3-γ (SEQ. ID. No.: 9) and the ItG2-CS2 DBL2-γ (SEQ. ID. No.: 11) sequence and fragments of these molecules are expressed in a cell line. The term "isolated" requires that the material be removed from its original environment (e.g., the natural environment if it is naturally occuring). For example, a naturally occurring nucleic acid or protein present in a living cell is not isolated, but the same nucleic acid or protein, separated from some or all of the coexisting materials in the natural system, is isolated. In accordance with this definition, FCR3.varCSA nucleic acid or FCR3.varCSA protein or nucleic acid or polypeptide fragments present in a cell lysate are "isolated". The term "purified" does not require absolute purity, rather it is intended as a relative definition. For example, recombinant nucleic acids and proteins are routinely purified to electrophoretic homogeneity, as detected by ethidum bromide staining or Coomassie staining, and are suitable in several assays despite having the presence of contaminants.

To express the protein embodiments described herein, nucleic acids containing the coding sequence for these molecules are obtained and cloned into a suitable expression vector such that the coding region is operably linked to a heterologous promoter. The nucleic acid encoding the protein or polypeptide to be expressed is operably linked to a promoter in an expression vector using conventional cloning technology. The expression vector can be in any of the mammalian, yeast, amphibian, insect, parasite, or bacterial expression systems known in the art. Commercially available vectors and expression systems are available from a variety of suppliers including Genetics Institute (Cambridge, Mass.), Stratagene (La Jolla, Calif.), Promega (Madison, Wis.), and Invitrogen (San Diego, Calif.). If desired, to enhance expression and facilitate proper protein folding, the codon context and codon pairing of the sequence can be optimized for the particular expression organism in which the expression vector is introduced, as explained by Hatfield, et al., U.S. Pat. No. 5,082,767. Further, a secretory leader sequence can be incorporated so as to facilitate purification of the protein.

The following is provided as one exemplary method to express the proteins encoded by the nucleic acids described above. First, the methionine initiation codon for the gene and the poly A signal of the gene are identified. If the nucleic acid encoding the polypeptide to be expressed lacks a methionine to serve as the initiation site, an initiating methionine can be introduced next to the first codon of the nucleic acid using conventional techniques. Similarly, if the nucleic acid lacks a poly A signal, this sequence can be added to the construct by, for example, splicing out the Poly A signal from pSG5 (Stratagene) using BglI and SalI restriction endonuclease enzymes and incorporating it into the mammalian expression vector pXT1 (Stratagene). The vector pXT1 contains the LTRs and a portion of the gag gene from Moloney Murine Leukemia Virus. The position of the LTRs in the construct allow efficient stable transfection. The vector includes the Herpes Simplex Thymidine Kinase promoter and the selectable neomycin gene.

The nucleic acid encoding the polypeptide to be expressed can be obtained by PCR from the bacterial vector using oligonucleotide primers complementary to the nucleic acid and containing restriction endonuclease sequences for Pst I incorporated into the 5'primer and BglII at the 5' end of the corresponding cDNA 3' primer, taking care to ensure that the nucleic acid is positioned in frame with the poly A signal. The purified fragment obtained from the resulting PCR reaction is digested with PstI, blunt ended with an exonuclease, digested with Bgl II, purified and ligated to pXT1, now containing a poly A signal and digested with BglII. The ligated product is transfected into a suitable cell line, e.g., mouse NIH 3T3 cells, using lipofectin (Life Technologies, Inc., Grand Island, N.Y.) under conditions outlined in the product specification. Positive transfectants are selected after growing the transfected cells in 600 $\mu$g/ml G418 (Sigmna, St. Louis, Mo.). Preferably the expressed protein is released into the culture medium, thereby facilitating purification.

Another embodiment utilizes the "Xpress system for expression and purification" (Invitrogen, San Diego, Calif.). The Xpress system is designed for high-level production and purification of recombinant proteins from bacterial, mammalian, and insect cells. The Xpress vectors produce recombinant proteins fused to a short N-terminal leader peptide that has a high affinity for divalent cations. Using a nickel-chelating resin (Invitrogen), the recombinant protein can be purified in one step and the leader can be subsequently removed by cleavage with enterokinase.

One preferred vector for the expression of FCR3.varCSA and fragments of FCR3.varCSA is the pBlueBacHis2 Xpress. The pBlueBacHis2 Xpress vector is a Baculovirus expression vector containing a multiple cloning site, an ampicillin resistance gene, and a lac z gene. By one approach, the FCR3.varCSA nucleic acid, or portion thereof is cloned into the pBlueBacHis2 Xpress vector and SF9 cells are infected. The expression protein is then isolated or purified according to the manufacturer's instructions. Several other cultured cell lines having recombinant constructs or vectors comprising FCR3.varCSA or portions thereof are embodiments of the present invention and their manufacture would be routine given the present disclosure.

Proteins in the culture medium can also be separated by gel electrophoresis. The separated proteins are then detected using techniques such as Coomassie or silver staining or by using antibodies against the protein. Coomassie, silver staining, and immunolabeling of proteins are techniques familiar to those skilled in the art. If desired, the proteins can also be ammonium sulfate precipitated or separated based on size or charge prior to electrophoresis.

The protein embodiments described herein can also be purified using standard immunochromatography techniques. In such procedures, a solution containing the protein, such as the culture medium or a cell extract, is applied to a column having antibodies against the protein attached to the chromatography matrix. The protein is allowed to bind the immunochromatography column. Thereafter, the column is washed to remove non-specifically bound proteins. The specifically bound protein is then released from the column and recovered using standard techniques.

Further, nucleic acids encoding a protein embodiment or portion thereof can be incorporated into expression vectors designed for use in purification schemes employing chimeric polypeptides. In one such strategy, for example, the coding sequence of FCR3.varCSA or portion therof is inserted in frame with the gene encoding the other half of the chimera. The other half of the chimera may be β-globin or a nickel binding polypeptide encoding sequence. A chromatography matrix having antibody to β-globin or nickel attached thereto is then used to purify the chimeric protein. Protease cleavage sites can be engineered between the β-globin gene or the nickel binding polypeptide and the FCR3.varCSA cDNA such as enterokinase. Thus, the two polypeptides of the chimera can be separated from one another by protease digestion.

One useful expression vector for generating β-globin chimerics is pSG5 (Stratagene), which encodes rabbit β-globin. Intron II of the rabbit β-globin gene facilitates splicing of the expressed transcript, and the polyadenylation signal incorporated into the construct increases the level of expression. These techniques as described are well known to those skilled in the art of molecular biology. Standard methods are published in methods texts such as Davis et al., (*Basic Methods in Molecular Biology* L. G. Davis, M. D. Dibner, and J. F. Battey, ed., Elsevier Press, NY, 1986) and many of the methods are available from Stratagene, Life Technologies, Inc., or Promega Polypeptide may additionally be produced from the construct using in vitro translation systems, such as the In vitro Express™ Translation Kit (Stratagene).

In addition to isolating or purifying the protein embodiments by using recombinant DNA techniques, these molecules can be prepared by chemical synthesis methods (such as solid phase peptide synthesis) using methods known in the art such as those set forth by Merrifield et al., J. Am. Chem. Soc. 85:2149 (1964), Houghten et al., Proc. Natl. Acad. Sci. USA, 82:51:32 (1985), and Stewart and Young (solid phase peptide synthesis, Pierce Chem Co., Rockford, Ill. (1984)). Such polypeptides can be synthesized with or without a methionine on the amino terminus. Chemically synthesized FCR3.varCSA and fragments of FCR3.varCSA can be oxidized using methods set forth in these references to form disulfide bridges. FCR3.varCSA and fragments of FCR3.varCSA can be employed as biologically active or immunological substitutes for natural, purified FCR3.varCSA and fragments of FCR3.varCSA, for example. Further, peptidomimetics that structurally and/or functionally resemble a peptide embodiment (e.g., FCR3.varCSA or fragments of FCR3.varCSA) can be made and evaluated for their ability to interact with CSA in a characterization assay or to induce an immune response in a subject. Several approaches to make peptidomimetics that resemble polypeptides have been described. A vast number of methods, for example, can be found in U.S. Pat. Nos. 5,288,707; 5,552,534; 5,811,515; 5,817,626; 5,817,879; 5,821,231; and 5, 874,529.

Following synthesis or expression and isolation or purification of a protein embodiment, the isolated or purified molecules can be used to generate antibodies and tools for identifying agents that interact with a varCSA and fragments of a varCSA. Antibodies that recognize FCR3.varCSA and fragments of FCR3.varCSA (e.g., CIDR1 and/or DBL3), as well as A4 tres DBL3-γ (SEQ. ID. No.: 9) and ItG2-CS2 DBL2-γ (SEQ. ID. No.: 11) or fragments thereof, for example, have many uses including, but not limited to, biotechnological applications, therapeutic/prophylactic applications, and diagnostic applications. Such antibodies include, but are not limited to, polyclonal, monoclonal, chimeric, single chain, Fab fragments and fragments produced by a Fab expression library. Neutralizing antibodies, e.g., those that inhibit FCR3.varCSA-mediated adhesion or formation of a complex having varCSA and CSA, are especially preferred for diagnostics and therapeutics.

For the production of antibodies, various hosts including goats, rabbits, rats, mice, etc can be immunized by injection with a protein embodiment that has immunogenic properties. Depending on the host species, various adjuvants can be used to increase immunological response. Such adjuvants include but are not limited to Freund's, mineral gels such as aluminum hydroxide, and surface active substances such as lysolecithin, pluronic polyols, polyanions, peptides, oil emulsions, keyhole limpet hemocyanin, and dinitrophenol. BCG *Bacillus* Calmette-Guerin) and *Corynebacterium parvum* are potentially useful adjuvants.

Peptides used to induce specific antibodies can have an amino acid sequence consisting of at least three amino acids, preferably at least 10 or 15 amino acids. Desirably, short stretches of amino acids encoding fragments of a varCSA molecule (e.g., FCR3.varCSA, A4 tres DBL3-γ, or ItG2-CS2 DBL2-γ) are fused with those of another protein such as keyhole limpet hemocyanin and antibody is produced against the chimeric molecule. While antibodies capable of specifically recognizing a varCSA molecule, for example, can be generated by injecting into mice synthetic 3-mer, 10-mer, and 15-mer peptides that correspond to the particular protein sequence, a more diverse set of antibodies can be generated by using a recombinant or purified protein embodiment.

For example, to generate antibodies to FCR3.varCSA and fragments of FCR3.varCSA, substantially pure FCR3.varCSA or a fragment of FCR3.varCSA (e.g., DBL3, CIDR1, A4 tres DBL3-γ, or ItG2-CS2 DBL2-γ) is isolated from a transfected or transformed cell. The concentration of the polypeptide in the final preparation is adjusted, for example, by concentration on an Amicon filter device, to the level of a few micrograms/ml. Monoclonal or polyclonal antibody to the polypeptide of interest can then be prepared as follows:

Monoclonal antibodies to a varCSA protein or a fragment thereof can be prepared using any technique that provides for the production of antibody molecules by continuous cell lines in culture. These include but are not limited to the hybridoma technique originally described by Koehler and Milstein (Nature 256:495–497 (1975), the human B-cell hybridoma technique (Kosbor et al. Immunol Today 4:72 (1983); Cote et al Proc Natl Acad Sci 80:2026–2030 (1983), and the EBV-hybridoma technique Cole et al. Monoclonal Antibodies and Cancer Therapy, Alan R. Liss Inc, New York N.Y., pp 77–96 (1985). In addition, techniques developed for the production of "chimeric antibodies", the splicing of mouse antibody genes to human antibody genes to obtain a molecule with appropriate antigen specificity and biological activity can be used. (Morrison et al. Proc Natl Acad Sci 81:6851–6855 (1984); Neuberger et al. Nature 31:2:604–608 (1984); and Takeda et al. Nature 314:452–454 (1985). Alternatively, techniques described for the production of single chain antibodies (U.S. Pat. No. 4,946,778) can be adapted to produce specific single chain antibodies. Antibodies can also be produced by inducing in vivo production in the lymphocyte population or by screening recombinant immunoglobulin libraries or panels of highly specific binding reagents as disclosed in Orlandi et al., Proc Natl Acad Sci 86: 3833–3837 (1989), and Winter G. and Milstein C; Nature 349:293–299 (1991).

Antibody fragments that contain specific binding sites for FCR3.varCSA (e.g., DBL3, CIDR1, A4 tres DBL3-γ, or ItG2-CS2 DBL2-γ) can also be generated. For example, such fragments include, but are not limited to, the $F(ab')_2$ fragments that can be produced by pepsin digestion of the antibody molecule and the Fab fragments that can be generated by reducing the disulfide bridges of the $F(ab')_2$ fragments. Alternatively, Fab expression libraries can be constructed to allow rapid and easy identification of monoclonal Fab fragments with the desired specificity. (Huse W. D et al. Science 256:1275–1281 (1989)).

By one approach, monoclonal antibodies are made as follows. Briefly, a mouse is repetitively inoculated with a few micrograms of the selected protein or peptides derived therefrom over a period of a few weeks. The mouse is then sacrificed, and the antibody producing cells of the spleen isolated. The spleen cells are fused in the presence of polyethylene glycol with mouse myeloma cells, and the excess unfused cells destroyed by growth of the system on selective media comprising aminopterin (HAT media). The successfully fed cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall, E., *Meth. Enzymol.* 70:419 (1980) and derivative methods thereof. Selected positive clones can be expanded and their monoclonal antibody product harvested for use. Detailed procedures for monoclonal antibody production are described in Davis, L. et al. *Basic Methods in Molecular Biology* Elsevier, N.Y. Section 21-2.

Polyclonal antiserum containing antibodies to heterogeneous epitopes of a single protein can be prepared by immunizing suitable animals with the expressed protein or peptides derived therefrom described above, which can be unmodified or modified to enhance immunogenicity. Effective polyclonal antibody production is affected by many factors related both to the antigen and the host species. For example, small molecules tend to be less immunogenic than others and may require the use of carriers and adjuvant. Also, host animals vary in response to site of inoculations and dose, with both inadequate or excessive doses of antigen resulting in low titer antisera. Small doses (ng level) of antigen administered at multiple intradermal sites appears to be most reliable. An effective immunization protocol for rabbits can be found in Vaitukaitis, J. et al. *J Clin Endocrinol. Metab.* 33:988–991 (1971).

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony, O. et al., Chap. 19 in: *Handbook of Experimental Immunology* D. Wier (ed) Blackwell (1973). Plateau concentration of antibody is usually in the range of 0.1 to 0.2 mg/ml of serum (about 12 $\mu$M). Affinity of the antisera for the antigen is determined by preparing competitive binding curves, as described, for example, by Fisher, D., Chap. 42 in: *Manual of Clinical Immunology,* 2 d Ed. (Rose and Friedman, Eds.) Amer. Soc. For Microbiol., Washington, D.C. (1980). Antibody preparations prepared according to either protocol are useful in quantitative immunoassays that determine concentrations of antigen-bearing substances in biological samples;

they are also used semi-quantitatively or qualitatively (e.g., in diagnostic embodiments that identify the presence of a varCSA molecule in biological samples).

Additionally, FCR3.varCSA, fragments of FCR3.varCSA, A4 tres DBL3-γ, or ItG2-CS2 DBL2-γ can be used to induce antibody production in humans. That is, these peptides whether made chemically or as detailed above, can be used as an antigen or vaccine so as to elicit an immune response in a patient. Accordingly, FCR3.varCSA, fragments of FCR3.varCSA, A4 tres DBL3-γ, or ItG2-CS2 DBL2-γ can be joined to or administered with another protein, carrier, support, or adjuvant so as to generate a pharmaceutical or vaccine that will induce potent immune response. Additionally, nucleic acids encoding FCR3.varCSA, fragments of FCR3.varCSA, A4 tres DBL3-γ, or ItG2-CS2 DBL2-γ can be administered by themselves or with FCR3.varCSA, fragments of FCR3.varCSA, A4 tres DBL3-γ, or ItG2-CS2 DBL2-γ and, as above, can be joined to or administered with a protein, carrier, support, or adjuvant. These nucleic acids can be administered "naked" or can be incorporated into vectors. Vaccination protocols can include, for example, identifying a subject in need of a vaccine (e.g., pregnant women in regions populated with *P. falciparum*) and administering to said subject a therapeutically effective amount of either a protein or a nucleic acid-based vaccines or combinations of protein and nucleic acid vaccines. The next section describes the use of var characterization assays and methods to identify agents that modulate FCR3.varCSA-mediated adhesion.

Modulation of FCR3.varCSA-dependent Adhesion to CSA

The data above establishes that FCR3.varCSA, fragments of FCR3.varCSA, A4 tres DBL3-γ, or ItG2-CS2 DBL2-γ efficiently associate with CSA to form a varCSA-CSA complex. The formation of such a complex can be measured using many techniques common to immunology and receptor biology. By one approach, FCR3.varCSA dependent adhesion to CSA is analyzed by contacting a support having CSA or a representative fragment of CSA with FCR3.varCSA or a representative fragment of FCR3.varCSA. If the FCR3.varCSA or fragment thereof is detectably labeled (e.g., $^{125}I$), the association to immobilized CSA (or CSA fragment) can be directly determined by detecting the signal (e.g., scintillation counting). Alternatively, the association of FCR3.varCSA, fragments of FCR3.varCSA, A4 tres DBL3-γ, or ItG2-CS2 DBL2-γ with CSA can be determined indirectly by employing a detectably labeled antibody that has an epitope that corresponds to a region of FCR3.varCSA. In these assays, the support can be a resin, plastic, a membrane, a lipid, and a cell. Additionally, the varCSA or fragment thereof can be joined to a second support so as to more closely reproduce native conditions. Many varCSA characterization assays can be automated (e.g., high throughput screening employing a fluorescently labeled FCR3.varCSA or fragment thereof) so as to quickly identify regions of the molecule that are involved in binding to CSA. Values or results from these assays can be recorded on a computer readable media (e.g., in a database) and analyzed with a search program and retrieval program. Of course, embodiments of the invention include the converse of the assay described above. That is, immobilizing FCR3.varCSA, fragments of FCR3.varCSA, A4 tres DBL3-γ, or ItG2-CS2 DBL2-γ on a support and detecting the adhesion of labeled CSA or fragments of CSA.

Additional embodiments include methods of identifying agents that modulate the formation of a varCSA-CSA complex. By one approach, an agent that modulates varCSA-CSA adhesion can be identified by contacting a support having CSA or a representative fragment thereof with FCR3.varCSA, fragments of FCR3.varCSA, A4 tres DBL3-γ, or ItG2-CS2 DBL2-γ in the presence of the agent. Detection of adhesion is accomplished, as described above, and successful agents are identified according to their ability to induce a desired modulation of the formation of the varCSA-CSA complex. As above, the support can be a resin, a membrane, plastic, a lipid, or a cell and the varCSA or fragment thereof can be joined to a second support so as to more nearly reproduce native binding conditions. In another approach, a support having a varCSA or a representative fragment thereof can be used to capture directly or indirectly labeled CSA or fragments of CSA. In some aspects, the fragments of FCR3.varCSA that are used have a polypeptide sequence that binds to CSA and is at least 80% homologous to FCR3.varCSA. As above, binding is conducted in the presence of the agent and FCR3.varCSA dependent adhesion to CSA is determined by the amount of labeled CSA bound to the immobilized FCR3.varCSA. In this method, the support can be a resin, a membrane, plastic, a lipid, and a cell and the CSA can also be joined to a second support to approximate native binding conditions.

In a preferred approach, an agent that modulates varCSA dependent adhesion to CSA is identified using a cell-based assay. Accordingly, cells are transfected with a construct comprising a nucleic acid sequence encoding a varCSA or a representative fragment thereof. Transfectants are brought in contact with a support having CSA (or CSA fragment) and, as above, binding is conducted in the presence of the agent. Adhesion to CSA is determined by the amount of labeled CSA bound to the varCSA (or fragment thereof) expressing cells. In this method, the support can be a resin, a membrane, plastic, a lipid, and another cell. The converse of this assay can also be performed. That is, CSA expressing cells can be bound to immobilized varCSA or fragments of varCSA in the presence of a modulator. Further, a two-cell adhesion assay employing a first cell that expresses CSA and a second cell that expresses a varCSA or fragment thereof can be performed. Accordingly, the inhibition of cell aggregation in the presence of a modulator indicates that the agent is effective at disrupting varCSA-mediated CSA adhesion.

In some aspects of the invention, nucleic acids encoding FCR3.varCSA, nucleic acids complementary to FCR3.varCSA, FCR3.varCSA protein, and polypeptide fragments of FCR3.varCSA are agents that modulate (e.g., inhibit or enhance) the formation of the FCR3.varCSA-CSA complex. Several embodiments are provided that inhibit the association of FCR3.varCSA in a FCR3.varCSA-CSA complex or otherwise inhibit PRBC binding, sequestration, and the onset of maternal malaria (collectively referred to as "FCR3.varCSA inhibitory agents"). One embodiment concerns an inhibitory agent that is an antisense oligonucleotide or ribozyme that hybridizes to nucleic acid encoding regions of a varCSA molecule (e.g., FCR3.varCSA, DBL3, CIDR1, A4 tres DBL3-γ, or ItG2-CS2 DBL2-γ). By "antisense oligonucleotide" is meant a nucleic acid or modified nucleic acid including, but not limited to DNA, RNA, modified DNA or RNA (including branched chain nucleic acids and 2' O-methyl RNA) and PNA (polyamide nucleic acid).

Several ribozymes known to those of skill in the art can be easily designed to hybridize to nucleic acid sequence encoding a varCSA or fragment thereof and thereby inhibit the production of functional protein. Desirably, antisense oligonucleotides or ribozymes that hybridize to the start codon are used. In one embodiment, full length antisense FCR3.varCSA is used to significantly reduced FCR3.varCSA-dependent adhesion to CSA. Many other antisense oligonucleotides or ribozymes that interfere with the formation of a varCSA-CSA complex can be designed and screened by the methods detailed previously.

The antisense nucleic acids should have a length and melting temperature sufficient to permit formation of an intracellular duplex having sufficient stability to inhibit the expression of the mRNA in the duplex. Strategies for designing antisense nucleic acids suitable for use in gene therapy are disclosed in Green et al., *Ann. Rev. Biochem.,* 55:569–597 (1986) and Izant and Weintraub, *Cell,* 36:1007–1015 (1984). In some strategies, antisense molecules are obtained from a nucleotide sequence encoding FCR3.varCSA by reversing the orientation of the coding region with respect to a promoter so as to transcribe the opposite strand from that which is normally transcribed in the cell. Antisense molecules and ribozymes can be prepared by any method known in the art for the synthesis of RNA molecules. These include techniques for chemically synthesizing oligonucleotides such as solid phase phosphoramidite chemical synthesis.

Additionally, RNA molecules can be generated by in vitro and in vivo transcription of DNA sequences encoding FCR3.varCSA, fragments of FCR3.varCSA, A4 tres DBL3-γ, or ItG2-CS2 DBL2-γ. Such DNA sequences can be incorporated into a wide variety of vectors with suitable RNA polymerase promoters such as T7 or SP6. Further, antisense cDNA constructs that synthesize antisense RNA constitutively or inducibly can be introduced into cell lines, cells or tissues. Still further, oligonucleotides that are complementary to the mRNA encoding FCR3.varCSA, fragments of FCR3.varCSA, A4 tres DBL3-γ, or ItG2CS2 DBL2-γ can be synthesized in vitro. Thus, antisense nucleic acids are capable of hybridizing to a varCSA mRNA to create a duplex. In some embodiments, the antisense sequences can contain modified sugar phosphate backbones to increase stability and make them less sensitive to RNase activity. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine and wybutosine as well as acetyl-, methyl-, thio- and similarly modified forms of adenine, cytidine, guanine, thymine, and uridine that are not as easily recognized by endogenous endonucleases. Further examples are described by Rossi et al., *Pharmacol. Ther.,* 50(2) :245–254, (1991).

Various types of antisense oligonucleotides complementary to a nucleic acid encoding FCR3.varCSA, fragments of FCR3.varCSA, A4 tres DBL3-γ, or ItG2-CS2 DBL2-γ can be used. In one preferred embodiment, stable and semi-stable antisense oligonucleotides described in International Application No. PCT WO94/23026 are used. In these molecules, the 3' end or both the 3' and 5' ends are engaged in intramolecular hydrogen bonding between complementary base pairs. These molecules are better able to withstand exonuclease attacks and exhibit increased stability compared to conventional antisense oligonucleotides. In another preferred embodiment, the antisense oligodeoxynucleotides described in International Application No. WO 95/04141 are used. In yet another preferred embodiment, the covalently cross-linked antisense oligonucleotides described in International Application No. WO 96/31523 are used. These double- or single-stranded oligonucleotides comprise one or more, respectively, inter- or intra-oligonucleotide covalent cross-linkages, wherein the linkage consists of an amide bond between a primary amine group of one strand and a carboxyl group of the other strand or of the same strand, respectively, the primary amine group being directly substituted in the 2' position of the strand nucleotide monosaccharide ring, and the carboxyl group being carried by an aliphatic spacer group substituted on a nucleotide or nucleotide analog of the other strand or the same strand, respectively.

The antisense oligodeoxynucleotides and oligonucleotides disclosed in International Application No. WO 92/18522 can also be used. These molecules are stable to degradation and contain at least one transcription control recognition sequence that binds to control proteins and are effective as decoys therefor. These molecules can contain "hairpin" structures, "dumbbell" structures, "modified dumbbell" structures, "cross-linked" decoy structures and "loop" structures. In another preferred embodiment, the cyclic double-stranded oligonucleotides described in European Patent Application No. 0 572 287 A2 are used. These ligated oligonucleotide "dumbbells" contain the binding site for a transcription factor and inhibit expression of the gene under control of the transcription factor by sequestering the factor. Use of the closed antisense oligonucleotides disclosed in International Application No. WO 92/19732 is also contemplated. Because these molecules have no free ends, they are more resistant to degradation by exonucleases than are conventional oligonucleotides. These oligonucleotides can be multifunctional, interacting with several regions that are not adjacent to the target mRNA The appropriate level of antisense nucleic acids required to inhibit formation of the varCSA-CSA complex can be determined using in vitro expression analysis and the varCSA characterization assays described herein. The antisense molecule can be introduced into the cells expressing FCR3.varCSA, fragments of FCR3.varCSA, A4 tres DBL3-γ, or ItG2-CS2 DBL2-γ by diffusion, injection, infection or transfection using procedures known in the art. For example, the antisense nucleic acids can be introduced into the body as a bare or naked oligonucleotide, oligonucleotide encapsulated in lipid, oligonucleotide sequence encapsidated by viral protein, or as an oligonucleotide operably linked to a promoter contained in an expression vector. The expression vector can be any of a variety of expression vectors known in the art, including retroviral or viral vectors, vectors capable of extrachromosomal replication, or integrating vectors. The vectors can be DNA or RNA.

The antisense molecules are introduced onto cell samples at a number of different concentrations preferably between $1\times10^{-10}$ M to $1\times10^{-4}$ M. Once the minimum concentration that can adequately control gene expression is identified, the optimized dose is translated into a dosage suitable for use in vivo. For example, an inhibiting concentration in culture of $1\times10^{-7}$ translates into a dose of approximately 0.6 mg/kg bodyweight. Levels of oligonucleotide approaching 100 mg/kg bodyweight or higher can be possible after testing the toxicity of the oligonucleotide in laboratory animals. It is additionally contemplated that cells from a vertebrate, such as a mammal or human, are removed, treated with the antisense oligonucleotide, and reintroduced into the vertebrate.

Ribozymes can also be used to reduce or eliminate expression of FCR3.varCSA, fragments of FCR3.varCSA, A4 tres DBL3-γ, or ItG2-CS2 DBL2-γ. Ribozymes are enzymatic RNA molecules capable of catalyzing the specific cleavage of RNA. The mechanism of ribozyme action involves sequence-specific hybridization of the ribozyme molecule to complementary target RNA, followed by endonucleolytic cleavage. Within the scope of aspects of the invention, are engineered hammerhead motif ribozyme molecules that can specifically and efficiently catalyze endonucleolytic cleavage of a sequence encoding FCR3.varCSA, for example. Specific ribozyme cleavage sites within any potential RNA target are initially identified by scanning the target molecule for ribozyme cleavage sites that include the following sequences, GUA, GUU and GUC. Once identified, short RNA sequences of between 15 and 20 ribonucleotides corresponding to the region of the target gene containing the cleavage site can be evaluated for secondary structural features that may render the oligonucleotide inoperable. The suitability of candidate targets can also be evaluated by testing accessibility to hybridization with complementary oligonucleotides using ribonuclease protection assays. Delivery of antisense and ribozyme agents by transfection and by liposome are quite well known in the art.

Another embodiment of an inhibitory agent is a polypeptide that interferes with the association of FCR3.varCSA, fragments of FCR3.varCSA, A4 tres DBL3-γ, or ItG2-CS2 DBL2-γ with CSA. Polypeptide fragments that inhibit the association of with CSA can be rapidly engineered and identified given the present disclosure and candidate polypeptides can contain regions of FCR3.varCSA, fragments of FCR3.varCSA, A4 tres DBL3-γ, ItG2-CS2 DBL2-γ or CSA. The screening of polypeptide fragments and mutant proteins that inhibit the association of a complex having these molelcules would be routine given the present disclosure and assays described herein. For example, polypeptide FCR3.varCSA inhibitory agents can be identified by their ability to disrupt the formation of the FCR3.varCSA-CSA complex by employing conventional affinity chromatography techniques, sandwich assays, ELISA assays, or other binding assays known to those of skill in the art and described above. A screening method, for example, wherein the polypeptide FCR3.varCSA inhibitory agent is administered to ski, cells expressing FCR3.varCSA in culture and cell lysates are analyzed by immunoprecipitation and Western blot can rapidly evaluate the polypeptide's ability to inhibit the association of a an FCR3.varCSA-CSA complex.

In another embodiment, concentrations of FCR3.varCSA, fragments of FCR3.varCSA, A4 tres DBL3-γ, or ItG2-CS2 DBL2-γ are raised in a cell so as to enhance adhesion to CSA. There may be many ways to raise the concentration of these molecules or CSA or both in a cell. Liposome-mediated transfer, is one approach to deliver FCR3.varCSA, fragments of FCR3.varCSA, A4 tres DBL3-γ, ItG2-CS2 DBL2-γ or CSA or both protein to a cell. Alternatively, the concentration of FCR3.varCSA, fragments of FCR3.varCSA, A4 tres DBL3-γ, ItG2-CS2 DBL2-γ or CSA or any combination thereof can be raised in a cell by transfecting constructs encoding these molecules. A construct for use in the transfection of FCR3.varCSA into cells in culture, for example, was described previously and many others can be developed by those of skill in the art.

Retroviral constructs for the delivery of nucleic acid encoding FCR3.varCSA, fragments of FCR3.varCSA, A4 tres DBL3-γ, or ItG2-CS2 DBL2-γ or complements thereof are also contemplated. Other embodiments of varCSA inhibitory or enhancing agents (collectively referred to as "modulators") include antibodies, peptidomimetics, and chemicals that inhibit or enhance adhesion to CSA. Several other methods for identifying agents that modulate the formation of a varCSA-CSA complex can be used. The discussion below describes methods of molecular modeling, combinatorial chemistry, and rational drug design, which can be used to identify molecules that interact with a varCSA molecule and thereby modulate the formation of a varCSA-CSA complex.

Methods of Rational Drug Design

Combinatorial chemistry is the science of synthesizing and testing compounds for bioactivity en masse, instead of one by one, the aim being to discover drugs and materials more quickly and inexpensively than was formerly possible. Although the following describes the use of FCR3.varCSA, fragments thereof and nucleic acids encoding these molecules to conduct rational drug design, it should be understood that these approaches can be used with other molecules that mediate PRBC binding, sequestration, and the onset of maternal malaria, including but not limited to fragments of FCR3.varCSA (e.g., DBL3 and CIDR1), A4 tres DBL3-γ, and ItG2-CS2 DBL2-γ. Thus, the description of FCR3.varCSA, fragments thereof and nucleic acids encoding these molecules are provided for the purposes of explanation and example.

In some embodiments, search programs are employed to compare regions of FCR3.varCSA that modulate the formation of a FCR3 varCSA-CSA complex with other molecules, such as peptides, peptidomimetics, and chemicals so that therapeutic interactions of the molecules can be predicted and new derivative molecules can be designed. In other embodiments, search programs are employed to compare regions of molecules that interact with FCR3.varCSA and, thereby modulate the formation of a FCR3.varCSA-CSA complex, with other molecules such as peptides, peptidomimetics, and chemicals, so that therapeutic interactions of the molecules can be predicted and new derivative FCR3.varCSA modulating agents can be designed. (Schneider, *Genetic Engineering News* December: page 20 (1998), Tempezyk et al., *Molecular Simulations Inc. Solutions* April (1997), and Butenhof, *Molecular Simulations Inc. Case Notes* (August 1998)). This process of directed combinatorial chemistry is referred to as "rational drug design". Libraries of molecules that resemble FCR3.varCSA or interact with FCR3.varCSA and, thereby inhibit or enhance the function of FCR3.varCSA ("modulate" FCR3.varCSA activity) can be created. In some contexts, the term "FCR3.varCSA modulating agent" or "modulators" includes FCR3.varCSA, polypeptide fragments corresponding to FCR3.varCSA, fusion proteins comprising FCR3.varCSA or polypeptide fragments of FCR3.varCSA, nucleic acids encoding these molecules, peptidomimetics, chemicals, and other molecules that mediate PRBC binding, sequestration, and the onset of maternal malaria.

One goal of rational drug design is to produce structural analogs of biologically active polypeptides of interest or of small molecules with which they interact (e.g., agonists, antagonists, null compounds) in order to fashion drugs that are, for example, more or less potent forms of the molecule. (See, e.g., Hodgson, *Bio. Technology* 9:19–21 (1991)). Rational drug design has been used to develop HIV protease inhibitors and agonists for five different somatostatin receptor subtypes. (Erickson et al., *Science* 249:527–533 (1990) and Berk et al., *Science* 282:737 (1998)).

By starting with the sequence or protein models of FCR3.varCSA, and/or fragments thereof, polypeptides having two-dimensional and/or three-dimensional homology can be rapidly identified. In a two-dimensional approach, a percent sequence identity can be determined by standard methods that are commonly used to compare the similarity and position of the amino acid of two polypeptides. Using a computer program such as BLAST or FASTA, two polypeptides are aligned for optimal matching of their respective amino acids (either along the fill length of one or both sequences, or along a predetermined portion of one or both sequences). Such programs provide "default" opening penalty and a "default" gap penalty, and a scoring matrix such as PAM 250 (a standard scoring matrix; see Dayhoff et al., in: Atlas of Protein Sequence and Structure, Vol. 5, Supp. 3 (1978) can be used in conjunction with the computer program. The percent identity can then be calculated as:

$$\frac{\text{(total number of identical matches)}}{\begin{matrix}\text{[length of the longer sequence within the matched span +} \\ \text{number of gaps introduced into the longer sequence} \\ \text{in order to align the two sequences]}\end{matrix}} \times 100$$

Accordingly, the protein sequence corresponding to FCR3.varCSA is compared to known sequences on a protein basis. Protein sequences corresponding to FCR3.varCSA are compared, for example, to known amino acid sequences found in Swissprot release 35, PIR release 53 and Genpept release 108 public databases using BLASTP with the parameter W=8 and allowing a maximum of 10 matches. In addition, the protein sequences encoding FCR3.varCSA are compared to publicly known amino acid sequences of Swissprot using BLASTX with the parameter E=0.001. Because the region involved in CSA binding can be as small as three amino acids, the embodied polypeptides can have the following degrees of homology to FCR3.varCSA: 1.0%, 2.0%, 3.0%, 4.0%, 5.0%, 6.0%, 7.0%, 8.0%, 9.0%, 10.0%, 11.0%, 12.0%, 13.0%, 14.0%, 15.0%, 16.0%, 17.0%, 18.0%, 19.0%, 20.0%, 21.0%, 22.0%, 23.0%, 24.0%, 25.0%, 26.0%, 27.0%, 28.0%, 29.0%, 30.0%, 31.0%, 32.0%, 33.0%, 34.0%, 35.0%, 36.0%, 37.0%, 38.0%, 39.0%, 40.0%, 41.0%, 42.0%, 43.0%, 44.0%, 45.0%, 46.0%, 47.0%, 48.0%, 49.0%, 50.0%, 51.0%, 52.0%, 53.0%, 54.0%, 55.0%, 56.0%, 57.0%, 58.0%, 59.0%, 60.0%, 61.0%, 62.0%, 63.0%, 64.0%, 65.0%, 66.0%, 67.0%, 68.0%, 69.0%, 70.0%, 71.0%, 72.0%, 73.0%, 74.0%, 75.0%, 76.0%, 77.0%, 78.0%, 79.0%, 80.0%, 81.0%, 82.0%, 83.0%, 84.0%, 85.0%, 86.0%, 87.0%, 88.0%, 89.0%, 90.0%, 91.0%, 92.0%, 93.0%, 94.0%, 95.0%, 96.0%, 97.0%, 98.0%, 99.0%, and 100.0% The candidate polypeptides are identified and are subsequently examined using the functional assays described herein. Candidate polypeptides that interact with FCR3.varCSA to modulate the formation of a FCR3.varCSA-CSA complex and thereby effect PRBC adhesion to CSA can be identified in this manner.

Additionally, a search program can be used to compare the three-dimensional structure of FCR3.varCSA or fragments of FCR3.varCSA with other known three-dimensional structures. Once candidate related structures are identified, these molecules can be made recombinantly or by peptide or chemical synthesis. The newly generated compounds are then screened in FCR3.varCSA characterization assays so as to identify modulators that interact with FCR3.varCSA and thereby effect the formation of a FCR3.varCSA-CSA complex.

In the past, the three-dimensional structure of proteins has been determined in a number of ways. Perhaps the best known way of determining protein structure involves the use of x-ray crystallography. A general review of this technique can be found in Van Holde, K. E. Physical Biochemistry, Prentice-Hall, N.J. pp. 221–239 (1971). Using this technique, it is possible to elucidate three-dimensional structure with good precision. Additionally, protein structure can be determined through the use of techniques of neutron diffraction, or by nuclear magnetic resonance (NMR). (See, e.g., Moore, W. J., Physical Chemistry, 4$^{th}$ Edition, Prentice-Hall, N.J. (1972)).

Alternatively, the protein model embodiments of the present invention can be constructed using computer-based protein modeling techniques. By one approach, the protein folding problem is solved by finding target sequences that are most compatible with profiles representing the structural environments of the residues in known three-dimensional protein structures. (See, e.g., Eisenberg et al., U.S. Pat. No. 5,436,850 issued Jul. 25, 1995). In another technique, the known three-dimensional structures of proteins in a given family are superimposed to define the structurally conserved regions in that family. This protein modeling technique also uses the known three-dimensional structure of a homologous protein to approximate the structure of a polypeptide of interest. (See e.g., Srinivasan, et al., U.S. Pat. No. 5,557,535 issued Sep. 17, 1996). Conventional homology modeling techniques have been used routinely to build models of proteases and antibodies. (Sowdhamini et al., Protein Engineering 10:207, 215 (1997)). Comparative approaches can also be used to develop three-dimensional protein models when the protein of interest has poor sequence identity to template proteins. In some cases, proteins fold into similar three-dimensional structures despite having very weak sequence identities. For example, the three-dimensional structures of a number of helical cytokines fold in similar three-dimensional topology in spite of weak sequence homology.

The recent development of threading methods and "fuzzy" approaches now enables the identification of likely folding patterns and functional protein domains in a number of situations where the structural relatedness between target and template(s) is not detectable at the sequence level. By one method, fold recognition is performed using Multiple Sequence Threading (MST) and structural equivalences are deduced from the threading output using the distance geometry program DRAGON that constructs a low resolution model. A full-atom representation is then constructed using a molecular modeling package such as QUANTA.

According to this 3-step approach, candidate templates are first identified by using the novel fold recognition algorithm MST, which is capable of performing simultaneous threading of multiple aligned sequences onto one or more 3-D structures. In a second step, the structural equivalences obtained from the MST output are converted into interresidue distance restraints and fed into the distance geometry program DRAGON, together with auxiliary information obtained from secondary structure predictions. The program combines the restraints in an unbiased manner and rapidly generates a large number of low resolution model confirmations. In a third step, these low resolution model confirmations are converted into full-atom models and subjected to energy minimization using the molecular modeling package QUANTA. (Se e.g., Aszódi et al., Proteins:Structure, Function, and Genetics, Supplement 1:38–42 (1997)).

In one approach, a three-dimensional structure of a polypeptide of interest (e.g., FCR3.varCSA, and/or fragments thereof or a FCR3.varCSA modulating agent) is determined by x-ray crystallography, NMR, or neutron diffraction and computer modeling, as described above. Useful protein models of the polypeptide of interest can also be gained by computer modeling alone. Combinatorial chemistry can then be employed to design derivatives of the polypeptide of interest based on the three-dimensional models. The candidate FCR3.varCSA modulating agents are then tested in functional assays. The assays, described herein and assays that evaluate the formation of a FCR3.varCSA-CSA complex in the presence of FCR3.varCSA or fragments thereof that will be apparent to one of skill in the art given the disclosure herein (referred to collectively as "FCR3.varCSA characterization assays") are performed on the FCR3.varCSA modulating agents and groups of FCR3.varCSA modulating agents (wherein the grouping is based on the potency of modulation of the formation of a FCR3.varCSA-CSA complex) are identified and recorded on a computer readable media. Further cycles of modeling and FCR3.varCSA characterization assays can be employed to more narrowly define the parameters needed in an optimal FCR3.varCSA modulating agent.

By another approach, a FCR3.varCSA modulating agent that interacts with FCR3.varCSA can be manufactured and identified as follows. First, a molecular model of one or more FCR3.varCSA modulating agents or portions of FCR3.varCSA modulating agents that interact with FCR3.varCSA are created using one of the techniques discussed above or as known in the art. FCR3.varCSA modulating agents that are known to interact with FCR3.varCSA include antibodies and fragments of CSA. Next, chemical libraries and databases are searched for molecules similar in structure to the known FCR3.varCSA modulating agents. Identified candidate FCR3.varCSA modulating agents are then screened in the FCR3.varCSA characterization assays, described above, and the agents that produce the desired response are used as templates for further library construction. Libraries of FCR3.varCSA modulating agents are synthesized on solid support beads by split-and-pool synthesis, a multistage process for producing very large numbers of compounds. The support-bound agents are then used in FCR3.varCSA characterization assays or "free mixtures" are created by cleaving the agent from the support and these free mixtures are screened in the FCR3.varCSA characterization assays. Compounds that produce desirable responses are identified, recorded on a computer readable media, and the process is repeated to select optimal FCR3.varCSA modulating agents.

Each FCR3.varCSA modulating agent and its response in a FCR3.varCSA characterization assay can be recorded on a computer readable media and a database or library of FCR3.varCSA modulating agents and respective responses in the FCR3.varCSA characterization assay can be generated. These databases or libraries can be used by researchers to identify important differences between active and inactive molecules so that compound libraries are enriched for FCR3.varCSA modulating agents that have favorable characteristics. Further, enrichment can be achieved by using approaches in dynamic combinatorial chemistry. (See e.g., Angnew, *Chem. Int. Ed.,* 37:2828 (1998)). For example, a target biomolecule, such as FCR3.varCSA, is joined to a support and is bound by the FCR3.varCSA modulating agents from the libraries generated above. The FCR3.varCSA resin bound with one or more candidate FCR3.varCSA modulating agents is removed from the binding reaction, the FCR3.varCSA modulating agents are eluted from the support, and are identified. Cycles of immobilized target binding assays are conducted, classes of FCR3.varCSA modulating agents that exhibit desired binding characteristics are identified, and this data is recorded on a computer readable media and is used to select more FCR3.varCSA modulating agents that produce a desired modulation of the formation of a FCR3.varCSA-CSA complex.

In addition, a peptide of interest (e.g., FCR3.varCSA, and/or fragments thereof or a FCR3.varCSA modulating agent) can be analyzed by an alanine scan (Wells, Methods in Enzymol. 202:390–411 (1991)) or other types of site-directed mutagenesis analysis. In alanine scan, for example, an amino acid residue is replaced by alanine, and its affect on the peptide's activity is measured by functional assays, such as the FCR3.varCSA characterization assays described herein. Each of the amino acid residues of the peptide is analyzed in this manner and the regions important for a specific modulation of the formation of a FCR3.varCSA-CSA complex are identified. Subsequently, these functionally important regions are recorded on a computer readable medium, stored in a first database in a computer system, and a search program is employed to generate protein models of the functionally important regions. Once protein models of the functionally important regions have been generated, a second database comprising one or more libraries having peptides, chemicals, peptidomimetics and other agents is accessed by a search program and individual agents are compared to the protein models to identify agents that comprise homologous regions or domains that resemble the identified functionally important regions. Agents identified by the approach above are then tested in the FCR3.varCSA characterization assays and are used to construct multimeric agents and/or are incorporated into pharmaceuticals, as detailed below.

In another embodiment, computer modeling and the sequence-to-structure-to-function paradigm is exploited to identify more FCR3.varCSA modulating agents that modulate the formation of a FCR3.varCSA-CSA complex. By this approach, first the structure of a FCR3.varCSA modulating agent having a known response in a FCR3.varCSA characterization assay (e.g., FCR3.varCSA, and fragments thereof, and antibodies to FCR3.varCSA, is determined from its sequence using a threading algorithm, which aligns the sequence to the best matching structure in a structural database. Next, the protein's active site (i.e., the site important for a desired response in the FCR3.varCSA characterization assay) is identified and a "fuzzy functional form" (FFF)— a three-dimensional descriptor of the active site of a protein—is created. (See e.g., Fetrow et al., *J Mol. Biol.* 282:703–711 (1998) and Fetrow and Skolnick, *J. Mol. Biol.* 281: 949–968 (1998)).

The FFFs are built by itteratively superimposing the protein geometries from a series of functionally related proteins with known structures. The FFFs are not overly specific, however, and the degree to which the descriptors can be relaxed is explored. In essence, conserved and functionally important residues for a desired response are identified and a set of geometric and conformational constraints for a specific function are defined in the form of a computer algorithm. The program then searches experimentally determined protein structures from a protein structural database for sets of residues that satisfy the specified constraints. In this manner, homologous three-dimensional structures can be compared and degrees (e.g., percentages of three-dimensional homology) can be ascertained.

By using this computational protocol, genome sequence data bases such as maintained by various organizations including: www.tigr.org/tdb; www.genetics.wisc.edu; www.stanford.edu/~ball; hiv-web.lanl.gov; www.ncbi.nlm.nih.gov; www.ebi.ac.uk; pasteur.fr/other/biology; and www.genome.wi.mit.edu, can be rapidly screened for specific protein active sites and for identification of the residues at those active sites which resemble a desired molecule.

Several other groups have developed databases of short sequence patterns or motifs designed to identify a given function or activity of a protein. These databases, notably Prosite (expasy.hcuge.ch/sprot/prosite.html. Blocks (www.blocks.fhcrc.org); and Prints (www.biochem.ucl.ac.uk/bsm/dbbrowser/PRINTS/PRINTS.html), uses short stretches of sequence information to identify sequence patterns that are specific for a given function; thus they avoid the problems arising from the necessity of matching entire sequences. In this manner, new FCR3.varCSA modulating agents are rationally selected for further identification by FCR3.varCSA characterization assays, as described above. Rounds or cycles of functional assays on the molecules and derivatives thereof and further FFF refinement and database searching allows an investigator to more narrowly define classes of FCR3.varCSA modulating agents that produce a desired modulation of the formation of a FCR3.varCSA-CSA complex.

Many computer programs and databases can be used with embodiments of the invention to identify agents that modulate FCR3.varCSA-mediated adhesion to CSA. The following list is intended not to limit the invention but to provide guidance to programs and databases that are useful with the approaches discussed above. The programs and databases that may be used include, but are not limited to: MacPattern (EMBL), DiscoveryBase (Molecular Applications Group), GeneMine (Molecular Applications Group), Look (molecular Applications Group), MacLook (Molecular Applications Group), BLAST and BLAST2 (NCBI), BLASTN and BLASTX (Altschul et al, *J. Mol. Biol.* 215: 403 (1990)), FASTA Pearson and Lipman, *Proc. Natl. Acad. Sci. USA,* 85:2444 (1988)), Catalyst (Molecular Simulations Inc.), Catalyst/SHAPE (Molecular Simulations Inc.), Cerius$^2$DBAccess (Molecular Simulations Inc.), HypoGen (Molecular Simulations Inc.), Insight II, (Molecular Simulations Inc.), Discover (Molecular Simulations Ic.), CHARMm (Molecular Simulations Inc.), Felix (Molecular Simulations Inc.), DelPhi, (Molecular Simulations Inc.), QuanteMM, (Molecular Simulations Inc.), Homology (Molecular Simulations Inc.), Modeler (Molecular Simulations Inc.), Modeller 4 (Sali and Blundell J. Mol. Biol. 234:217–241 (1997)), ISIS (Molecular Simulations Inc.), Quanta/Protein Design (Molecular Simulations Inc.), WebLab Molecular Simulations Inc.), WebLab Diversity Explorer (Molecular Simulations Inc.), Gene Explorer (Molecular Simulations Inc.), SeqFold (Molecular Simulations Inc.), the EMBL/Swissprotein database, the MDL Available Chemicals Directory database, the MDL Drug Data Report data base, the Comprehensive Medicinal Chemistry database, Derwents's World Drug Index database, and the BioByteMasterFile database. Many other programs and data bases would be apparent to one of skill in the art given the present disclosure.

Libraries of information on FCR3.varCSA modulating agents with their corresponding response in FCR3.varCSA characterization assays can be generated by performing the rational drug design approaches above in conjunction with the FCR3.varCSA characterization assays. A record of the results for each FCR3.varCSA modulating agent is generated and groups of FCR3.varCSA modulating agents are identified and stored on a computer readable media. Databases of this information are valuable to investigators and clinicians for selecting the type of FCR3.varCSA modulating agent-based pharmaceutical to treat or elicit a particular response. Preferable libraries are created by performing the assays above on FCR3.varCSA and fragments thereof.

Many of the FCR3.varCSA modulating agents are provided in biotechnological tools, diagnostics, and pharmaceuticals as multimeric or multimerized agents or both that can be joined to a support. In the disclosure below, we discuss the preparation of multimeric supports and multimerized FCR3.varCSA modulating agents comprising FCR3.varCSA or fragments of FCR3.varCSA, complementary nucleic acids to FCR3.varCSA, FCR3.varCSA or fragments of FCR3.varCSA, antibodies or antibody fragments that recognize epitopes of FCR3.varCSA, and FCR3.varCSA fusion proteins.

Preparation of Multimeric Supports and Multimerized FCR3.varCSA Modulators

Biotechnological tools and components to prophylactic and therapeutic agents desirably provide FCR3.varCSA, fragments of FCR3.varCSA, A4 tres DBL3-γ, or ItG2-CS2 DBL2-γ antibodies or antibody fragments that recognize epitopes on these molecules, fusion proteins containing these molecules, nucleic acids encoding these molecules (and complementary nucleic acids thereof) in such a form or in such a way that a sufficient affinity, modulation of a varCSA-CSA complex formation or induction of an immune response is achieved. While a natural monomeric agent (that is, an agent that presents a discrete molecule, thus, carrying only one binding epitope or domain) can be sufficient to achieve a desired response, a synthetic agent or a multimeric agent (that is, an agent that presents multiple molecules, thus, having several binding epitopes or domains) often times can elicit a greater response. It should be noted that the term "multimeric" refers to the presence of more than one molecule on an agent, for example, several individual molecules of an antibody joined to a support, as distinguished from the term "multimerized" that refers to an agent that has more than one molecule joined as a single discrete compound molecule on a support, for example several antibody molecules joined to form a single compound molecule that is joined to a support.

A multimeric agent (synthetic or natural) that modulates the formation of a a varCSA-CSA complex or induces an immune response is obtained by joining FCR3.varCSA, fragments of FCR3.varCSA, A4 tres DBL3-γ, or ItG2-CS2 DBL2-γ antibodies or antibody fragments that recognize epitopes on these molecules, fusion proteins containing these molecules, nucleic acids encoding these molecules (and complementary nucleic acids thereof), collectively referred to as "FCR3.varCSA modulating agents", "varCSA modulating agents" or "modulators", to a macromolecular support. These modulating agents including peptidomimetics and chemical molecules that resemble these ligands are also joined to supports so as to create the multimeric agents of the invention. A "support" can also be a carrier, a protein, a resin or any macromolecular structure used to join or immobilize a FCR3.varCSA modulating agent. Solid supports include, but are not limited to, the walls of wells of a reaction tray, test tubes, polystyrene beads, magnetic beads, nitrocellulose strips, membranes, microparticles such as latex particles, sheep (or other animal) red blood cells, Duracyte® artificial cells, and others. In several embodiments, the macromolecular support has a hydrophobic surface that interacts with a portion of the varCSA modulating agent by a hydrophobic non-covalent interaction. In some cases, the hydrophobic surface of the support is a polymer such as plastic or any other polymer in which hydrophobic groups have been linked such as polystyrene, polyethylene or polyvinyl. Additionally, the varCSA modulating agent is covalently bound to carriers including proteins and oligo/polysaccarides (e.g. cellulose, starch, glycogen, chitosane or aminated sepharose). In these later embodiments, a reactive group on a FCR3.varCSA modulating agent, such as a hydroxy or an amino group, is used to join to a reactive group on the carrier so as to create the covalent bond. Embodiments also comprise a support with a charged surface that interacts with the varCSA modulating agent. Additional embodiments comprise a support that has other reactive groups that are chemically activated so as to attach a varCSA modulating agent, such as a peptide or chemical compound. For example, cyanogen bromide activated matrices, epoxy activated matrices, thio and thiopropyl gels, nitrophenyl chloroformate and N-hydroxy succinimide chlorformate linkages, or oxirane acrylic supports are used. (Sigma).

Inorganic carriers, such as silicon oxide material (e.g. silica gel, zeolite, diatomaceous earth or aminated glass) to which the varCSA modulating agent is covalently linked through a hydroxy, carboxy or amino group and a reactive group on the carrier are also embodiments. Carriers for use in the body, (i.e. for prophylactic or therapeutic applications) are desirably physiological, non-toxic and preferably, non-immunoresponsive. Contemplated carriers for use in the body include poly-L-lysine, poly-D, L-alanine and Chromosorb® (Johns-Manville Products, Denver Co.). Conjugated Chromosorb® (Synsorb-Pk) has been tested in humans for the prevention of hemolytic-uremic syndrome and was reported as not presenting adverse reactions. (*Armstrong et al. J. Infectious Diseases* 171:1042–1045 (1995)). For some embodiments, the administration of a "naked" carrier (i.e., lacking an attached varCSA modulating agent) that has the capacity to attach a varCSA modulating agent that modulates the formation of a varCSA-CSA complex inside the body of a subject is performed. By this approach, a "prodrug-type" therapy is administered in which the naked carrier is provided separately from the desired varCSA modulating agent and, once both are in the body, the carrier and the varCSA modulating agent assemble into a multimeric complex and modulate the formation of a varCSA-CSA complex.

In another embodiment, linkers, such as λ linkers, of an appropriate length are inserted between the varCSA modulating agent and the support so as to encourage greater flexibility in the varCSA modulating agent and thereby overcome any steric hindrance that is presented by the support. The determination of an appropriate length of linker that allows for optimal binding and modulation of the formation of a varCSA-CSA complex, is made by screening the varCSA modulating agents with varying linkers in the varCSA characterization assays.

A composite support having more than one type of varCSA modulating agent is also an embodiment. A "composite support" is a carrier, a resin, or any macromolecular structure used to join or immobilize two or more different varCSA modulating agents that modulate the formation of a varCSA-CSA complex. The composite supports are also constructed by utilizing hydrophobic interactions and covalent linkages formed through reactive groups, as detailed above. Further, linkers, such as λ linkers, of an appropriate length between the varCSA modulating agents and the support are inserted in some embodiments so as to encourage greater flexibility in the molecule and overcome steric hindrance. The determination of an appropriate length of linker that allows for optimal binding and modulation of the formation of a varCSA-CSA complex, is made by screening the varCSA modulating agents with varying linkers in the varCSA characterization assays detailed in the present disclosure.

In other embodiments, the multimeric and composite supports discussed above have attached multimerized varCSA modulating agents so as to create a "multimerized-multimeric support" and a "multimerized-composite support", respectively. An embodiment of a multimerized varCSA modulating agent, for example, is obtained by creating an expression construct having two or more nucleotide sequences encoding the varCSA modulating agent joined together by using conventional techniques in molecular biology. The expressed fusion protein is one embodiment of a multimerized agent and is then joined to a support. A support having many such multimerized agents is termed a multimerized-multimeric support. The multimerized form of the varCSA modulating agent can be advantageous for many applications because of the ability to obtain an agent with a better ability to modulate the formation of a varCSA-CSA complex. The incorporation of linkers or spacers, such as flexible λ linkers, between the protein domains that make-up the multimerized agent can also be advantageous for some embodiments. The insertion of λ linkers of an appropriate length between protein binding domains, for example, encourages greater flexibility in the molecule and overcomes steric hindrance between the several proteins. Similarly, the insertion of linkers between the multimerized varCSA modulating agent and the support encourages greater flexibility and reduces steric hindrance presented by the support. The determination of an appropriate length of linker that allows for optimal binding and modulation of the formation of a varCSA-CSA complex can be accomplished by screening the varCSA modulating agents with varying linkers in the varCSA characterization assays detailed in this disclosure. In a similar fashion composite-multimerized-multimeric supports with and without linkers can be constructed by joining more than one different multimerized varCSA modulating agent to a support. The discussion that follows describes several diagnostic embodiments.

Diagnostic Embodiments

Several diagnostic and prognostic tools that detect the concentration and expression level of nucleic acids encoding a varCSA molecule (e.g., FCR3.varCSA) and the concentration and expression level of a varCSA molecule (e.g., FCR3.varCSA) in various tissues and fluids are used to determine whether an individual is suffering from maternal malaria or is likely to suffer from maternal malaria. Generally, the diagnostics and methods of use thereof can be classified according to whether the diagnostic detects the concentration or expression level of a nucleic acid or protein in a biological sample (e.g., blood). Accordingly, in some embodiments, the concentration and expression level of FCR3.varCSA in a biological sample can be determined by monitoring the amount of RNA in the sample. The detection of RNA encoding FCR3.varCSA in a sample indicates the existence or predilection to maternal malaria. Further, a detection of DNA encoding FCR3.varCSA in a biological sample indicates the existence or predilection to maternal malaria. Similarly, the concentration and expression level of FCR3.varCSA in a biological sample can be determined by monitoring the amount of FCR3.varCSA protein in the sample. The detection of FCR3.varCSA in a sample indicates the existence or predilection to maternal malaria. Other diagnostic approaches involve the detection of A4 tres DBL3-γ or ItG2-CS2 DBL2-γ and the detection of antibodies to FCR3.varCSA, fragments of FCR3.varCSA, A4 tres DBL3-γ, or ItG2-CS2 DBL2-γ.

For example, to determine the presence of FCR3.varCSA or FCR3.varCSA in a subject, first a biological sample is obtained. Several methods known to those in the art can be employed to obtain a biological sample having red blood cells (e.g., phlebotomy). Once a biological sample from a subject in need of testing is obtained, many different techniques can be used to detect the concentration and expression level of FCR3.varCSA or FCR3.varCSA including, but not limited to, antibody-based detection techniques (e.g., ELISA, sandwich assays, immunoprecipitation, and immunoblots), bacteriophage display techniques, hybridization techniques (e.g., Southern and Northern), and enzymatic digestion (e.g., RNAse protection) techniques. Some of these techniques can involve disposing the proteins and/or nucleic acids present in the biological sample on a support, and contacting the support with detection reagents such as antibodies to FCR3.varCSA or nucleic acid probes complementary to FCR3.varCSA mRNA. Desirably, the levels of expression or concentration of FCR3.varCSA or FCR3.varCSA or both from diseased and healthy individuals is compared to the level detected in the subject tested. Similar approaches can be used to detect A4 tres DBL3-γ, or ItG2-CS2 DBL2-γ or nucleic acids encoding these molecules.

In preferred embodiments, the nucleic acid embodiments are attached to a support in an ordered array wherein a plurality of nucleic acid probes are attached to distinct regions of the support that do not overlap with each other. Preferably, such an ordered array is designed to be "addressable" where the distinct locations of the probe are recorded and can be accessed as part of an assay procedure. In some embodiments, addressable nucleic acid arrays comprise a plurality of nucleic acid probes that complement a nucleic acid encoding FCR3.varCSA, fragments of FCR3.varCSA, A4 tres DBL3-γ, or ItG2-CS2 DBL2-γ. These probes are joined to a support in different known locations. The knowledge of the precise location of each nucleic acid probe makes these "addressable" arrays particularly useful in binding assays.

For example, an addressable array can comprise a support having several regions to which are joined a plurality nucleic acid probes that complement FCR3.varCSA. The nucleic acids from a preparation of several biological samples from a plurality of human subjects or a plurality of tissues or fluids from a single subject are labeled by conventional approaches (e.g., radioactivity or fluorescence) and the labeled samples are applied to the array under conditions that permit hybridization. If a nucleic acid in the sample hybridizes to a probe on the array, then a signal will be detected at a position on the support that corresponds to the location of the hybrid. Since the identity of each labeled sample is known and the region of the support on which the labeled sample was applied is known, an identification of the presence, concentration, and/or expression level can be rapidly determined. That is, by employing labeled standards of a known concentration of a nucleic acid encoding FCR3.varCSA, (e.g., RNA), an investigator can accurately determine the concentration of a nucleic acid encoding FCR3.varCSA in a sample and from this information can assess the expression level of FCR3.varCSA. Conventional methods in densitometry can also be used to more accurately determine the concentration or expression level of a nucleic acid encoding FCR3.varCSA. These approaches are easily automated using technology known to those of skill in the art of high throughput diagnostic analysis.

Additionally, an opposite approach to that presented above can be employed. Nucleic acids present in biological samples (e.g., tissues or fluids from one or more subjects or one or more sources in a subject's body) can be disposed on a support so as to create an addressable array. Preferably, the samples are disposed on the support at known positions that do not overlap. The presence of nucleic acids encoding FCR3.varCSA in each sample is determined by applying labeled nucleic acid probes that complement nucleic acids that encode FCR3.varCSA and detecting the presence of a signal at locations on the array that correspond to the positions at which the biological samples were disposed. Because the identity of the biological sample and its position on the array is known, an identification of the presence, concentration, and/or expression level of a nucleic acid encoding FCR3.varCSA is rapidly determined. That is, by employing labeled standards of a known concentration of a nucleic acid encoding FCR3.varCSA, (e.g., RNA), an investigator can accurately determine the concentration of a nucleic acid encoding FCR3.varCSA in a sample and from this information can assess the expression level of FCR3.varCSA. Conventional methods in densitometry can also be used to more accurately determine the concentration or expression level of a nucleic acid encoding FCR3.varCSA. These approaches are also easily automated using technology known to those of skill in the art of high throughput diagnostic analysis. Similar approaches can be used to determine the presence, absence, or amount of a nucleic acid encoding A4 tres DBL3-γ or ItG2-CS2 DBL2-γ.

Any addressable array technology known in the art can be employed with this aspect of the invention. One particular embodiment of polynucleotide arrays is known as Genechips™, and has been generally described in U.S. Pat. No. 5,143,854; PCT publications WO 90/15070 and 92/10092. These arrays are generally produced using mechanical synthesis methods or light directed synthesis methods, which incorporate a combination of photolithographic methods and solid phase oligonucleotide synthesis. (Fodor et al., *Science,* 251:767–777, (1991)). The immobilization of arrays of oligonucleotides on solid supports has been rendered possible by the development of a technology generally identified as "Very Large Scale Immobilized Polymer Synthesis" (VLSIPS™) in which, typically, probes are immobilized in a high density array on a solid surface of a chip. Examples of VLSIPS™ technologies are provided in U.S. Pat. Nos. 5,143,854 and 5,412,087 and in PCT Publications WO 90/15070, WO 92/10092 and WO 95/11995, which describe methods for forming oligonucleotide arrays through techniques such as light-directed synthesis techniques. In designing strategies aimed at providing arrays of nucleotides immobilized on solid supports, further presentation strategies were developed to order and display the oligonucleotide arrays on the chips in an attempt to maximize hybridization patterns and diagnostic information. Examples of such presentation strategies are disclosed in PCT Publications WO 94/12305, WO 94/11530, WO 97/29212 and WO 97/31256.

A wide variety of labels and conjugation techniques are known by those skilled in the art and can be used in various nucleic acid assays. There are several ways to produce labeled nucleic acids for hybridization or PCR (Polymerase Chain Reaction) including, but not limited to, oligolabeling, nick translation, end-labeling, or PCR amplification using a labeled nucleotide. Alternatively, a nucleic acid encoding FCR3.varCSA, or any portion of it, can be cloned into a vector for the production of an rRNA probe. Such vectors are known in the art, are commercially available, and can be used to synthesize RNA probes in vitro by addition of an appropriate RNA polymerase such as T7, T3 or SP6 and labeled nucleotides. A number of companies such as Pharmacia Biotech (Piscataway N.J.), Promega (Madison Wis.), and U.S. Biochemical Corp (Cleveland Ohio) supply commercial kits and protocols for these procedures. Suitable reporter molecules or labels include those radionuclides, enzymes, fluorescent, chemiluminescent, or chromogenic agents, as well as, substrates, cofactors, inhibitors, magnetic particles and the like.

For diagnostic and prognostic purposes, nucleic acid probes having a sequence that complements a nucleic acid encoding FCR3.varCSA, fragments of FCR3.varCSA, A4 tres DBL3-γ, or ItG2-CS2 DBL2-γ or a portion thereof can be used to detect and quantitate gene expression in biological samples. Preferably, nucleic acid probes that are complementary to mRNA encoding FCR3.varCSA, fragments of FCR3.varCSA, A4 tres DBL3-γ, or ItG2-CS2 DBL2-γ are used to screen for polynucleotides present in blood. RNA-detection-based diagnostic assays, such as Northern hybridization, Northern dot blots, RNA in situ hybridization, and ELISA assays, are particularly useful to distinguish between the absence or presence of these mRNAs and/or to monitor mRNA levels during therapeutic intervention.

Embodiments also include the use of oligonucleotide sequences, antisense RNA and DNA molecules, and PNAs that complement a nucleic acid encoding FCR3.varCSA, fragments of FCR3.varCSA, A4 tres DBL3-γ, or ItG2-CS2 DBL2-γ for the determination of the concentration and expression level in the cells of a subject by RNA-based detection techniques. The form of such qualitative and/or quantitative methods can include Northern analysis, dot blot or other membrane-based technologies; PCR technologies; dip stick, pin, chip, and ELISA technologies. All of these techniques are well known in the art and are the basis of many commercially available diagnostic kits.

In one aspect, RNA probes complementary to FCR3.varCSA mRNA are used in assays that detect maternal malaria. Accordingly, the nucleotide sequence encoding FCR3.varCSA or a fragment thereof is used to design suitable RNA probes. The RNA probes are labeled by methods known in the art and are added to a DNAse treated fluid or tissue sample from a subject under conditions suitable for the formation of hybridization complexes. Hybridization complexes are isolated or the sample is treated with an agent that removes unhybridized nucleic acids. After an incubation period, the sample is washed with a compatible fluid that optionally contains a dye (or other label requiring a developer) if the nucleotide has been labeled with an enzyme. After the compatible fluid is rinsed off, the dye is quantitated and compared with a standard. If the amount of dye in the sample is significantly elevated over that of a comparable control sample, the nucleotide sequence has hybridized with RNA in the sample, and the presence of elevated levels of RNA encoding FCR3.varCSA or a portion thereof in the sample indicates the presence of a FCR3.varCSA-related disease, such as cancer. A similar approach can be used to determine the presence, absence or amount of an mRNA encoding A4 tres DBL3-γ, or ItG2-CS2 DBL2-γ.

Such assays can also be used to evaluate the efficacy of a particular therapeutic treatment regime in animal studies, in clinical trials, or in monitoring the treatment of an individual patient. In order to provide a basis for the diagnosis of disease, a normal or standard profile for FCR3.varCS4 expression in isolated cells, extracts, or tissue can be established, for example. This is accomplished by combining body fluids or cell extracts taken from healthy subjects with RNA probes encoding FCR3.varCSA, or a portion thereof, under conditions suitable for hybridization. Standard hybridization can be quantified by comparing the values obtained for healthy and diseased subjects with a dilution series of FCR3.varCSA RNA run in the same experiment where a known amount of substantially purified FCR3.varCSA is used. Standard values obtained from samples from healthy and diseased subjects are then compared with values obtained from samples from the tested subjects. Deviation between standards and the values obtained for the subject tested establishes the presence or predilection for material malaria. A similar approach can be based on a profile constructed from the presence or amount of mRNA encoding A4 tres DBL3-γ, or ItG2-CS2 DBL2-γ from healthy and diseased individuals.

Additionally, PCR methods that can be used to quantitate the concentration and expression level of a particular molecule include radiolabeling (Melby P. C. et al. J Immunol Methods 159:235–44 (1993)) or biotinylating nucleotides (Duplaa C. et al. Anal Biochem 212:229–236 (1993)), coamplification of a control nucleic acid, and standard curves onto which the experimental results are interpolated. Quantitation of multiple samples can be processed more rapidly by running the assay in an ELISA format where the oligomer of interest is presented in various dilutions and a spectrophotometric or colorimetric response gives rapid quantitation. A definitive diagnosis of this type can allow health professionals to create a disease state profile for a patient, begin aggressive treatment for the malaria, and prevent further worsening of the condition. Similarly, further assays and reference to the changing disease state profile can help clinicians monitor the progress of a patient during treatment. That is, once a disease state is established, a therapeutic agent is administered and an initial disease state profile is generated. The assays above can be repeated on a regular basis to evaluate whether the values in the subject's disease state profile progresses toward or returns back to the initial disease state profile. Successive treatment profiles can be used to show the efficacy of treatment over a period of several days or several months.

As mentioned above, PCR technology can be used to identify and quantitate concentration and expression levels of a nucleic acid encoding FCR3.varCSA, fragments of FCR3.varCSA, A4 tres DBL3-γ, or ItG2-CS2 DBL2-γ. For amplification of mRNAs, it is within the scope of the present invention to reverse transcribe mRNA into cDNA followed by PCR (RT-PCR); or, to use a single enzyme for both steps as described in U.S. Pat. No. 5,322,770, or, to use Reverse Transcriptase Asymmetric Gap Ligase Chain Reaction (RT-AGLCR), as described by Marshall R. L. et al. (*PCR Methods and Applications* 4:80–84, 1994).

A variety of PCR techniques are familiar to those skilled in the art. For a review of PCR technology, see Molecular Cloning to Genetic Engineering White, B. A. Ed. in *Methods in Molecular Biology* 67: Humana Press, Totowa (1997) and the publication entitled "PCR Methods and Applications" (1991, Cold Spring Harbor Laboratory Press). In each of these PCR procedures, PCR primers on either side of the sequence to be amplified are added to a suitably prepared nucleic acid sample along with dNTPs and a thermostable polymerase such as Taq polymerase, Pfu polymerase, or Vent polymerase. The nucleic acid in the sample is denatured and the PCR primers are specifically hybridized to complementary nucleic acid sequences in the sample. The hybridized primers are extended. Thereafter, another cycle of denaturation, hybridization, and extension is initiated. The cycles are repeated multiple times to produce an amplified fragment containing the nucleic acid sequence between the primer sites. PCR has further been described in several patents including U.S. Pat. Nos. 4,683,195, 4,683,202 and 4,965,188.

The primers are selected to be substantially complementary to a portion of the sequence of a nucleic acid encoding FCR3.varCSA, fragments of FCR3.varCSA, A4 tres D13L3-γ, or ItG2-CS2 DBL2-γ and a portion of the sequence that complements the sequence of FCR3.varCSA, fragments of FCR3.varCSA, A4 tres DBL3-γ, or ItG2-CS2 DBL2-γ mRNA, thereby allowing the sequences between the primers to be amplified. The length of the primers for use with this aspect of the present invention be identical to most of the lengths of the nucleic acid embodiments provided previously. That is, primer length can be less than or equal to 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 40, 41, 42, 43, 44, 45, 46, 47, 48, 49, 50, 51, 52, 53, 54, 55, 56, 57, 5.8, 59, 60, 61, 62, 63, 64, 65, 66, 67, 68, 69, 76, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 250, 300, 350, 400, 500, 600, 700, 800, 900, 1000, 1500, 2000, 3000, 4000, 5000, 6000, 7000, 8000, 9000, 10,000, and 10,500 nucleotides. Preferably, however primers are 16, 17, 18, 19, 20, 21, 22, 23, 24, 25, 26, 27, 28, 29 and 30 nucleotides in length. Shorter primers tend to lack specificity for a target nucleic acid sequence and generally require cooler temperatures to form sufficiently stable hybrid complexes with the template. Longer primers are expensive to produce and can sometimes self-hybridize to form hairpin structures. The formation of stable hybrids depends on the melting temperature (Tm) of the DNA. The Tm depends on the length of the primer, the ionic strength of the solution and the G+C content. The higher the G+C content of the primer, the higher is the melting temperature because G:C pairs are held by three H bonds whereas A:T pairs have only two. The G+C content of the amplification primers of the present invention preferably ranges between 10 and 75%, more preferably between 35 and 60%, and most preferably between 40 and 55%. The appropriate length for primers under a particular set of assay conditions may be empirically determined by one of skill in the art.

The spacing of the primers determines the length of the segment to be amplified. In the context of the present invention amplified segments carrying nucleic acid sequence encoding fragments of FCR3.varCSA, fragments of FCR3.varCSA, A4 tres DBL3-γ, or ItG2-CS2 DBL2-γ can range in size from at least about 25 bp to 35 kbp. Amplification fragments from 25–3000 bp are typical, fragments from 50–1000 bp are preferred and fragments from 100–600 bp are highly preferred. It will be appreciated that amplification primers for a nucleic acid encoding FCR3.varCSA, fragments of FCR3.varCSA, A4 tres DBL3-γ, or ItG2-CS2 DBL2-γ can be of any sequence that allows the specific amplification of any DNA fragment carrying nucleic acid sequence unique these molecules. Amplification primers can be labeled or immobilized on a solid support as described above.

The presence of FCR3.varCSA, A4 tres DBL3-γ, or ItG2-CS2 DBL2-γ protein can be detected by screening for the presence of the protein using conventional assays. For example, monoclonal antibodies immunoreactive with FCR3.varCSA can be used to screen biological samples for the presence, concentration, and expression level of FCR3.varCSA and, thereby, provide diagnostic information about FCR3.varCSA-related diseases. Such immunological assays can be done in many convenient formats.

In one embodiment, for example, antibodies are used to immunoprecipitate FCR3.varCSA, fragments of FCR3.varCSA, A4 tres DBL3-γ, or ItG2-CS2 DBL2-γ from solution and, in another embodiment, antibodies are used to react with FCR3.varCSA on Western or Immunoblots of a polyacrylamide gel. In desirable embodiments, antibodies are used to detect FCR3.varCSA, fragments of FCR3.varCSA, A4 tres DBL3-γ, or ItG2-CS2 DBL2-γ in paraffin or frozen sections, using immunocytochemical techniques. Favored embodiments for detecting FCR3.varCSA, fragments of FCR3.varCSA, A4 tres DBL3-γ, or ItG2-CS2 DBL2-γ include enzyme-linked immunosorbant assays (ELISA), radioimmunoassays (RIA), immunoradiometric assays (IRMA) and immunoenzymatic assays (IEMA), including sandwich assays using monoclonal and/or polyclonal antibodies. Exemplary sandwich assays are described by David et al., in U.S. Pat. Nos. 4,376,110 and 4,486,530.

In preferred protein-based diagnostic embodiments, antibodies of the present invention are attached to a support in an ordered array wherein a plurality of antibodies are attached to distinct regions of the support that do not overlap with each other. As with the nucleic acid-based arrays, the protein-based arrays are ordered arrays that are designed to be "addressable" such that the distinct locations are recorded and can be accessed as part of an assay procedure.

For example, in some embodiments, addressable antibody arrays comprise a plurality of antibodies that recognize FCR3.varCSA These probes are joined to a support in different known locations. The knowledge of the precise location of each probe makes these "addressable" arrays particularly useful in binding assays. For example, an addressable array can comprise a support having several regions to which are joined a plurality antibody probes that recognize FCR3.varCSA. Proteins from a preparation of several biological samples from a plurality of human subjects or a plurality of tissues or fluids from a single subject are labeled by conventional approaches (e.g., radioactivity, calorimetrically, or fluorescently) and the labeled samples are applied to the array under conditions that permit binding. If a protein in the sample binds to an antibody probe on the array, then a signal will be detected at a position on the support that corresponds to the location of the antibody-protein complex. Since the identity of each labeled sample is known and the region of the support on which the labeled sample was applied is known, an identification of the presence, concentration, and/or expression level is rapidly determined. That is, by employing labeled standards of a known concentration of FCR3.varCSA, an investigator can accurately determine the protein concentration of FCR3.varCSA in a sample and from this information can assess the expression level of FCR3.varCSA. Conventional methods in densitometry can also be used to more accurately determine the concentration or expression level of FCR3.varCSA. These approaches are easily automated using technology known to those of skill in the art of high throughput diagnostic analysis.

In another embodiment, an opposite approach to that presented above can be employed. Proteins present in biological samples (e.g., tissues or fluids from one or more subjects or one or more sources in a subject's body) can be disposed on a support so as to create an addressable array. Preferably, the protein samples are disposed on the support at known positions that do not overlap. The presence of a protein encoding FCR3.varCSA in each sample is then determined by applying labeled antibody probes that recognize epitopes of FCR3.varCSA and detecting a signal at locations on the array that correspond to the positions at which the biological samples were disposed. Because the identity of the biological sample and its position on the array is known, an identification of the presence, concentration, and/or expression level FCR3.varCSA is rapidly determined. That is, by employing labeled standards of a known concentration of FCR3.varCSA, an investigator can accurately determine the concentration of FCR3.varCSA in a sample and from this information can assess the expression level of FCR3.varCSA. Conventional methods in densitometry can also be used to more accurately determine the concentration or expression level of FCR3.varCSA. These approaches are also easily automated using technology known to those of skill in the art of high throughput diagnostic analysis. As detailed above, any addressable array technology known in the art can be employed with this aspect of the invention and display the protein arrays on the chips in an attempt to maximize antibody binding patterns and diagnostic information. Similar approaches can be used to detect the presence, absence, or amount of A4 tres DBL3-γ, or ItG2-CS2 DBL2-γ in a biological sample.

As discussed above, the presence or detection of FCR3.varCSA, fragments of FCR3.varCSA, A4 tres DBL3-γ, or ItG2-CS2 DBL2-γ can provide a diagnosis of a subject's disease state or predilection to disease and this information allows health professionals to create a disease state profile for a patient, begin aggressive treatment for the malaria, and prevent further worsening of the condition. Similarly, further assays and reference to the changing disease state profile can help clinicians monitor the progress of a patient during treatment. That is, once a disease state is established, a therapeutic agent is administered and an initial disease state profile is generated. The assays above can be repeated on a regular basis to evaluate whether the values in the subject's disease state profile progresses toward or returns back to the initial disease state profile. Successive treatment profiles can be used to show the efficacy of treatment over a period of several days or several months.

Additional embodiments include the preparation of diagnostic kits comprising detection components such as antibodies specific for FCR3.varCSA, fragments of FCR3.varCSA, A4 tres DBL3-γ, or ItG2-CS2 DBL2-γ or nucleic acid probes that detect the presence of these molecules. The detection component will typically be supplied in combination with one or more of the following reagents. A support capable of absorbing or otherwise binding RNA or protein will often be supplied. Available supports for this purpose include, but are not limited to, membranes of nitrocellulose, nylon or derivatized nylon that can be characterized by bearing an array of positively charged substituents, and Genechips™ or their equivalents. One or more enzymes, such as Reverse Transcriptase and/or Taq polymerase, can be furnished in the kit, as can dNTPs, buffers, or non-human polynucleotides like calf-thymus or salmon-sperm DNA. Results from the kit assays can be interpreted by a healthcare provider or a diagnostic laboratory. Alternatively, diagnostic kits are manufactured and sold to private individuals for self-diagnosis. The next section describes several embodiments that have therapeutic or prophylactic application or both.

Therapeutic and Prophylactic Applications

The varCSA modulating agents described herein are suitable for treatment of subjects either as a preventive measure to avoid maternal malaria, or as a therapeutic to treat subjects already afflicted with the disease. Although anyone could be treated with the agents of the invention as a prophylactic, the most suitable subjects are people at risk for maternal malaria. Such subjects include, but are not limited to, pregnant women living in regions of the world populated with *P. falciparum.*

The pharmacologically active compounds of this invention, including but not limited to, FCR3.varCSA, A4 tres DBL3-γ, ItG2-CS2 DBL2-γ, fragments of these molecules, nucleic acids encoding these molecules, and antibodies directed to these molecules, can be processed in accordance with conventional methods of galenic pharmacy to produce medicinal agents for administration to patients, e.g., mammals including humans. These FCR3.varCSA inhibitory agents can be incorporated into a pharmaceutical product with and without modification. Further, the manufacture of pharmaceuticals or therapeutic agents that deliver the inhibitory agent by several routes are aspects of the invention. For example, and not by way of limitation, DNA, RNA, and viral vectors having sequence encoding FCR3.varCSA or a polypeptide fragment of FCR3.varCSA are within the scope of aspects of the present invention. Nucleic acids encoding a desired FCR3.varCSA inhibitory agent can be administered alone or in combination with other varCSA inhibitory agents. Similarly nucleic acids encoding A4 tres DBL3-γ, or ItG2S2 DBL2-γ can be administered alone or in combination with other varCSA inhibitory agents.

The compounds described herein can be employed in admixture with conventional excipients, i.e., pharmaceutically acceptable organic or inorganic carrier substances suitable for parenteral, enteral (e.g., oral) or topical application that do not deleteriously react with the varCSA inhibitory agents. Suitable pharmaceutically acceptable carriers include, but are not limited to, water, salt solutions, alcohols, gum arabic, vegetable oils, benzyl alcohols, polyetylene glycols, gelatine, carbohydrates such as lactose, amylose or starch, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like that do not deleteriously react with the active compounds.

The effective dose and method of administration of a particular inhibitory agent formulation can vary based on the individual patient and the stage of the disease, as well as other factors known to those of skill in the art. Therapeutic efficacy and toxicity of such compounds can be determined by standard pharmaceutical procedures in cell cultures or experimental animals, e.g., ED50 (the dose therapeutically effective in 50% of the population) and LD50 (the dose lethal to 50% of the population). The dose ratio of toxic to therapeutic effects is the therapeutic index, and it can be expressed as the ratio, LD50/ED50. Pharmaceutical compositions that exhibit large therapeutic indices are preferred. The data obtained from cell culture assays and animal studies is used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors that may be taken into account include the prevalence of *P. falciparum* in the geographical vicinity of the patient, the severity of the disease state of the patient, age, and weight of the patient; diet, time and frequency of administration, drug combination(s), reaction sensitivities, and tolerance/response to therapy. Short acting pharmaceutical compositions are administered daily whereas long acting pharmaceutical compositions are administered every 2, 3 to 4 days, every week, or once every two weeks. Depending on half-life and clearance rate of the particular formulation, the pharmaceutical compositions of the invention are administered once, twice, three, four, five, six, seven, eight, nine, ten or more times per day.

Routes of administration of the varCSA inhibitory agents include, but are not limited to, transdermal, parenteral, gastrointestinal, transbronchial, and transalveolar. Transdermal administration is accomplished by application of a cream, rinse, gel, etc. capable of allowing the FCR3.varCSA inhibitory agent to penetrate the skin and enter the blood stream. Parenteral routes of administration include, but are not limited to, electrical or direct injection such as direct injection into a central venous line, intravenous, intramuscular, intraperitoneal or subcutaneous injection. Gastrointestinal routes of administration include, but are not limited to, ingestion and rectal. Transbronchial and transalveolar routes of administration include, but are not limited to, inhalation, either via the mouth or intranasally.

Compositions of the varCSA inhibitory agents suitable for transdermal administration include, but are not limited to, pharmaceutically acceptable suspensions, oils, creams, and ointments applied directly to the skin or incorporated into a protective carrier such as a transdermal device ("transdermal patch"). Examples of suitable creams, ointments, etc. can be found, for instance, in the Physician's Desk Reference. Examples of suitable transdermal devices are described, for instance, in U.S. Pat. No. 4,818,540 issued Apr. 4, 1989 to Chinen, et al.

Compositions of the varCSA inhibitory agents suitable for parenteral administration include, but are not limited to, pharmaceutically acceptable sterile isotonic solutions. Such solutions include, but are not limited to, saline and phosphate buffered saline for injection into a central venous line, intravenous, intramuscular, intraperitoneal, or subcutaneous injection of the FCR3.varCSA inhibitory agents.

Compositions of the varCSA inhibitory agents suitable for transbronchial and transalveolar administration include, but not limited to, various types of aerosols for inhalation. Devices suitable for transbronchial and transalveolar administration of the FCR3.varCSA inhibiting agents are also embodiments. Such devices include, but are not limited to, atomizers and vaporizers. Many forms of currently available atomizers and vaporizers can be readily adapted to deliver varCSA inhibitory agents.

Compositions of the varCSA inhibitory agents suitable for gastrointestinal administration include, but not limited to, pharmaceutically acceptable powders, pills or liquids for ingestion and suppositories for rectal administration. Due to the ease of use, gastrointestinal administration, particularly oral, is the preferred embodiment of the present invention.

Several methods of treatment and prevention of maternal malaria, which involve administration of the pharmaceutical embodiments of the invention are provided. In these aspects of the invention, FCR3.varCSA, fragments of FCR3.varCSA, A4 tres DBL3-γ, or ItG2-CS2 DBL2-γ, nucleic acids encoding these molecules, and agents that interact with a varCSA-CSA complex are incorporated into pharmaceuticals and are administered to patients in need. Because aspects of the invention that incorporate a varCSA molecule or fragments thereof can both interrupt varCSA mediated adhesion and stimulate an immune response to these polypeptides, significant therapeutic and prophylactic benefit can be achieved by administration of these agents to patients in need. Thus, in some contexts, a therapeutic protocol can also be termed a method of vaccination. By one approach, a subject at risk for contracting maternal malaria or a subject infected with *P. falciparum* is identified by conventional techniques or the diagnostic assays described above and then a therapeutically or prophylactically beneficial amount of a varCSA molecule or fragment thereof is administered.

Although the invention has been described with reference to embodiments and examples, it should be understood that various modifications can be made without departing from the spirit of the invention. Accordingly, the invention is limited only by the following claims. All references cited herein are hereby expressly incorporated by reference.

What is claimed is:

1. A purified or isolated protein comprising the sequence of SEQ ID NO:2.

2. A purified or isolated polypeptide comprising a DBL3 domain of residues 1279–1554 of SEQ ID NO:2 or an immunogenic fragment thereof consisting of at least 15 or 30 amino acids of residues 1279–1554 of SEQ ID NO:2.

3. The purified or isolated polypeptide of claim 2, wherein the polypeptide is the DBL3 domain of residues 1279–1554 of SEQ ID NO:2.

4. The purified or isolated polypeptide of claim 2, wherein the polypeptide is an immunogenic fragment consisting of at least 15 amino acids of residues 1279–1554 of SEQ ID NO:2.

5. The purified or isolated polypeptide of claim 2, wherein the polypeptide is an immunogenic fragment consisting of at least 30 amino acids of residues 1279–1554 of SEQ ID NO:2.

6. An immunogenic composition comprising the protein or polypeptide of any of claim 1, 3, 4, or 5 in combination with a pharmaceutically acceptable carrier or adjuvant.

7. A method of inducing an immune response comprising administering the composition of claim 6 to a subject in need thereof, wherein an immune response is induced.

8. The method of claim 7 wherein the subject is at risk for maternal malaria.

* * * * *

UNITED STATES PATENT AND TRADEMARK OFFICE

CERTIFICATE OF CORRECTION

PATENT NO. : 6,855,323 B2
APPLICATION NO. : 10/087013
DATED : February 15, 2005
INVENTOR(S) : Scherf et al.

It is certified that error appears in the above-identified patent and that said Letters Patent is hereby corrected as shown below:

At column 88, line 15, claim 6, after “any” insert --one--.

Signed and Sealed this

Thirty-first Day of October, 2006

JON W. DUDAS
*Director of the United States Patent and Trademark Office*